US008153781B2

(12) United States Patent
Jacobson et al.

(10) Patent No.: US 8,153,781 B2
(45) Date of Patent: Apr. 10, 2012

(54) DENDRIMER CONJUGATES OF AGONISTS AND ANTAGONISTS OF THE GPCR SUPERFAMILY

(75) Inventors: Kenneth A. Jacobson, Silver Spring, MD (US); Yoonkyung Kim, Seoul (KR); Athena Klutz, Adelphi, MD (US); Beatrice Hechler, Strasbourg (FR); Christian Gachet, Lalaye (FR)

(73) Assignees: The United States of America as represented by the Secretary, Department of Health and Human Services, Washington, DC (US); Inserm, Paris (FR)

( * ) Notice: Subject to any disclaimer, the term of this patent is extended or adjusted under 35 U.S.C. 154(b) by 423 days.

(21) Appl. No.: 12/143,451

(22) Filed: Jun. 20, 2008

(65) Prior Publication Data

US 2009/0012035 A1 Jan. 8, 2009

Related U.S. Application Data

(60) Provisional application No. 60/947,121, filed on Jun. 29, 2007, provisional application No. 61/045,498, filed on Apr. 16, 2008.

(51) Int. Cl.
*C07H 19/22* (2006.01)
(52) U.S. Cl. ............... 536/27.13; 536/22.1; 536/23.1; 536/25.3; 536/27.1; 536/27.14; 536/27.2; 536/27.21; 536/27.23; 536/27.3
(58) Field of Classification Search ................ None
See application file for complete search history.

(56) References Cited

U.S. PATENT DOCUMENTS

| | | | |
|---|---|---|---|
| 5,280,015 A | 1/1994 | Jacobson et al. |
| 5,284,834 A | 2/1994 | Jacobson et al. |
| 5,620,676 A | 4/1997 | Jacobson et al. |
| 5,688,774 A | 11/1997 | Jacobson et al. |
| 5,773,423 A | 6/1998 | Jacobson et al. |
| 5,840,728 A | 11/1998 | Marquez et al. |
| 6,211,165 B1 | 4/2001 | Liang et al. |
| 6,316,423 B1 | 11/2001 | Von Lubitz et al. |
| 6,376,521 B1 | 4/2002 | Jacobson et al. |
| 6,586,413 B2 | 7/2003 | Liang et al. |
| 7,087,589 B2 | 8/2006 | Jacobson et al. |
| 7,199,127 B2 | 4/2007 | Jeong et al. |
| 2007/0232626 A1 | 10/2007 | Jacobson et al. |
| 2007/0265223 A1 | 11/2007 | Tomaselli et al. |

FOREIGN PATENT DOCUMENTS

| | | |
|---|---|---|
| WO | WO 01/51490 A1 | 7/2001 |
| WO | WO 2006/031505 A1 | 3/2006 |
| WO | WO 2006/113204 A2 | 10/2006 |
| WO | WO 2006/128159 A2 | 11/2006 |
| WO | WO 2008/006369 A1 | 1/2008 |

OTHER PUBLICATIONS

Greenwald et al., "Poly(ethylene glycol) Conjugated Drugs and Prodrugs: A Comprehensive Review," *Critical Reviews in Therapeutic Drug Carrier Systems*, 17 (2), 101-161 (2000).
Jacobson et al., "Functionalized Congeners of Adenosine: Preparation of Analogues with High Affinity for $A_1$-Adenosine Receptors," *J. Med. Chem.*, 28, 1341-1346 (1985).
Jacobson et al., "A Functionalized Congener Approach to Adenosine Receptor Antagonists: Amino Acid Conjugates of 1,3-Dipropylxanthine," *Mol. Pharmacol.*, 29, 126-133 (1986).
Jacobson et al., "A Novel Pharmacological Approach to Treating Cardiac Ischemia," *J. Biol. Chem.*, 275 (39), 30272-30279 (2000).
Jacobson et al., "Functionalized congeners of 1,3-dialkylxanthines: Preparation of Analogues with High Affinity for Adenosine Receptors," *J. Med. Chem.*, 28,1334-1340 (1985).
Jacobson et al., "$N^6$-Functionalized Congeners of Adenosine with High Potency at $A_2$-Adenosine Receptors: Potential Ligands for Affinity Chromatography," *Biochem. Biophys. Res. Commun.*, 136 (3), 1097-1102 (1986).
Jacobson et al., "Xanthine Functionalized Congeners as Potent Ligands at $A_2$-Adenosine Receptors," *J. Med. Chem.*, 30, 211-214 (1987).
Jacobson et al., "Purine Functionalized Congeners as Molecular Probes for Adenosine Receptors," *Nucleos. Nucleotid.*, 10 (5), 1029-1038 (1991).
Abbracchio et al., "International Union of Pharmacology LVIII: Update on the P2Y G Protein-Coupled Nucleotide Receptors: From Molecular Mechanisms and Pathophysiology to Therapy," *Pharmacol. Rev.*, 58, 281-341 (2006).
Hechler et al., ATP Derivatives Are Antagonists of the $P2Y_1$ Receptor: Similarities to the Platelet ADP Receptor, *Molecular Pharmacology*, 53, 727-733 (1998).
Jacobson et al., "Molecular Recognition at Adenine Nucleotide (P2) Receptors in Platelets," *Seminars in Thrombosis and Hemostasis*, 31(2), 205-216 (2005).

*Primary Examiner* — Patrick Lewis
(74) *Attorney, Agent, or Firm* — Leydig, Voit & Mayer, Ltd.

(57) ABSTRACT

Disclosed are conjugates comprising a dendrimer and a ligand, which is a functionalized congener of an agonist or antagonist of a receptor of the G-protein coupled receptor (GPCR) superfamily, for example, wherein the functionalized congener is an $A_1$ adenosine receptor agonist having a purine nucleoside moiety and a functional group at the $N^6$ position of the purine nucleoside moiety, wherein the functional group has the formula (I):
$N^6H$—$Ar^1$—$CH_2$—$C(=O)NH$—$R^1$ (I), wherein $Ar^1$ and $R^1$ as defined herein. Also disclosed are pharmaceutical compositions, methods of treating various diseases, and a diagnostic method employing such conjugates.

56 Claims, 62 Drawing Sheets

FIG. 1
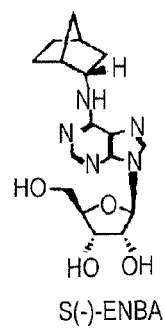
S(-)-ENBA
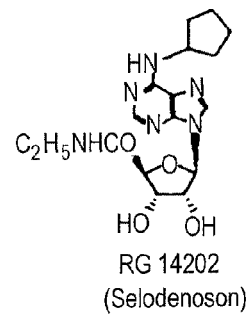
RG 14202
(Selodenoson)
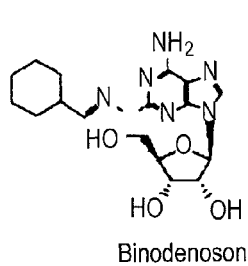
Binodenoson
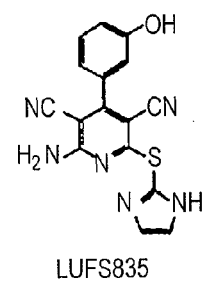
LUFS835
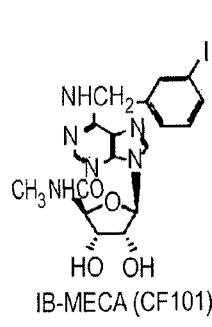
IB-MECA (CF101)
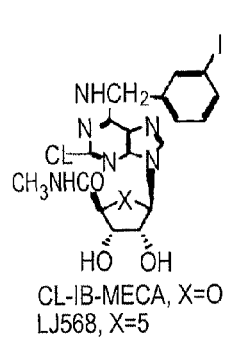
CL-IB-MECA, X=O
LJ568, X=S
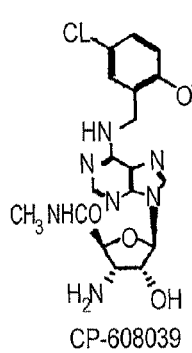
CP-608039
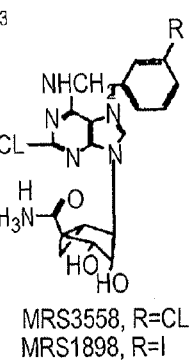
MRS3558, R=CL
MRS1898, R=I

FIG. 2

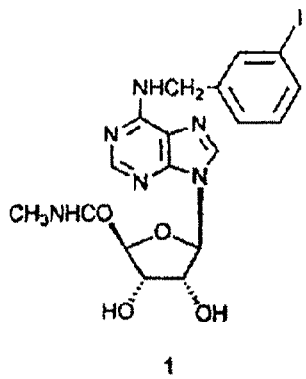

1

A₃ agonist
(IB-MECA, CF101,
in clinical trials for cancer
and arthritis)

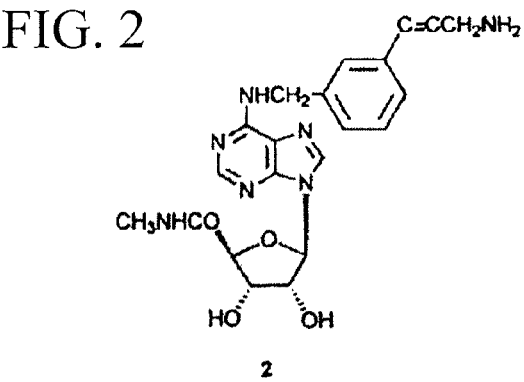

2

A₃ agonist
(amine functionalized congener
applied successfully to
dual acting A1/A3 agonist)

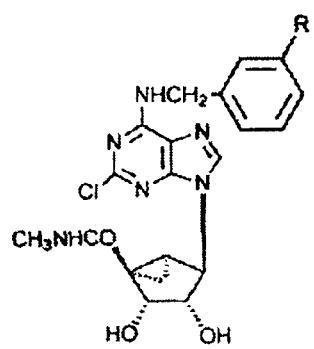

3a  R = Cl  MRS3558
3b  R = I   MRS1898

A₃ agonists
(containing (N)-methanocarba
ng system to enhance hA₃ affinity)

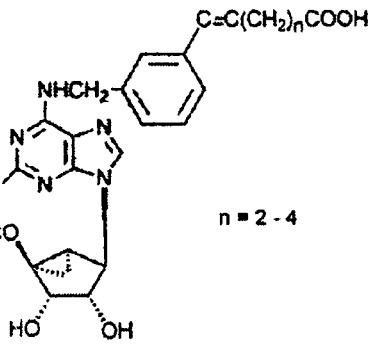

4

A₃ agonists
(carboxylic acid functionalized
congener, proposed for
conjugation to PAMAM dendrimers)

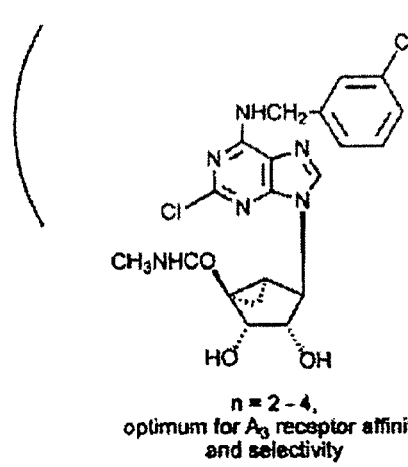

n = 2 - 4,
optimum for A₃ receptor affinity
and selectivity

5

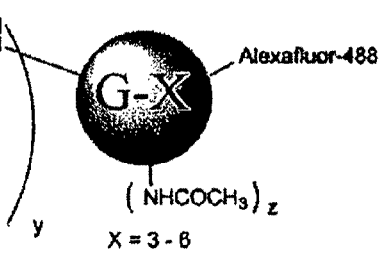

X = 3 - 6

For X = 3,
y + z = 31
y will be varied from
1 to 31

Scheme 1

Scheme 2

Scheme 3

Scheme 4

FIG. 10
Scheme 5
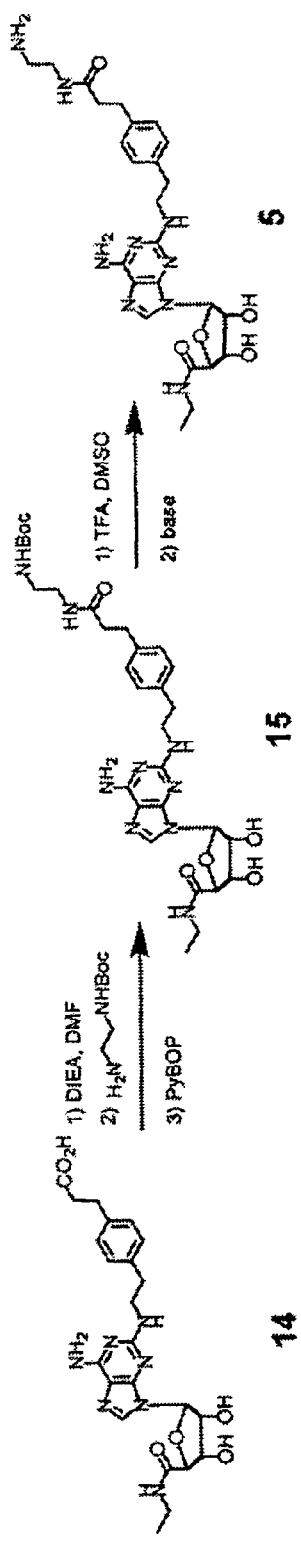
Scheme 6
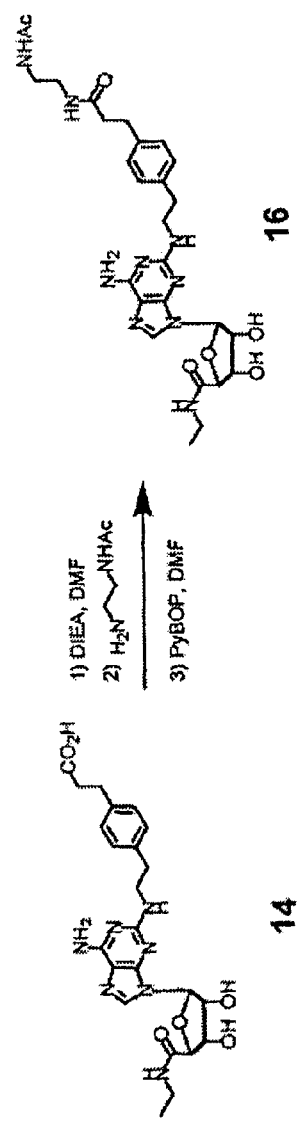

Scheme 7

Scheme 8

Scheme 9

Scheme 11

Scheme 12

Scheme 13
FIG. 17A
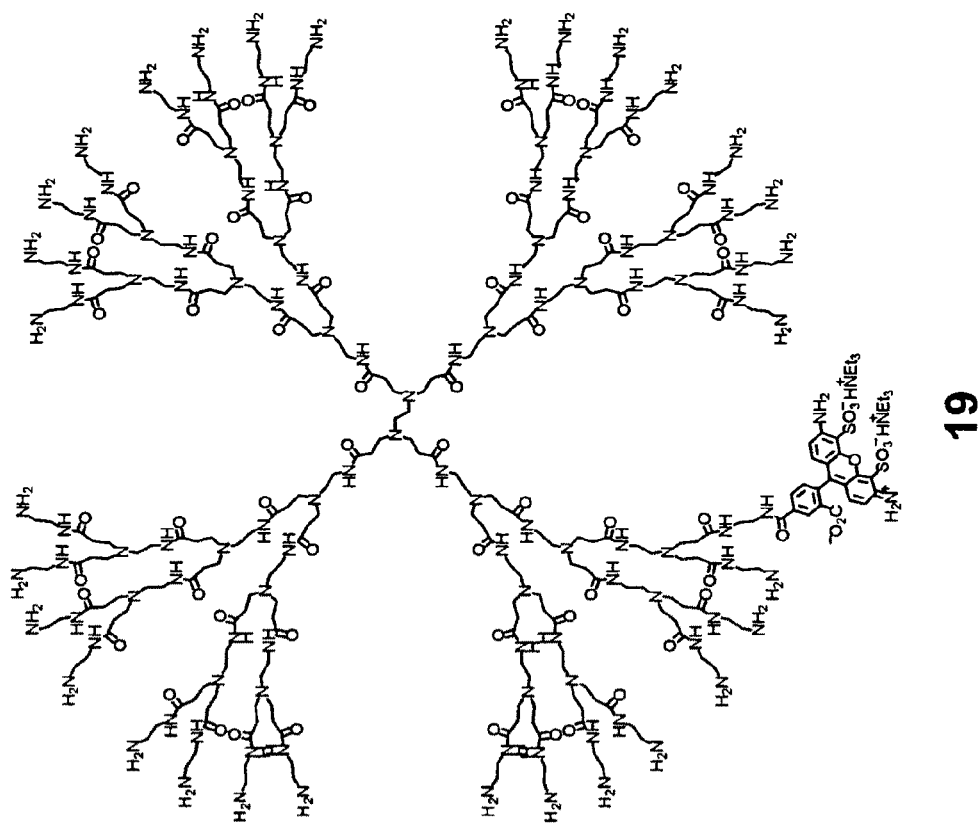
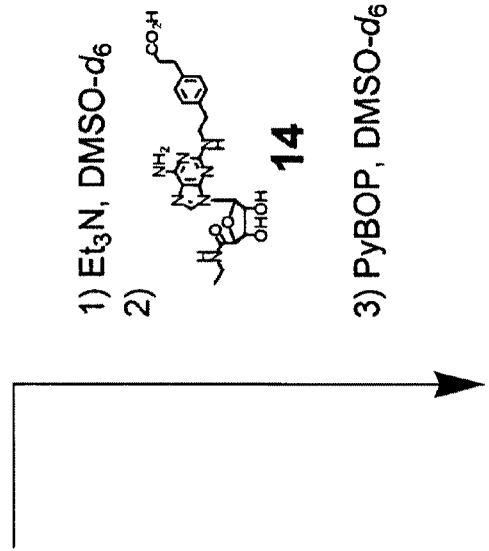

Scheme 15

Scheme 16

FIG. 21
Scheme 17
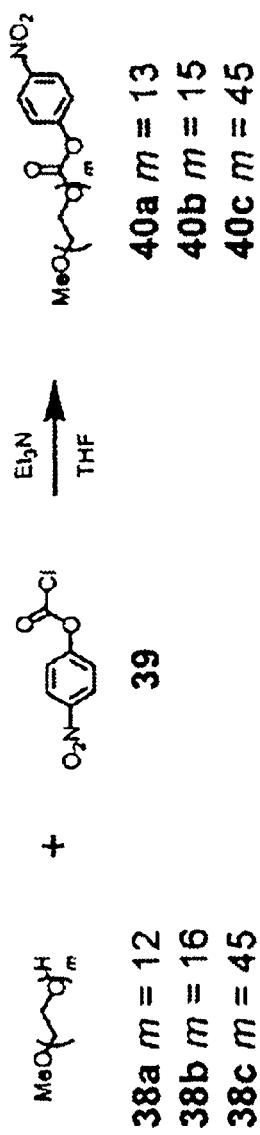
Scheme 18
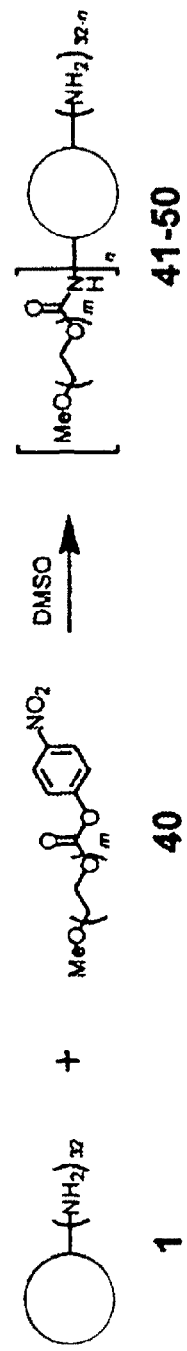

Scheme 19

FIG. 23
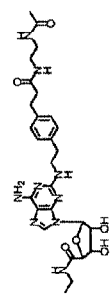
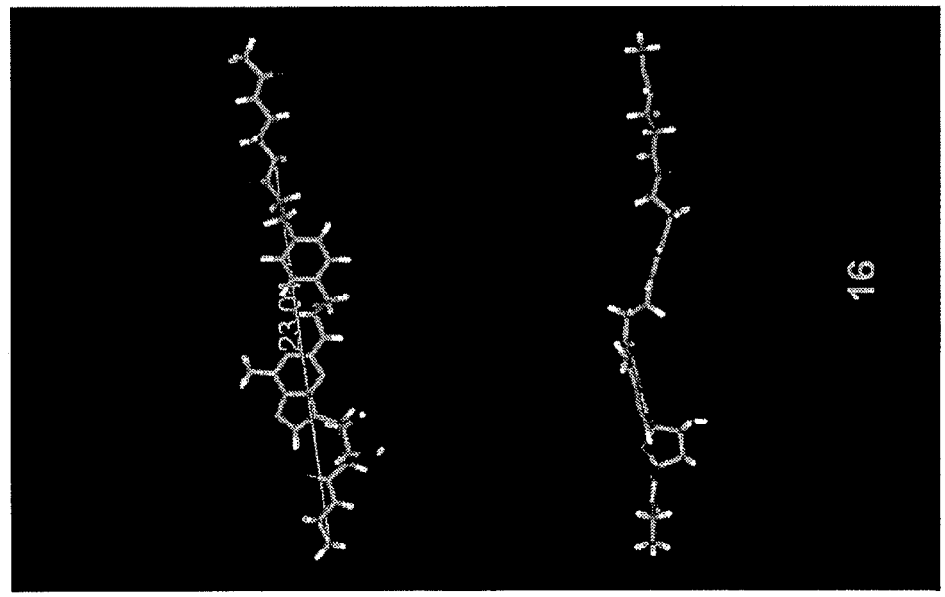
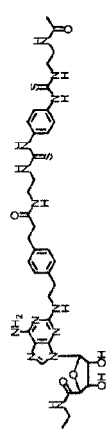
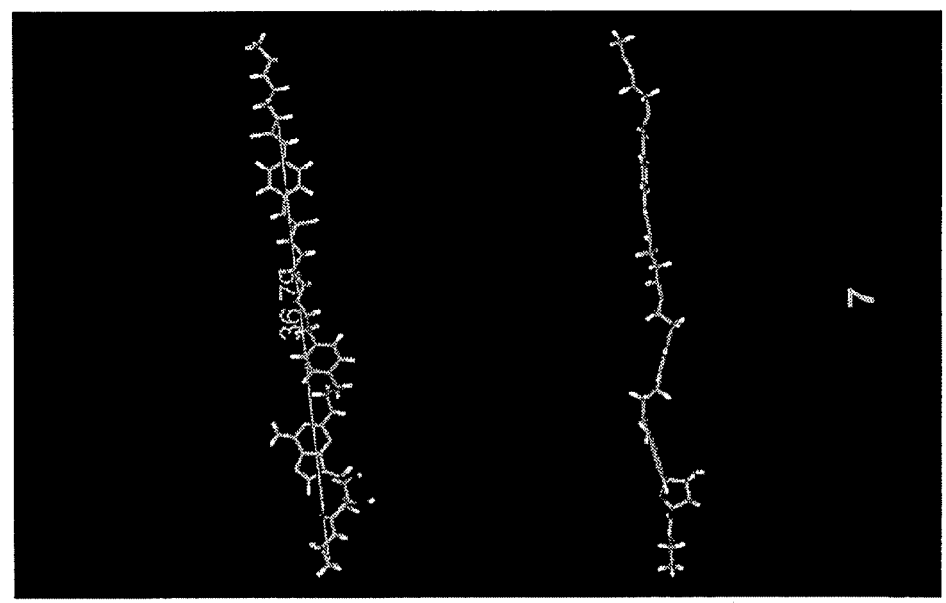

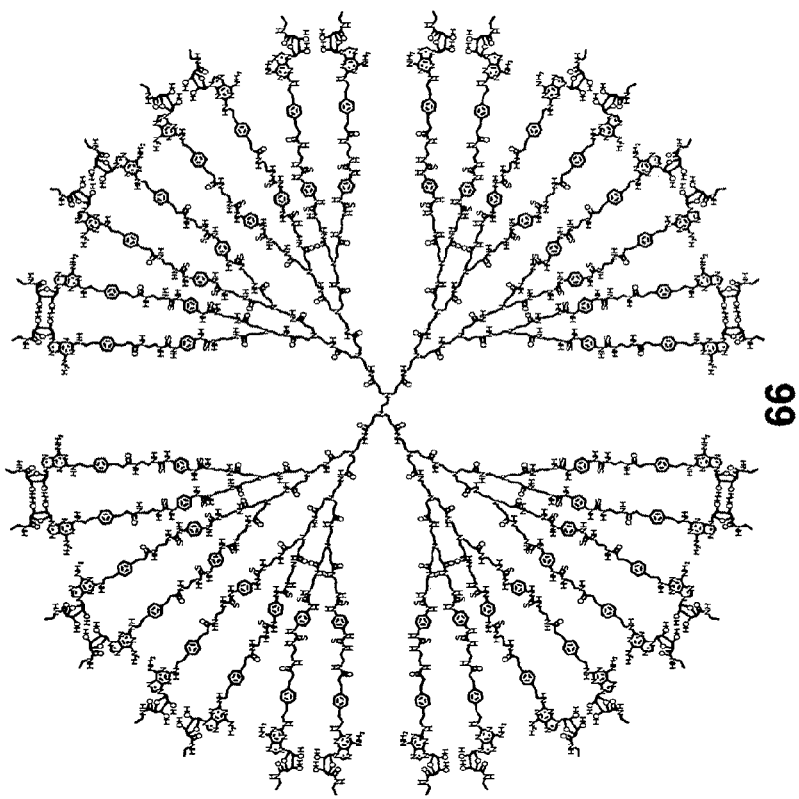
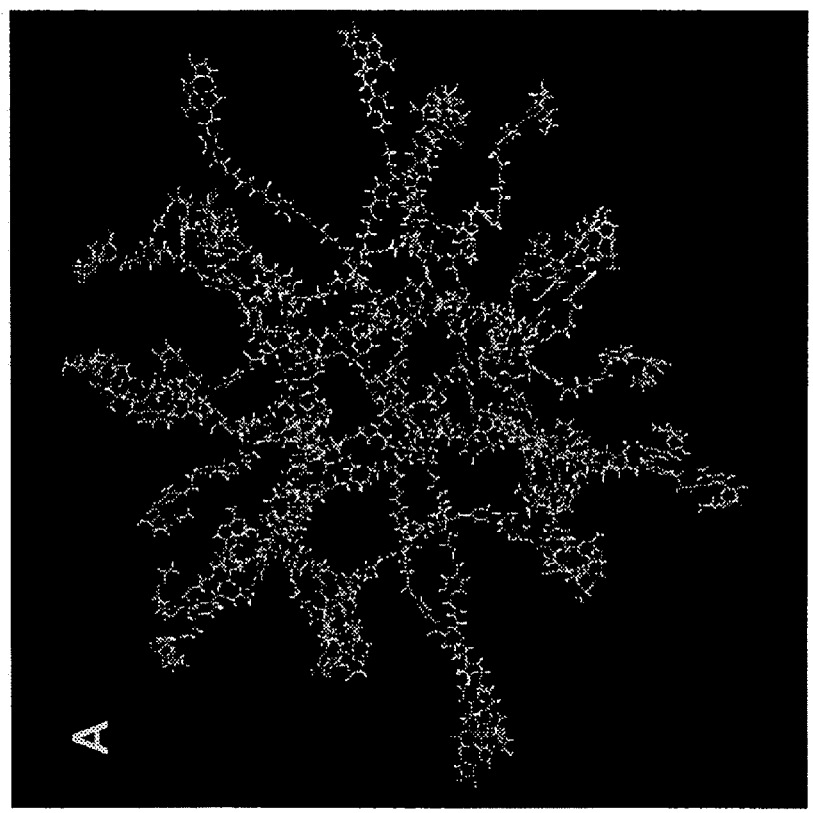
FIG. 24A

Activation of $A_{2A}$ AR by PAMAM Dendrimer Derivatives

*Stimulation of adenylate cyclase in HEK293 cells expressing the human $A_{2A}$ receptor. Percent of the maximal effect of a full agonist NECA, 10 μM.

101

MRS5183 (117)

PAMAMG2.5 + Alexa Fluor488 + 3 5169

Dendrimer conjugates of P2Y14 nucleotide receptor agonists

DENDRIMER CONJUGATES OF AGONISTS AND ANTAGONISTS OF THE GPCR SUPERFAMILY

CROSS-REFERENCE TO RELATED APPLICATIONS

This application claims the benefit of U.S. Provisional Patent Application Nos. 60/947,121, filed Jun. 29, 2007 and 61/045,498, filed Apr. 16, 2008, the disclosures of which are incorporated by reference.

BACKGROUND OF THE INVENTION

Attempts have been made to covalently link certain drugs, for example, taxol, cisplatin, methotrexate, and ibuprofen, to dendrimers, which are polymers made from branched monomers through the iterative organic synthesis by adding one layer (i.e., generation) at each step to provide a symmetrical structure. Such dendrimer conjugates have one or more advantages, for example, altered pharmacokinetics, decreased toxicity, and increased solubility. Agonists and antagonists of the receptors of the G-protein coupled receptor (GPCR) superfamily are useful in the treatment of a number of diseases, for example, the agonist of one member of the GPCR superfamily, the $A_1$ adenosine receptor, is useful for treating a number of diseases including cognitive disease, stroke, epilepsy, and migraine. There is a desire to obtain dendrimer conjugates of agonists and antagonists of the GPCR superfamily of receptors.

BRIEF SUMMARY OF THE INVENTION

The invention provides a conjugate comprising a dendrimer and at least one ligand, which is a functionalized congener of an agonist or antagonist, of a receptor of the G-protein coupled receptor (GPCR) superfamily. The invention further provides pharmaceutical compositions and methods of treating various diseases. The invention also provides diagnostic methods employing such conjugates.

BRIEF DESCRIPTION OF THE SEVERAL VIEWS OF THE DRAWINGS

FIG. 1 depicts the structures of certain adenosine receptor agonists in accordance with an embodiment of the invention.

FIG. 2 depicts the structures of certain $A_3$ adenosine receptor agonists in accordance with an embodiment of the invention.

FIG. 10 depicts Schemes 5 and 6, reaction schemes to prepare compounds 5 and 16.

FIG. 17A depicts the first part of Scheme 13, a reaction scheme to prepare dendrimer conjugate 33, in accordance with an embodiment of the invention.

FIG. 21 depicts Schemes 17 and 18, reaction schemes to prepare PEG derivatives 40a-40c and PEG-dendrimer conjugates 41-50, in accordance with an embodiment of the invention.

FIG. 23 depicts energy-minimized structures of 7 (acetylated APEC, left) and 16 (CGS21680, right). Calculation proceeded using the HyperChem7.5.2 software through a semi-empirical PM3 method.

FIG. 24A depicts energy minimized structure of PAMAM G3 conjugate with 32 attachments of (A) APEC (66) and FIG. 24B depicts energy minimized structure of conjugate (B) CGS21680 (17). Calculation proceeded using the HyperChem7.5.2 software through an Amber force field.

DETAILED DESCRIPTION OF THE INVENTION

Figure 3:
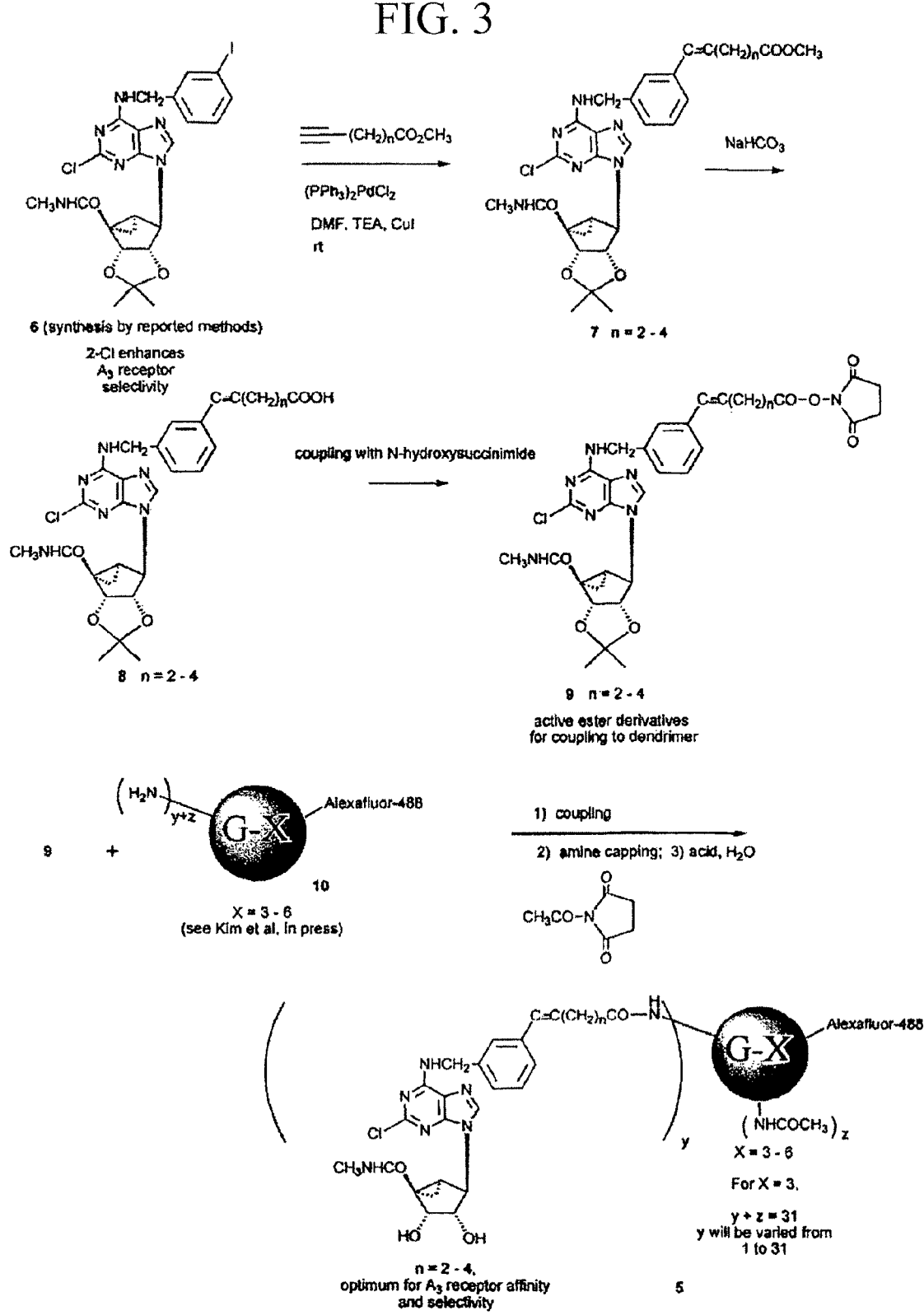
FIG. 3 depicts a method of preparation of a dendrimer conjugate comprising an A3 adenosine receptor agonist in accordance with an embodiment of the invention.

The present invention provides a conjugate comprising a dendrimer, at least one ligand covalently linked to the dendrimer, and optionally one or more surface modifying moieties covalently linked to the dendrimer, wherein the ligand is a functionalized congener of an agonist or antagonist of a receptor of the G-protein coupled receptor (GPCR) superfamily.

The conjugate can comprise a ligand containing an agonist or antagonist of any member of the GPCR family receptors including the four subtypes of adenosine receptors and eight subtypes of nucleotide P2Y receptors as well as muscarinic receptors, in particular, the ligand is a functionalized congener of an agonist or antagonist of an adenosine receptor selected from the group consisting of $A_1$, $A_{2A}$, $A_{2B}$, and $A_3$ adenosine receptors, of $P2Y_1$ and $P2Y_{14}$ receptors, and of the $M_1$ muscarinic receptor.

Dendrimers are classified as polymers; however, they are made from branched monomers through the iterative organic synthesis by adding one layer (i.e., generation) at each step to provide a perfectly symmetrical structure. The solution conformation of higher generation dendrimers may closely mimic the size and shape of a protein. Furthermore, dendrimers possess favorable characteristics: structural integrity, control of component functional groups—and their physical properties—by chemical synthesis, feasibility to conjugate multiple functional units at the peripheries and interiors, and a low enzymatic degradation rate. The dendrimer can be of any suitable generation, e.g., from 2 to 10 or more, including fractional generations, particularly 2 to 8, e.g., 2, 2.5, 3, 3.5, 4, 4.5, 5, 5.5, 6, 6.5, 7, or 7.5. The dendrimer can be anionic or cationic. For example, the half generations are carboxyl terminated and full generations are amine terminated. The conjugate of the invention can include any suitable dendrimer, particularly a poly(amidoamine) (PAMAM) dendrimer.

In accordance with an embodiment, the invention provides a conjugate wherein the ligand is a functionalized congener of an $A_1$ adenosine receptor agonist. Any suitable $A_1$ adenosine receptor agonist can be part of the conjugate of the invention. Examples of suitable $A_1$ adenosine receptor agonists are adenosine, 6-cyclopropyl adenosine, 2-chloro, 6-cyclopropyl adenosine, S(−)-ENBA (FIG. 1), N6-[4-(2-aminoethylaminocarbonylmethyl)phenyl]adenosine (ADAC), 1S-[1a,2b,3b,4a(S*)]-4-[7-[[1-[(3-chloro-2-thienyl)methylpropyl]propyl-amino]-3H-imidazo[4,5-b]pyridyl-3-yl]-N-ethyl-2,3-dihydroxycyclopentane carboxamide (AMP579), 2-chloro-N[6]-[(R)-(benzothiazolylthio-2-propyl]adenosine (NNC 21-0136), (N-[1S trans-2-hydroxycyclopentyl]adenosine) (GR 79236), N-(3-tetrahydrofuranyl)-6-aminopurine riboside (Tecadenoson or CVT-510), (((5-(6-(oxolan-3-yl) amino)purin-9-yl)-3,4-dihydroxyoxolan-2-yl)methoxy)-N-methylcarboxamide (CVT-2759), Selodenoson (FIG. 1), and 6-cyclohexyl-2'-O-methyl-adenosine (SDZ WAG 994). The conjugate can contain one or more agonists on the same dendrimer molecule. In a preferred embodiment, the $A_1$ adenosine receptor agonist is N6-[4-(2-aminoethylaminocarbonylmethyl)phenyl]adenosine (ADAC) or a functionalized congener thereof.

In accordance with embodiment of the invention, the conjugate comprises a functionalized congener of an $A_1$ adenosine receptor agonist having a purine nucleoside moiety and a functional group at the N6 position of the purine nucleoside moiety, wherein the functional group has the formula (I):

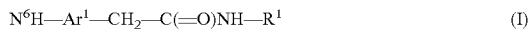

$N^6H-Ar^1-CH_2-C(=O)NH-R^1$ (I)

wherein the functional group has the formula (I), the functionalized congener has one of the following formulas (Ia)-(Ic):

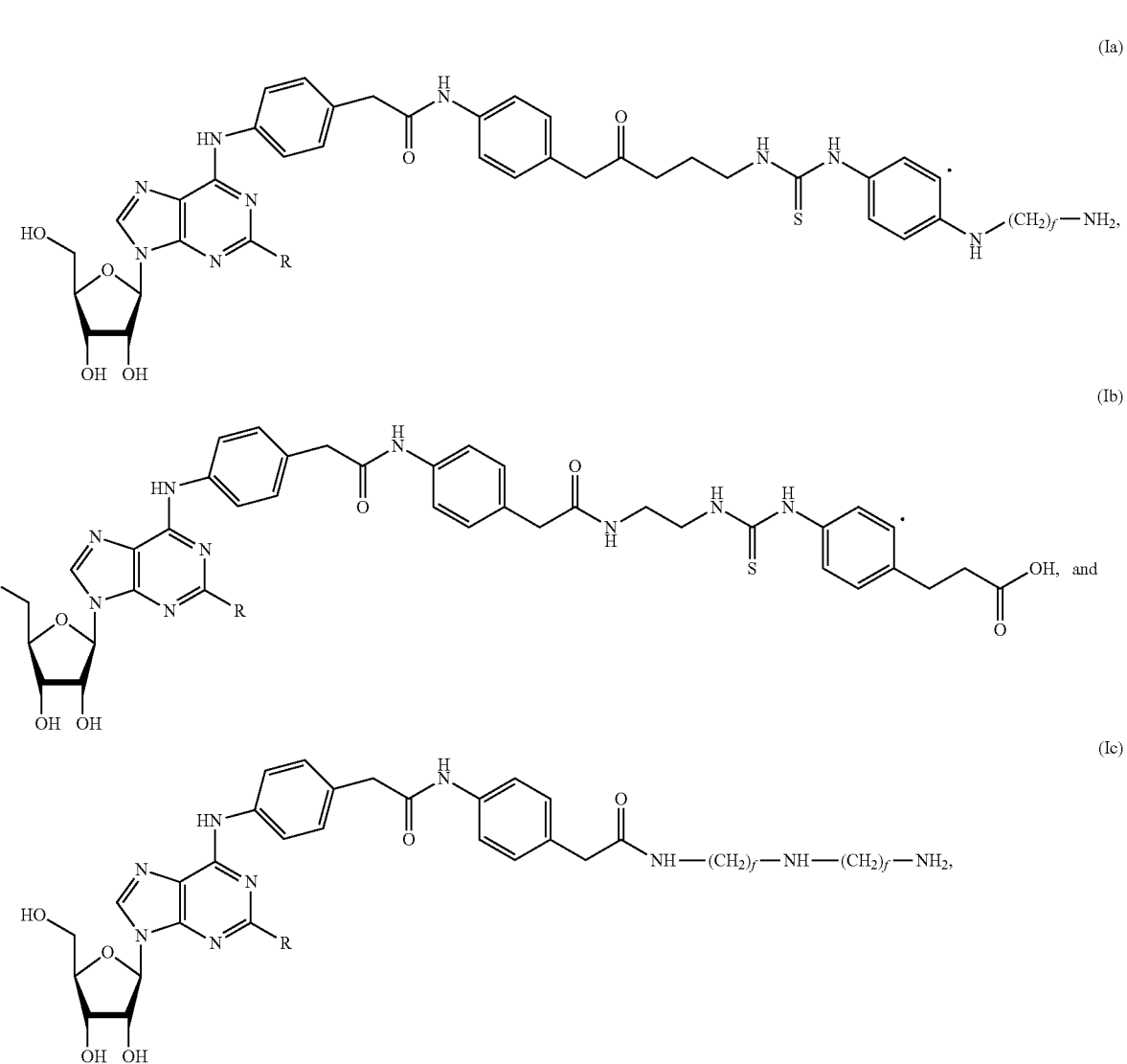

wherein $R^1$ is $Ar^2-CH_2-C(=O)NH-(CH_2)_a-NH-R^2$, $Ar^2-CH_2-C(=O)(CH_2)_a-NH-R^2$ or $[(CH_2)_b-NH]_c-R^2$ and $R^2$ is H or $C(=O)NH-Ar^3-(CH_2)_c-C(=O)OH$, $C(=O)R^3$, $C(=S)Ar^4-NCS$, or $C(=S)Ar^4-NH(CH_2)_fNH_2$, wherein $Ar^1$, $Ar^2$, $Ar^3$, and $Ar^4$ are $C_6$-$C_{20}$ aryl, $R^3$ is $C_1$-$C_6$ alkyl, and a, b, c, and f are independently 1-6.

In accordance with an embodiment, in formula (I), preferably $Ar^1$, $Ar^2$, $Ar^3$, and $Ar^4$ are phenyl. In any of the embodiments, in formula (I), preferably $R^3$ is $C_1$-$C_3$ alkyl, particularly methyl. In any of the embodiments, in formula (I), preferably a, b, and c are independently 1 to 3, and more preferably 1.

In accordance with an embodiment of the conjugate comprising a functionalized congener of an $A_1$ adenosine receptor agonist having a purine nucleoside moiety and a functional group at the $N^6$ position of the purine nucleoside moiety, wherein R is hydrogen or halo, i.e., fluoro, chloro, bromo, or iodo.

In accordance with another embodiment, the invention provides a conjugate wherein the ligand is a functionalized congener of an $A_{2A}$ adenosine receptor agonist. Any suitable $A_{2A}$ adenosine receptor agonist can be part of the conjugate of the invention. Examples of suitable $A_{2A}$ adenosine receptor agonists are 2-[4-(2-aminoethylaminocarbonylethyl)phenylethylamino]-5'-N-ethylcarboxamidoadenosine (APEC), 2-[4-(2-carboxylethyl)phenylethylamino]-5'-N-ethylcarboxamidoadenosine (CGS21680), adenosine 5'-N-ethylcarboxamide (NECA), (2-[2-(4-chlorophenyl)-ethoxy]-adenosine) (MRE 9004), $N^6$-[2-(3,5-dimethoxyphenyl)-2-(2-methylphenyl)-ethyl]adenosine (DPMA), and binodenoson (FIG. 1), particularly APEC and CGS21680.

In accordance with an embodiment, the invention provides a conjugate comprising a functionalized congener of an $A_{2A}$ adenosine receptor agonist having a purine nucleoside moiety and a functional group at the 2-position of the purine nucleoside moiety, wherein the functional group has the formula (II):

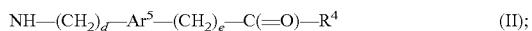

$$NH-(CH_2)_d-Ar^5-(CH_2)_e-C(=O)-R^4 \quad (II);$$

wherein $R^4$ is OH or $NH-(CH_2)_f-NH-R^5$ wherein $R^5$ is H, $C(=O)R^3$, $(CH_2)_fNH_2$, or $C(=S)-NH-Ar^6-R^6$, wherein $R^6$ is NCS, $NH-(C=S)-NH-(CH_2)_g-NH_2$, $(CH_2)_hCOOH$, or $(CH_2)_i-NH-C(=O)R^3$, wherein $Ar^5$ and $Ar^6$ are $C_6$-$C_{20}$ aryl, $R^3$ is $C_1$-$C_6$ alkyl, and d to i are independently 1-6.

In accordance with an embodiment, in formula (II), preferably $Ar^5$ and $Ar^6$ are phenyl. In any of the embodiments, in formula (II), preferably $R^3$ is $C_1$-$C_3$ alkyl, particularly methyl. In any of the embodiments, in formula (II), preferably d to i are independently 1, 2, or 3.

In accordance with an embodiment of the conjugate comprising a functionalized congener of an $A_{2A}$ adenosine receptor agonist having a purine nucleoside moiety and a functional group at the $N^6$ position of the purine nucleoside moiety, wherein the functional group has the formula (II), the functionalized congener has one of the following formulas (IIa)-(IIe):

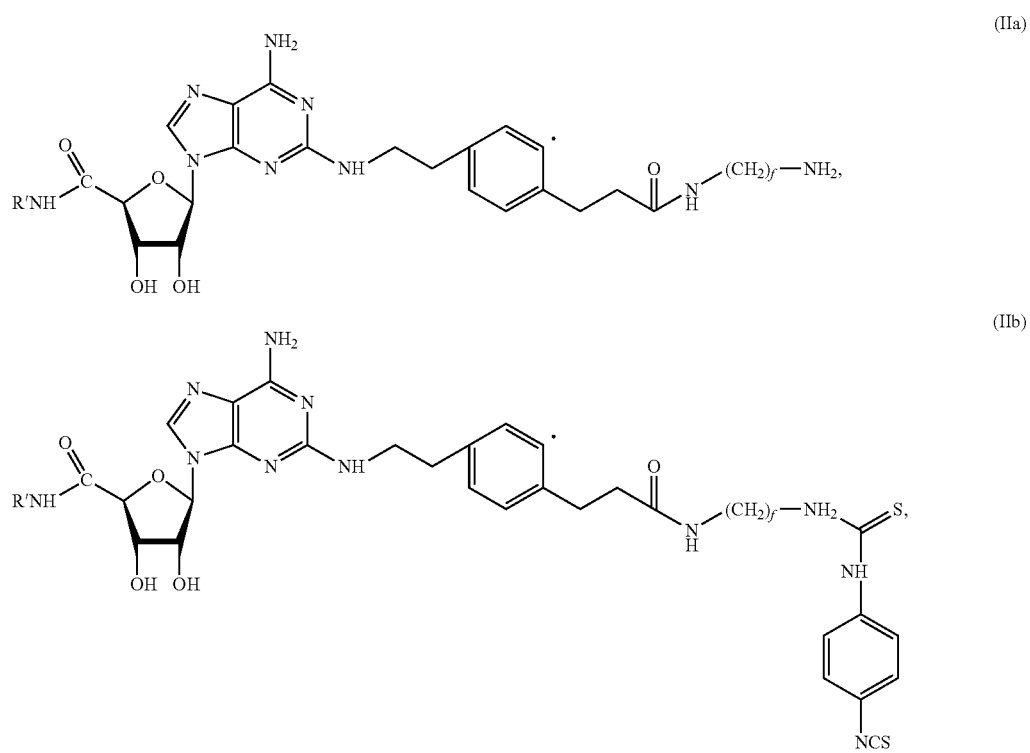

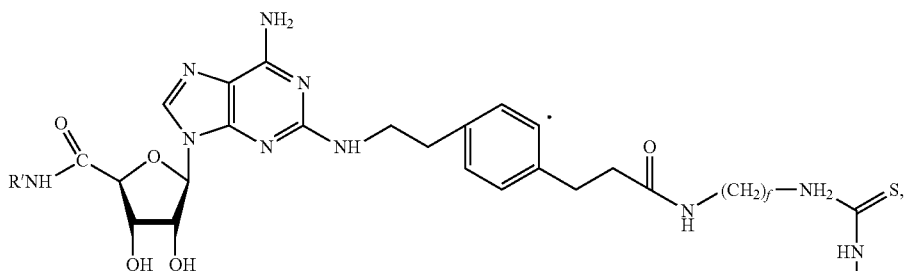

(IIc)

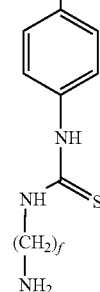

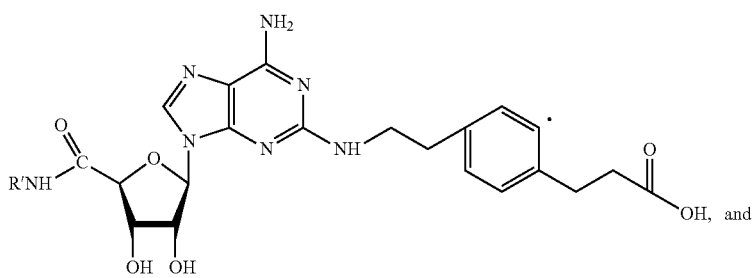

(IId)

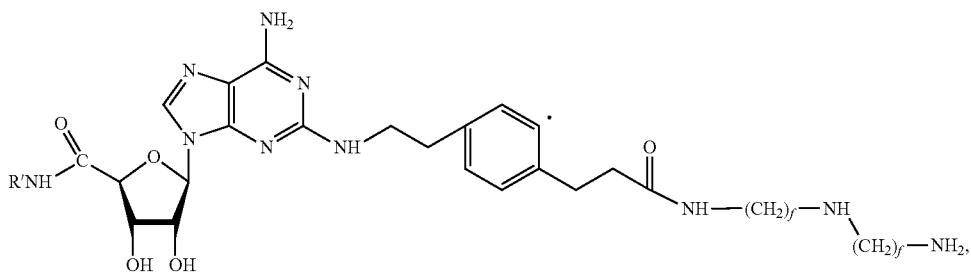

(IIe)

wherein R' is $C_1$-$C_4$ alkyl, preferably methyl, ethyl, n-propyl, or isopropyl.

In accordance with yet another embodiment, the invention provides a conjugate wherein the ligand is a functionalized congener of an $A_{2B}$ adenosine receptor agonist. Any suitable $A_{2B}$ adenosine receptor agonist can be part of the conjugate of the invention. An example of a suitable $A_{2B}$ adenosine receptor agonist is LUF5835 (FIG. 1).

In accordance with a further embodiment, the invention provides a conjugate wherein the ligand is a functionalized congener of an $A_3$ adenosine receptor agonist. Any suitable $A_3$ adenosine receptor agonist can be part of the conjugate of the invention. Examples of suitable $A_3$ adenosine receptor agonists are IB-MECA, Cl-IB-MECA, CP-608039, MRS3558, and MRS1898 (FIG. 1).

In accordance with an embodiment of the conjugate comprising a functionalized congener of an $A_3$ adenosine receptor agonist having a purine nucleoside moiety and a functional group at the $N^6$ position of the purine nucleoside moiety, wherein the functional group has the formula (III), wherein the functionalized congener is (a) an $A_3$ adenosine receptor agonist having a purine nucleoside moiety with a native ribose unit at the $N^7$-position and a functional group of the purine nucleoside moiety at the $N^6$-position, wherein the functional group has the formula (III)):

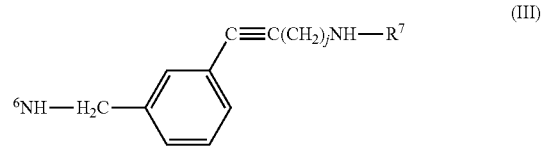

(III)

wherein $R^7$ is H,

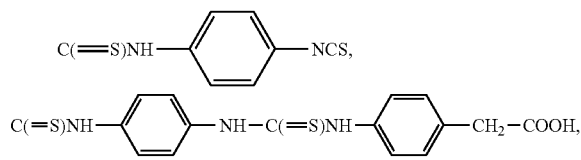

or C(=O)R$^3$, wherein R$^3$ is C$_1$-C$_6$ alkyl, and j is 1 to 6;

or (b) an A$_3$ adenosine receptor agonist having a purine nucleoside moiety with a methanocarba adenine nucleoside unit at the N$^7$-position and a functional group at the 2-position of the nucleoside moiety, wherein the functional group has the formula (IV):

$$C\equiv C-(CH_2)_kC(=O)-R^7 \quad (IV),$$

wherein R$^7$ is OH or NH—(CH$_2$)$_l$—NHR$^8$ wherein R$^8$ is H, C(=O)R$^3$, or C(=S)NH—Ar$^7$—R$^9$ wherein R$^3$ is C$_1$-C$_6$ alkyl, R$^9$ is NCS, NH—C(=S)—NH—(CH$_2$)$_m$—NH$_2$, or (CH$_2$)$_n$COOH, wherein Ar$^7$ is C$_6$-C$_{20}$ aryl, and k to n are independently 1 to 6.

In accordance with an embodiment, in formula (IV), preferably Ar$^7$ is phenyl. In any of the embodiments, in formula (IV), preferably R$^3$ is C$_1$-C$_3$ alkyl, particularly methyl. In any of the embodiments, in formula (IV), preferably j to n are independently 1, 2, or 3.

In accordance with an embodiment of the conjugate comprising a functionalized congener of an A$_3$ adenosine receptor agonist having a purine nucleoside moiety and a functional group at the N$^6$ position of the purine nucleoside moiety, wherein the functional group has the formula (III) or (IV), the functionalized congener has one of the following formulas (IIIa) and (IVa):

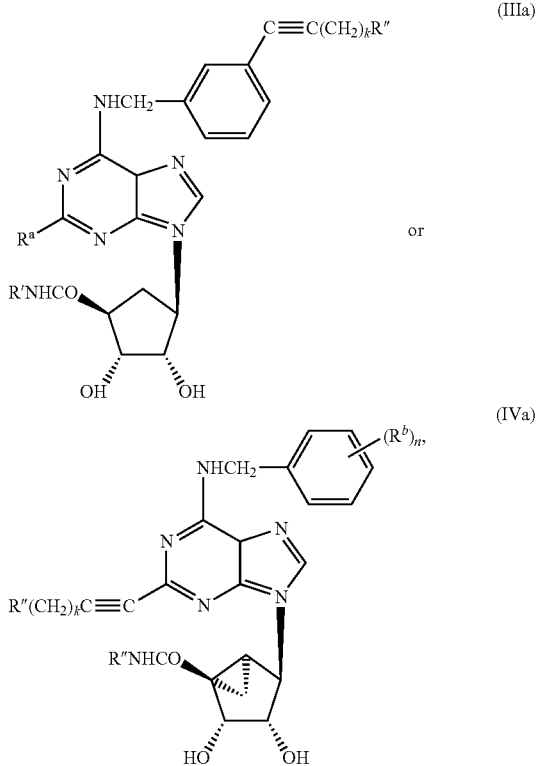

k = 1-4 wherein R' is C$_1$-C$_4$ alkyl and R" is NH$_2$ or COOH, wherein R' is C$_1$-C$_4$ alkyl; R" is NH$_2$ or COOH; R$^a$ is hydrogen or halo; and R$^b$ is a substituent selected from the group consisting of halo, amino, C$_1$-C$_6$ alkyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, aminocarbonyl C$_1$-C$_6$ alkoxy, and C$_6$-C$_{14}$ aryl C$_1$-C$_6$ alkoxy; or a group of the formula C≡C—(CH$_2$)$_m$—COR$^{11}$ wherein R$^{11}$ is selected from the group consisting of OH, OR$^{12}$, and NR$^{13}$R$^{14}$, wherein R$^{12}$ is selected from the group consisting of C$_1$-C$_6$ alkyl, C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ and diaryl C$_1$-C$_6$ alkyl; R$^{13}$ and R$^{14}$ are independently selected from the group consisting of hydrogen, C$_1$-C$_6$ alkyl, and (CH$_2$)$_m$R$^{15}$ wherein R$^{15}$ is NR$^{16}$R$^{17}$, wherein R$^{16}$ and R$^{17}$ are independently selected from the group consisting of hydrogen, C$_1$-C$_6$ alkyl, and COR$^{18}$ wherein R$^{18}$ is hydrogen or C$_1$-C$_6$ alkyl; wherein m is an integer from 1 to 10; and n is 1-3.

Specific examples of A$_3$ adenosine receptor agonists and dendrimer conjugates thereof are shown in FIG. 2 and a method of preparing such conjugates is illustrated in FIG. 3.

Examples of A$_1$, A$_{2A}$, A$_{2B}$, and/or A$_3$ adenosine receptor agonists can be found in the U.S. Provisional Patent Application No. 61/040,985, filed Mar. 31, 2008; WO 2006/031505 A$_1$ and WO 01/51490 A1, WO 2008/006369; WO 2006/128159; WO 2006/113204; U.S. Pat. Nos. 7,199,127; 7,087,589; 6,586,413; 6,376,521; 6,316,423; 6,211,165; 5,620,676; 5,284,834; 5,280,015; 5,840,728; 5,688,774; and 5,773,423; and US 2007/0232626 A$_1$ and US 2007/0265223 A1; the disclosures of which are incorporated by reference in their entireties.

In accordance with another embodiment, the invention provides a conjugate wherein the ligand is a functionalized congener of an A$_1$ adenosine receptor antagonist. Any suitable A$_1$ adenosine receptor antagonist can be part of the conjugate of the invention. An example of a suitable ligand of a functionalized congener of an A$_1$ adenosine receptor antagonist has the formula V:

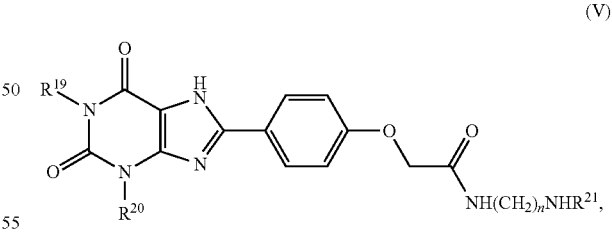

wherein R$^{19}$ and R$^{20}$ are independently C$_1$-C$_6$ alkyl; and R$^{21}$ is hydrogen or (CH$_2$)$_m$NH$_2$, wherein m and n are independently 1 to 6. In a preferred embodiment, R$^{19}$ and R$^{20}$ are n-propyl.

In accordance with another embodiment, the invention provides a conjugate wherein the ligand is a functionalized congener of an A$_{2A}$ adenosine receptor antagonist. Any suitable A$_{2A}$ adenosine receptor antagonist can be part of the conjugate of the invention. An example of a suitable ligand of a functionalized congener of an A$_{2A}$ adenosine receptor antagonist has the formula VI:

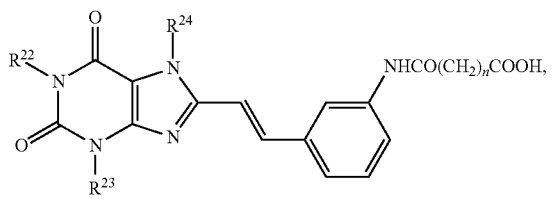

(VI)

wherein $R^{22}$ to $R^{24}$ are independently $C_1$-$C_6$ alkyl and n is 1 to 6, preferably $R^{22}$ to $R^{24}$ are methyl.

In accordance with another embodiment, the invention provides a conjugate wherein the ligand is a functionalized congener of an $A_{2B}$ adenosine receptor antagonist. Any suitable $A_{2B}$ adenosine receptor antagonist can be part of the conjugate of the invention. An example of a suitable ligand of a functionalized congener of an $A_{2B}$ adenosine receptor antagonist has the formula VII:

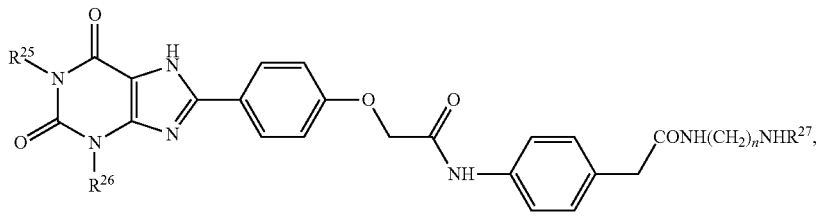

(VII)

wherein $R^{25}$ and $R^{26}$ are independently $C_1$-$C_6$ alkyl; and $R^{27}$ is hydrogen or $(CH_2)_m NH_2$, wherein m and n are independently 1 to 6, preferably $R^{25}$ and $R^{26}$ are n-propyl.

In accordance with another embodiment, the invention provides a conjugate wherein the ligand is a functionalized congener of an $A_3$ adenosine receptor antagonist. Any suitable $A_3$ adenosine receptor antagonist can be part of the conjugate of the invention. An example of a suitable ligand of a functionalized congener of an $A_3$ adenosine receptor antagonist has the formula VIII:

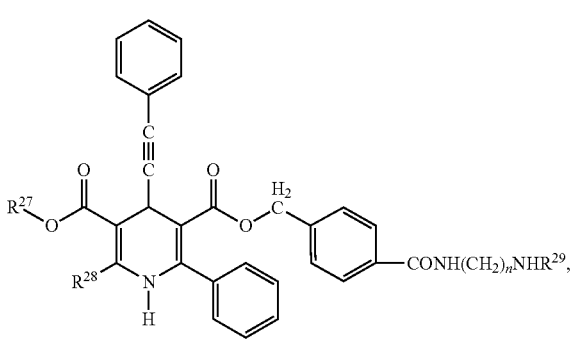

(VIII)

wherein $R^{27}$ and $R^{28}$ are independently $C_1$-$C_6$ alkyl; and $R^{29}$ is hydrogen or $(CH_2)_m NH_2$, wherein m and n are independently 1 to 6, preferably $R^{27}$ is ethyl and $R^{28}$ is methyl.

Examples of P2Y$_1$ receptor antagonists include adenosine 3',5'-bisphosphate (A3P5P) and the conformationally locked derivative which constrains the pseudosugar in the 2'-exo confirmation. See, e.g., Xu et al., J. Med. Chem. 2002, 45, 5694-5709. These antagonists can be functionalized to have amine or carboxyl groups which can be coupled to the dendrimer to prepare suitable conjugates in accordance with an embodiment of the invention.

Figure 48:
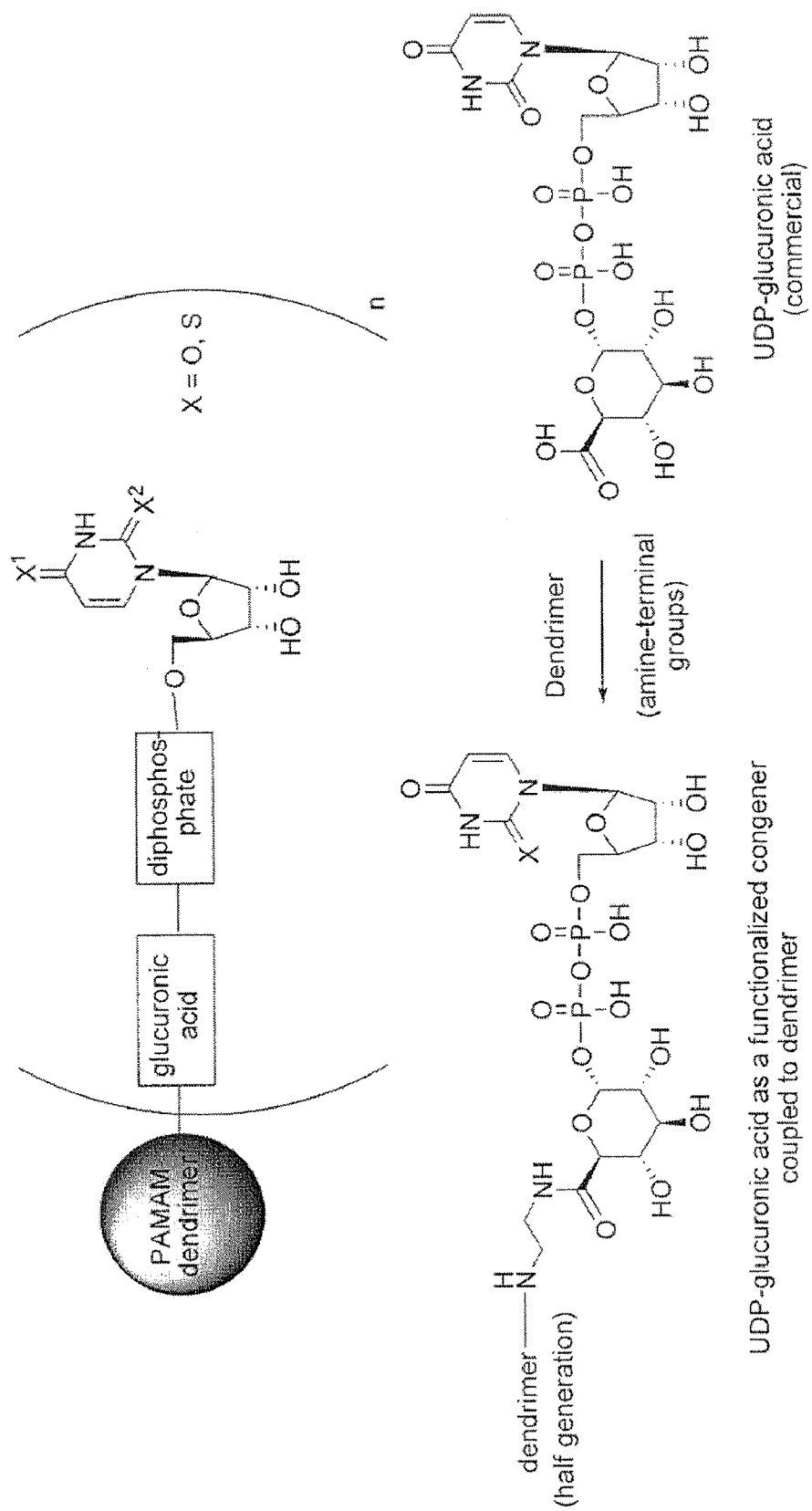
FIG. 48 depicts a formula of a dendrimer conjugate that includes a P2Y14 receptor agonist congener and a method of preparing such conjugate in accordance with an embodiment of the invention.

An example of a conjugate that includes a congener of the P2Y$_{14}$ receptor agonist is shown in FIG. 48, where n is 1 to any desired number as determined by the degree of loading. P2Y$_{14}$ receptors are activated by UDP-glucose (agonist). UDP-glucuronic acid is a suitable functionalized congener for coupling to amine functionalized dendrimers. These dendrimers are designed to activate the P2Y$_{14}$ receptor which is found in the immune, cardiovascular, and central nervous systems and are targeted for treating diseases treatable by activating the immune system, cardiovascular system, and the CNS.

Those skilled in the art can prepare the above-described functionalized congeners by any suitable method; see for example, Jacobson, K. A., Kirk, K. L., Padgett, W. L., Daly, J. W. Functionalized congeners of adenosine: preparation of analogues with high affinity for A$_1$-adenosine receptors; J. Med. Chem., 1985, 28:1341-1346; Jacobson, K. A., Kirk, K. L., Padgett, W. L., Daly, J. W. Functionalized congeners of 1,3-dialkylxanthines: preparation of analogues with high affinity for adenosine receptors. J. Med. Chem., 1985, 28:1334-1340 (also for A$_1$ AR antagonists); Jacobson, K. A., Kirk, K. L., Padgett, W. L., Daly, J. W. A functionalized congener approach to adenosine receptor antagonists: amino acid conjugates of 1,3-dipropylxanthine. Mol. Pharmacol., 1986, 29:126-133; Jacobson, K. A., Yamada, N., Kirk, K. L., Daly, J. W., Olsson, R. A. N$^6$-functionalized congeners of adenosine with high potency at A$_2$-adenosine receptors: potential ligands for affinity chromatography [erratum appears in Biochem. Biophys. Res. Commun., 1986, 139:375] Biochem. Biophys. Res. Commun. 1986, 136:1097-1102; Jacobson, K. A., Ukena, D., Padgett, W., Daly, J. W., Kirk, K. L. Xanthine functionalized congeners as potent ligands at A$_2$-adenosine receptors. J. Med. Chem., 1987, 30:211-214; Jacobson, K. A., Daly, J. W. Purine functionalized congeners as molecular probes for adenosine receptors. Nucleos. Nucleotid., 1991, 10:1029-1038.

In addition, see Jacobson, K. A., Gallo-Rodriguez, C., Melman, N, Fischer, B., Mailard, M., van Bergen, A., van Galen, P. J. M., Karton, Y., Structure-Activity relationships of 8-styrylxanthines as A$_2$-selective adenosine antagonists; J. Med. Chem., 1993, 36: 1333-1342; Kim, Y. C., et al., Anilide derivatives of an 8-phenylxanthine carboxylic congener are highly potent and selective antagonists at human A$_{2B}$ adenosine receptors., J. Med. Chem., 2000, 43: 1165-1172; Li, A.-H., et al., Functionalized congeners of 1,4-dihydropyridines as antagonist molecular probes for A$_3$ adenosine receptors. Bioconj. Chem., 1999, 10:667-677; and Karton, Y., et al., Molecular probes for muscarinic receptors: Derivatives of the M$_1$-antagonist telenzepine, Bioconj. Chem., 1992, 3:234-240; see also U.S. Pat. No. 5,324,832, which teaches substitution of the distal N-methyl group of pirenzepine or telenzepine. Such substituted derivatives can be functionalized and covalently linked to dendrimer molecules to produce conjugates in accordance with an embodiment of the invention.

For PEG conjugates of drugs and methods of preparing such conjugates, see Poly(ethylene glycol) Conjugated Drugs and Prodrugs: A Comprehensive Review; Greenwald, R. B., et al., *Critical Reviews in Therapeutic Drug Carrier Systems*, 17(2): 101-161 (2000).

The conjugates of the invention can optionally include one more surface modifying moieties to modify one or more of the surface properties of the conjugate or a group that protects the surface functional groups such as amine or carboxylic functional groups. Thus, for example, the surface modifying moiety can be an amine protecting group. An example of an amine protecting group is $C_1$-$C_6$ alkyl carbonyl, preferably $C_1$-$C_3$ alkyl carbonyl, wherein the alkyl group is unsubstituted or substituted with a substituent selected from the group consisting of $C_1$-$C_6$ alkoxy, hydroxy, halo, nitro, cyano, amino, amido, and mercapto.

In accordance with an embodiment, the surface modifying moiety comprises a hydrophilic group, e.g., a polyethylene glycol moiety. The polyethylene glycol moiety can be linked to the dendrimer through any suitable bond, e.g., amide, hydrazide, ether, urethane, urea, thiourea, ester, carbonate, carbamate, hydrazone, carbazone, secondary amine, tertiary amine, and quaternary amine.

In any of the embodiments of the invention, the conjugate can include covalently bonded agonists or antagonists of at least two or three, or four different receptors, for example, agonists of $A_1$ and $A_{2A}$, of $A_1$ and $A_{2B}$, of $A_1$ and $A_3$, of $A_{2A}$ and $A_3$, of $A_1$, $A_{2A}$, and $A_3$, of $A_1$, $A_{2B}$, and $A_3$, and so, or $A_1$, $A_{2A}$, $A_{2B}$, and $A_3$ adenosine receptor antagonists or $P2Y_1$ antagonists, or $M_1$ muscarinic antagonists, on the same dendrimer molecule. It is contemplated that such conjugates having multiple agonists, antagonists, or agonists and antagonists, would advantageously activate or block organs or tissues where different types of receptors are found in close proximity to one another. Alternatively, or in addition, the conjugate can contain at least two or three, or four different agonists or antagonists of the same type of receptor.

Thus, for example, the conjugate can include a $P2Y_1$ receptor antagonist and an $A_3$ adenosine receptor agonist or a $P2Y_1$ receptor agonist and an $A_3$ adenosine receptor antagonist. As a further example, it is contemplated that a conjugate having a combination of $A_{2A}$ agonist and $P2Y_1$ antagonist could provide highly potent inhibitors of platelet aggregation. In addition, it is contemplated that a conjugate containing $A_1$ and $A_3$ adenosine receptor agonists could be effective against cardiac ischemia; a conjugate having the combination of $A_1$ and $A_{2A}$ adenosine receptor antagonists could be effective against Parkinson's disease and a conjugate having a combination of $A_{2B}$ and $A_3$ adenosine receptor antagonists could be effective against asthma. It is expected that a balanced modulation of multiple targets (polypharmacy) can provide a superior therapeutic effect and side effect profile relative to the action of a single ligand.

Selectivity of any type of agonist or antagonist can be advantageously increased by a careful selection of agonists and/or antagonists that are to be present on the conjugate. Heterodimers are particularly preferred. It is expected that pharmacology would be significantly affected by the type of agonist and antagonist present on the same conjugate.

In accordance with an embodiment, when two or more adenosine receptor agonists are present in the conjugate, the agonists could be, for example, in the form of a binary conjugate, i.e., the two or three agonists are covalently linked together; see, e.g., Jacobson, K. A., et al., A Novel Pharmacological Approach to Treating Cardiac ischemia, *J. Biol. Chem.*, 275, 39, 30272-279 (2000).

The conjugate of the invention can contain any suitable degree of loading of the agonist or antagonist or both, e.g., a degree of loading greater than about 0.1%, about 10%, about 20%, about 30%, about 40%, about 50%, about 60%, about 70%, about 80%, about 90%, or more; or 100% or less, about 95% or less, about 85% or less, about 75% or less, about 65% or less, about 55% or less, about 45% or less, about 35% or less, about 25% or less, about 15% or less, or about 5% or less, for example, about 1% to about 99%, about 10% to about 90%, about 20% to about 80%, about 30% to about 70%, or about 40% to about 60%, of the theoretical capacity of the dendrimer.

In accordance with an embodiment, the conjugate of the invention can optionally include a covalently bonded marker, e.g., a dye or a fluorescent marker.

The present invention further provides a pharmaceutical composition comprising a conjugate of the invention and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the conjugates of the present invention.

The conjugates can be in the form of salts also. Examples of pharmaceutically acceptable salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic, for example, benzenesulfonic and p-toluenesulfonic, acids.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; the conjugates of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The conjugates of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The conjugate can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the conjugate in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The conjugates of the present invention may be made into injectable formulations. The requirements for effective pharmaceutical carriers for injectable compositions are well known to those of ordinary skill in the art. See *Pharmaceutics and Pharmacy Practice*, J. B. Lippincoft Co., Philadelphia, Pa., Banker and Chalmers, eds., pages 238-250 (1982), and *ASHP Handbook on Injectable Drugs*, Toissel, 4th ed., pages 622-630 (1986).

Additionally, the conjugates of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The present invention further provides a method of treating a disease or condition which is treatable by agonizing (or activating) or antagonizing (or blocking) a receptor of the GPCR superfamily in a mammal comprising administering to the mammal an effective amount of a conjugate of the invention. For example, diseases treatable by an $A_{2A}$ adenosine receptor agonists include sleep disorders, respiratory disorders, reperfusion injury, thrombosis, hypertension, kidney ischemia, rheumatoid arthritis, inflammation, wound healing, sepsis, and sepsis syndrome, diseases treatable by an $A_1$ adenosine receptor agonists include stroke, epilepsy, migraine, pain, cardiac ischemia, and arrhythmia, diseases treatable by an $A_3$ adenosine receptor agonists include stroke, lung injury, cardiac ischemia, skeletal muscle ischemia, and cancer, and diseases treatable by an $A_{2B}$ adenosine receptor agonists asthma, diabetes, diarrhea, septic shock, cystic fibrosis, restenosis, erectile dysfunction, inflammation, and cardiac ischemia.

Examples of diseases treatable by $A_1$ adenosine receptor antagonists include those selected from the group consisting of a cognitive disease, renal failure, and cardiac arrhythmia. Examples of diseases treatable by $A_{2A}$ adenosine receptor antagonists include diseases selected from the group consisting of Parkinson's disease, hepatic fibrosis, hepatic cirrhosis, and fatty liver. Examples of diseases treatable by $A_{2B}$ adenosine receptor antagonists include diseases selected from the group consisting of arthritis, asthma, multiple sclerosis, endotoxic shock, gram negative shock, toxic shock, hemorrhagic shock, cachexia secondary to cancer, osteoporosis, infertility from endometriosis, and bacterial meningitis. Examples of diseases treatable by $A_3$ adenosine receptor antagonists include eye disease such as glaucoma, and tumor; thus, the treatment involves reducing intraocular pressure or inhibiting tumor growth. $P2Y_1$ receptor antagonists are useful, for example, in treating or preventing thrombosis. Examples of diseases treatable by $M_1$ muscarinic antagonists include those of the higher cognitive function such as memory loss and Alzheimer's disease.

For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human.

The present invention also provides a diagnostic method for determining a treatment of a patient for a possible adenosine receptor agonist or antagonist treatment comprising:

(a) administering a conjugate comprising a dendrimer, at least one ligand covalently linked to the dendrimer, a fluorescent marker covalently linked to the dendrimer, and optionally one or more surface modifying moieties covalently linked to the dendrimer, wherein the ligand is a functionalized congener of an agonist or antagonist of a receptor of the G-protein coupled receptor (GPCR) superfamily;

(b) obtaining a biological sample from the patient;

(c) determining the level of expression of at least one receptor;

(d) comparing the level of expression of the receptor to that of a normal population; and (e) if the patient's level of expression is higher or lower than that of the normal population, determining a treatment regimen comprising administering an agonist or antagonist of the receptor whose expression was higher or lower in the patient than that of the normal population.

Thus, for example, a diagnostic test can be provided for a suspected cancer patient. An $A_3$ adenosine receptor agonist can be administered and after a suitable period of time, e.g., 30 min., a sample, e.g., blood, can be taken from the patient and the neutrophils isolated. If an elevated level of $A_3$ receptor is found in the neutrophils relative to that of a normal population, it can be determined that an $A_3$ adenosine receptor agonist treatment can be initiated. In accordance with embodiments of the invention, the sample can be any suitable sample such as blood, plasma, serum, swabs, washes, sputum, cell- and tissue-samples or biopsies. In accordance with embodiments of the invention, any of the diseases amenable to treatment by any one of the $A_1$, $A_{2A}$, $A_{2B}$, or $A_3$ adenosine receptor agonists or antagonists or $P2Y_1$ receptor agonist or antagonists or the $M_1$ muscarinic antagonists described above can be detected and treated.

The following examples further illustrate the invention but, of course, should not be construed as in any way limiting its scope.

EXAMPLE 1

This example demonstrates the preparation and properties of dendrimer conjugates comprising $A_{2A}$ adenosine receptor agonists in accordance with an embodiment of the invention.
Experimental Procedures Materials and Methods. Glass wares were oven-dried and cooled in a desiccator before use. All reactions were carried out under a dry nitrogen atmosphere. Solvents were purchased as anhydrous grade and used without further purification. Suppliers of the commercial compounds are listed as follows: PAMAM dendrimers of G2.5, G3, G3.5, and G5.5 with the ethylenediamine core, poly(ethylene glycol) methyl ether ($M_n$, 550, 750, and 2,000), acetic anhydride ($Ac_2O$), 4-nitrophenyl chloroformate, monomethyl succinate, N-acetylethylenediamine, N-tert-butoxycarbonyl (Boc) ethylenediamine, triethylamine, trifluoroacetic acid (TFA), N,N-diisopropylethylamine (DIEA), dimethyl sulfoxide (DMSO), acetonitrile ($CH_3CN$), methanol (MeOH), chloroform ($CHCl_3$), and isopropanol were purchased from Aldrich; N,N-dimethylformamide (DMF) and tetrahydrofuran (THF) were purchased from Acros; (benzotriazol-1-yloxy)tripyrrolidinophosphonium hexafluorophosphate (PyBOP) was purchased from NovaBiochem; 2-[4-(2-carboxyethyl)phenylethylamino]-5'-N-ethylcarboxamidoadenosine (CGS21680) hydrochloride was purchased from Tocris; acetic acid N-hydroxysuccinimide ester (AcOSu) was purchased from Research Organics; DMSO-d6, chloroform-d (CDCl3), and deuterium oxide (D2O) were purchased from Cambridge Isotope Laboratories; single isomers of 5-carboxyfluorescein succinimidyl ester and Alexa Fluor 4885-carboxylic acid 2,3,5,6-tetrafluorophenyl (TFP) ester were purchased from Invitrogen. 2-[4-(2-aminoethylaminocarbonylethyl)phenylethylamino]-5'-N-ethylcarboxamidoadenosine (APEC) bistrifluoroacetic acid was provided by NIMH Chemical Synthesis and Drug Supply Program.

Thin layer chromatography (TLC) was performed on 0.2 mm silica glass coated sheets (E. Merck) with F-254 indicator. Visualization of the products on TLC plate was performed by UV light. Flash column chromatography was performed on Merck 40-63 μm silica gel. Preparative size exclusion chromatography (SEC) was performed on Bio-Beads S-X1 beads (BIO-RAD), 200-400 mesh, with DMF (Aldrich 99.8%, anhydrous) as an eluent at 1 atm.

Figure 4A:
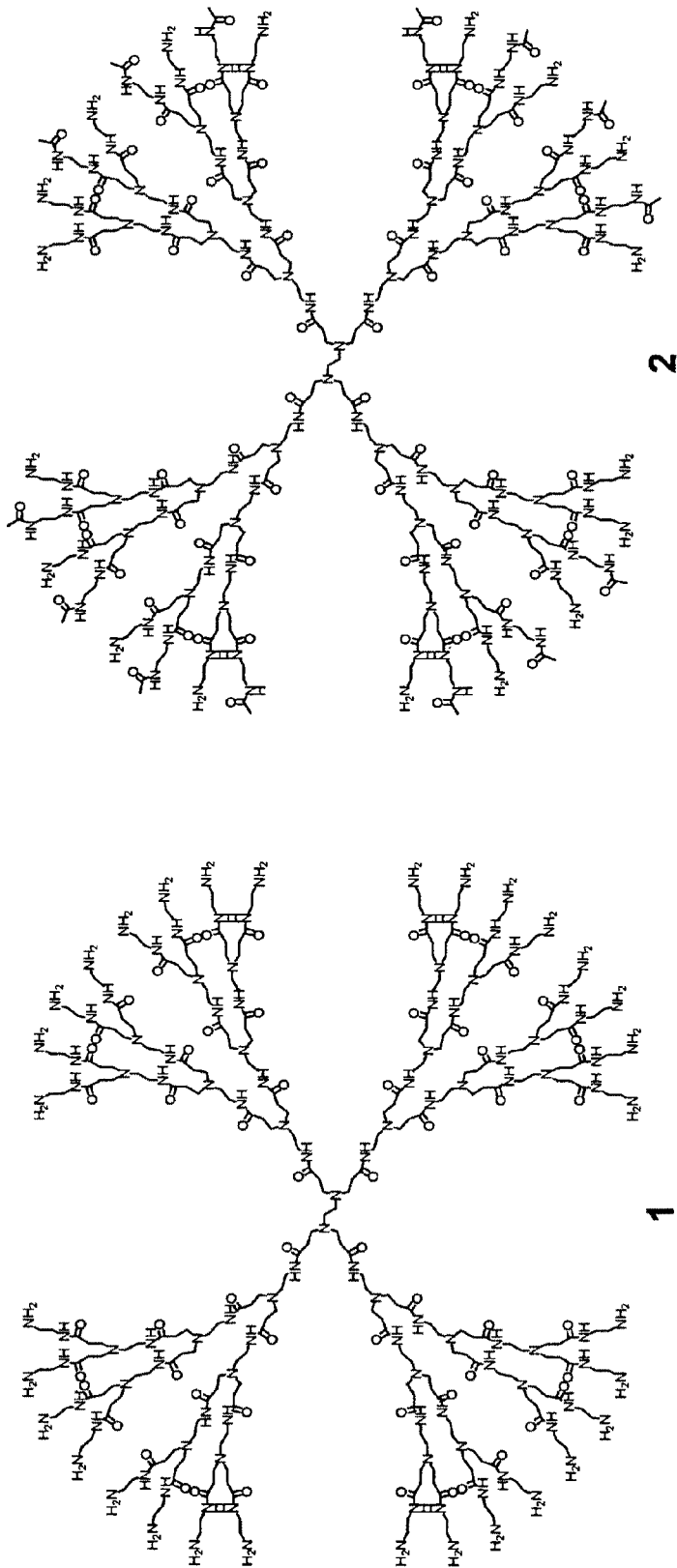
FIG. 4A depicts the structures of two PAMAM G3 dendrimers with varying degrees of acetylation: 0 acetyl for 1, and 14 acetyl for 2, in accordance with an embodiment of the invention.
Figure 4B:
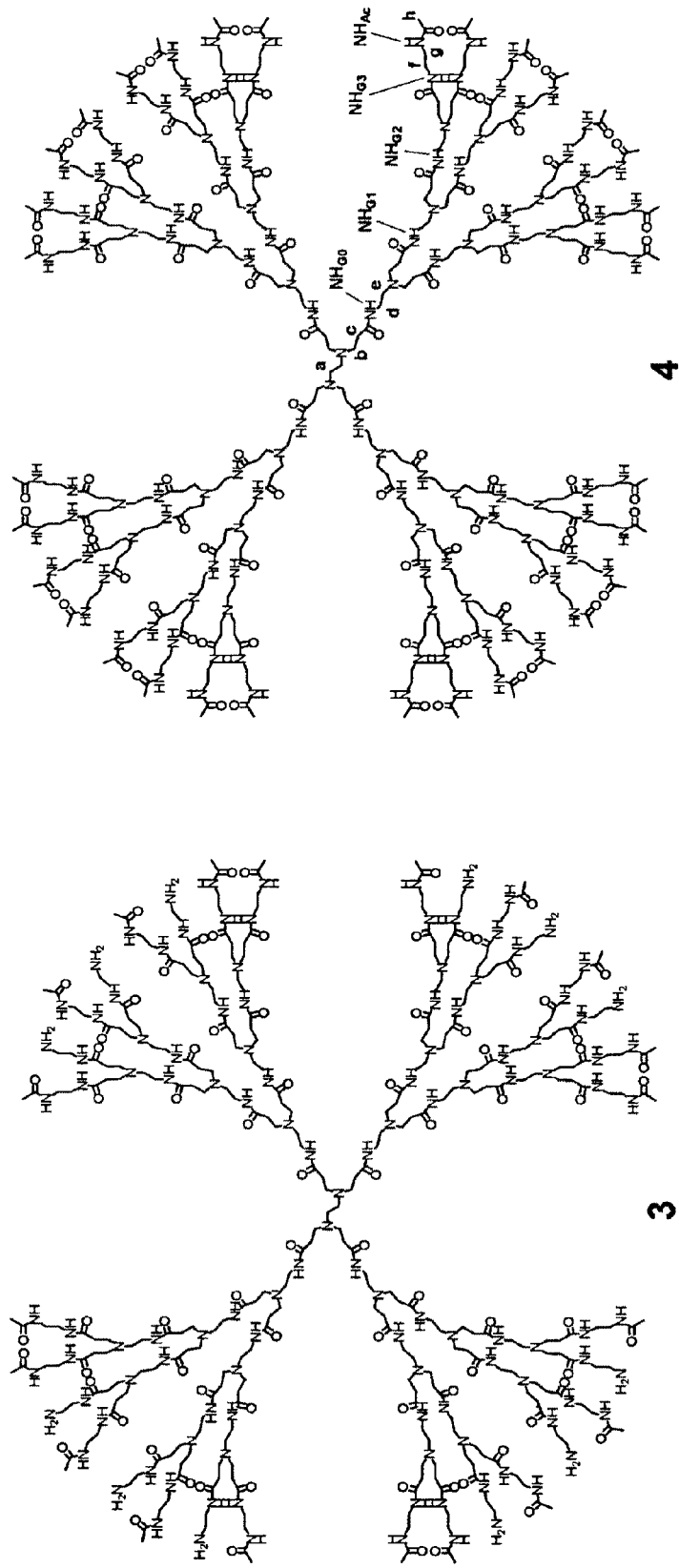
FIG. 4B depicts the structures of two other PAMAM G3 dendrimers with varying degrees of acetylation: 20 acetyl for 3, and 32 acetyl for 4, in accordance with an embodiment of the invention.
Figure 5:
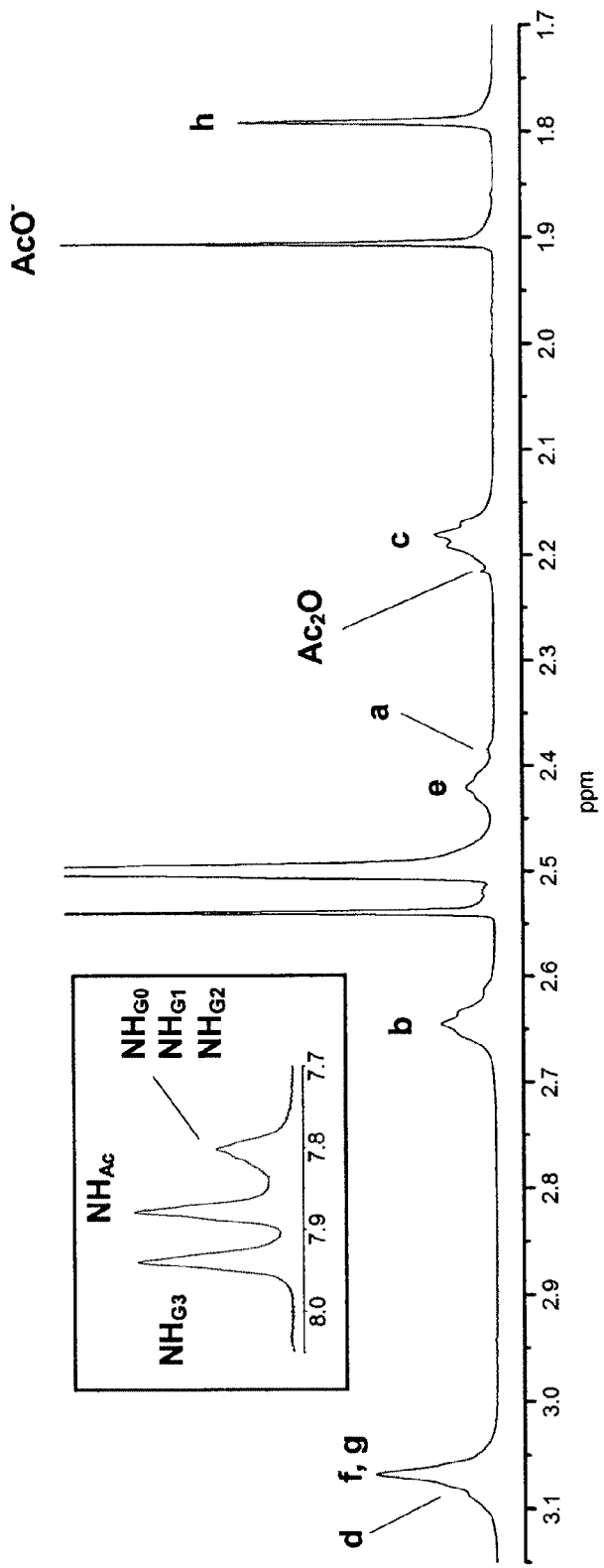
FIG. 5 depicts the 1H NMR spectrum of 4, a PAMAM G3 treated with excess of acetic anhydride, in DMSO-d6. The reaction mixture contains a small amount of DMSO.

Nuclear magnetic resonance (NMR) spectra were recorded on a Bruker DRX-600 spectrometer at 25.0° C., unless otherwise mentioned. $^1H$ NMR chemical shifts were measured relative to the residual solvent peak at 7.26 ppm in $CDCl_3$, at 2.50 ppm in DMSO-$d_6$, and at 4.80 ppm in water-$d_2$ ($D_2O$) $^{13}C$ NMR chemical shifts were measured relative to the residual solvent peak at 77.23 ppm in $CDCl_3$, and at 39.51 ppm in DMSO-$d_6$. Complete NMR peak assignments were made possible with 2D COSY and NOESY experiments. For dendrimer conjugates, only the peaks clearly resolved in the $^1H$ NMR spectra were listed, and the integration values of each peak were reported as determined in the $^1H$ NMR analysis. For dendrimer-ligand conjugates, a peak at 2.18 ppm corresponding to "c" (4, FIG. 4) was used as an internal standard (120 H) for PAMAM G3 dendrimer, and the relative integration value of a —$CH_3$ peak (0.95-0.96 ppm) from the adenosine moiety of each ligand (i.e., APEC and CGS21680) was determined to establish the number of ligand attachments. The acetamide peak at 1.78-1.79 ppm was used as an internal standard instead for integration (see text for details), if available.

The electrospray ionization mass spectrometry (ESI MS) experiments were performed on an API 100 Perkin Elmer SCIEX single quadrupole mass spectrometer. Matrix-assisted laser desorption ionization time-of-flight (MALDI-TOF) MS experiments were performed on a PerSeptive Biosystems Voyager DE-STR spectrometer at the Mass Spectrometry Laboratory, University of Illinois.

General Procedure for Acetylation of PAMAM G3 Dendrimer. Method A: Dendrimer conjugates were synthesized from the PAMAM G3 dendrimer 1 (FIG. 4) containing an ethylenediamine core and ca. 32 amino end groups. To a DMSO-$d_6$ solution of PAMAM G3 1 was added slowly the corresponding amount of $Ac_2O$ as a DMSO-$d_6$ solution with stirring. Reaction was continued to stir for 24 h under a nitrogen atmosphere. $^1H$ NMR of the reaction mixture was measured to establish the degree of acetylation by integration. Method B: To a DMSO-$d_6$ solution of PAMAM G3 conjugates was added triethylamine (or DIEA, 1.5 equiv per primary amine of PAMAM G3 derivative), followed by a slow addition of the corresponding amount of AcOSu as a DMSO-$d_6$ solution with stirring. Reaction was continued to stir for 24 h under a nitrogen atmosphere. The mixture was loaded directly to a SEC column in DMF, to isolate the desired dendrimer conjugate. $^1H$ NMR was measured in DMSO-$d_6$ to establish the degree of acetylation on the PAMAM dendrimer by the integration method.

μmol) were dissolved in a mixture of 1:1 $CH_3CN$/isopropanol (5 mL), and then triethylamine (100 μL, 718 μmol) was added to this mixture. Reaction was stirred for 2 h at room temperature, solvent was removed in vacuo, and the crude product was purified by a preparative TLC (4:1 $CHCl_3$/MeOH) to give 41.4 mg (56.4 μmol, 80%) of 6 as a white solid. Prolonged reaction time increased the amounts of side-products. $R_f$: 0.40 [silica gel, 4:1 $CHCl_3$/MeOH]; $^1H$ NMR (600 MHz, DMSO-$d_6$) δ 9.80 (br s, 1H, $H_{12}$), 8.04 (br s, 1H, $H_{15}$), 8.02 (s, 1H, $H_{8Ad}$), 8.00 (s, 1H, $H_8$), 7.92 (s, 1H, $H_{11}$), 7.53 (d, 2H, J=7.5 Hz, $H_{14}$), 7.37 (d, 2H, J=7.4 Hz, $H_{13}$), 7.15 (d, 2H, J=8.3 Hz, $H_4$/$H_5$), 7.11 (d, 2H, J=7.8 Hz, $H_4$/$H_5$), 6.79 (br s, 2H, $H_{6Ad}$), 6.20 (t, 1H, J=5.2 Hz, $H_1$), 5.84 (d, 1H, J=7.6 Hz, $H_{1'}$), 5.58 (d, 1H, J=4.6 Hz, $H_{3'-OH}$), 5.50 (d, 1H, J=6.2 Hz, $H_{2'-OH}$), 4.72 (dd, 1H, J=11.0, 6.0 Hz, $H_{2'}$), 4.25 (d, 1H, J=2.4 Hz, $H_{4'}$), 4.18 (m, 1H, $H_{3'}$), 3.52 (m, 2H, $H_{10}$), 3.49-3.34 (m, 2H, $H_2$), 3.25 (q, 2H, J=6.1 Hz, $H_9$), 3.20-3.03 (m, 2H, $H_{16}$), 2.77 (m, 4H,

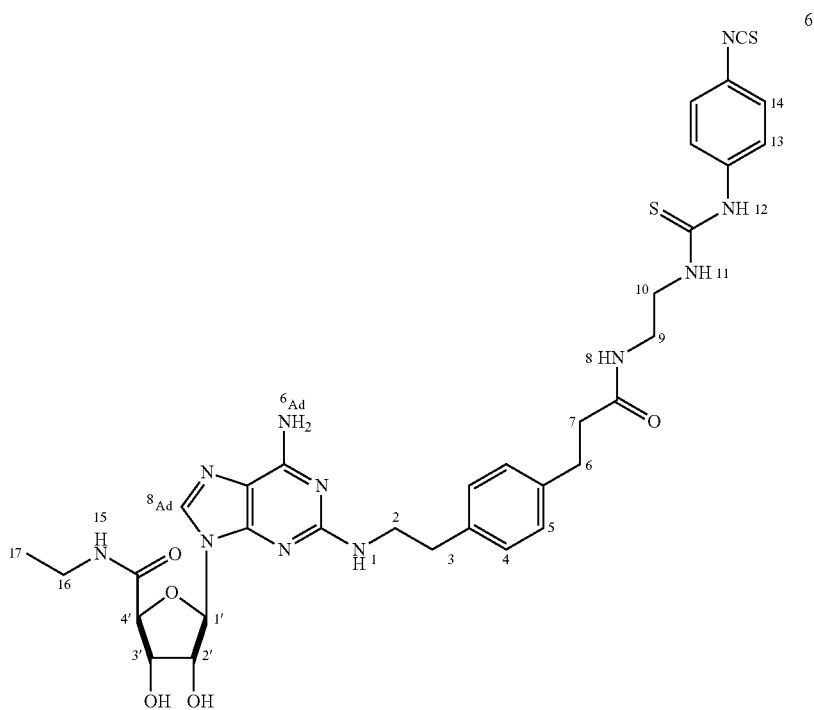

Figure 6:
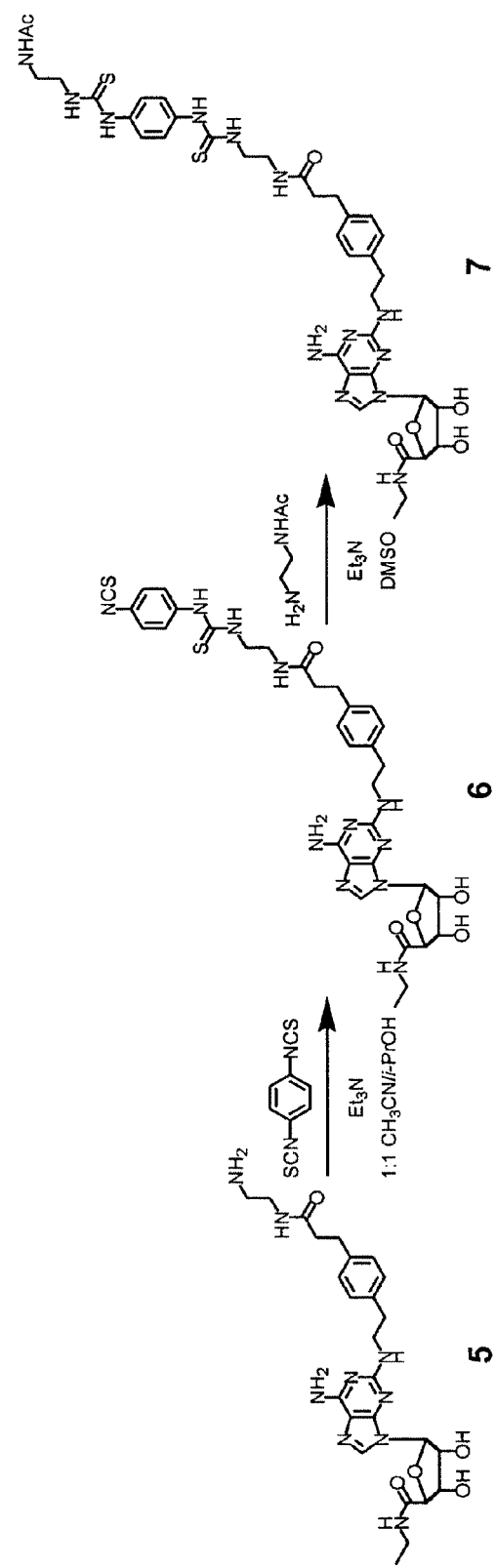
FIG. 6 depicts Scheme 1, a reaction scheme to prepare an adenosine receptor agonist congener, 7, in accordance with an embodiment of the invention.

DITC-APEC 6 (FIG. 6). APEC 5 (54.0 mg, 70.2 μmol, as a 2 TFA salt) and diisothiocyanatobenzene (40.0 mg, 208

$H_3$ and $H_6$), 2.36 (t, 2H, J=7.8 Hz, $H_7$), 0.97 (t, 3H, J=7.1 Hz, $H_{17}$); HRMS (ESI) Calcd for $C_{33}H_{10}N_{11}O_5S_2$ ($M+H^+$): 734.2655, Found: 734.2674.

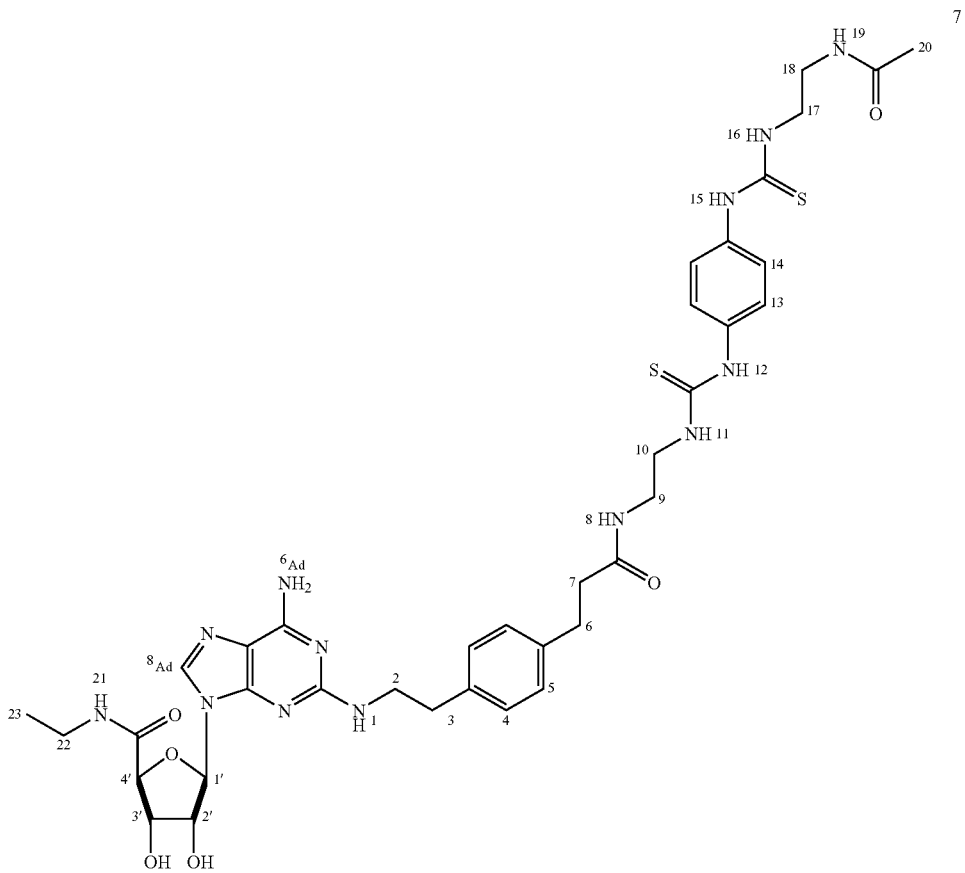

DITC-APEC Analogue 7 (Monomeric Control, FIG. 6). DITC-APEC 6 (5.26 mg, 7.17 μmol) was dissolved in DMSO-$d_6$ (300 μL), and triethylamine (20 mL, 144 μmol) was added to this mixture. N-Acetylethylenediamine (2.00 μL, 18.8 μL, 90% tech.) was added to this stirred solution. The reaction was continued to stir at room temperature for 16 h. Solvent was removed in vacuo, and the crude product was purified by a preparative TLC (5:2 CHCl$_3$/MeOH) to give 0.89 mg (1.56 μmol, 22%) of 7 as a white solid. Low yield of this reaction is possibly due to the highly polar nature of the desired compound 7, which was difficult to recover completely from the preparative TLC plate under acceptable conditions. $R_f$: 0.25 [silica gel, 4:1 CHCl$_3$/MeOH]; $^1$H NMR (600 MHz, DMSO-$d_6$) δ 9.58 (br s, 2H, $H_{12}$ and $H_{15}$), 8.04 (br s, 1H, $H_{21}$), 8.02 (s, 1H, $H_{8Ad}$), 8.00 (s, 1H, $H_8$), 7.983, (s, 1H, $H_8/H_{19}$), 7.975 (s, 1H, $H_8/H_{19}$), 7.67 (br s, 2H, $H_{11}$ and $H_{16}$), 7.32 (s, 4H, $H_{13}$ and $H_{14}$), 7.16 (d, 2H, J=8.1 Hz, $H_4/H_5$), 7.11 (d, 2H, J=7.9 Hz, $H_4/H_5$), 6.80 (br s, 2H, $H_{6Ad}$), 6.20 (t, 1H, J=5.3 Hz, $H_1$), 5.84 (d, 1H, J=6.8 Hz, $H_{1'}$), 5.58 (d, 1H, J=4.7 Hz, $H_{3'-OH}$), 5.50 (d, 1H, J=6.2 Hz, $H_{2'-OH}$), 4.72 (dd, 1H, J=11.3, 6.1 Hz, $H_{2'}$), 4.25 (d, 1H, J=2.0 Hz, $H_{4'}$), 4.18 (m, 1H, $H_{3'}$), 3.51 (m, 4H, $H_{10}$ and $H_{17}$), 3.49-3.34 (m, 2H, $H_2$), 3.23 (m, 4H, $H_9$ and $H_{18}$), 3.20-3.03 (m, 2H, $H_{22}$), 2.77 (m, 4H, $H_3$ and $H_6$), 2.35 (t, 2H, J=8.0 Hz, $H_7$), 1.80 (s, 3H, $H_{20}$), 0.97 (t, 3H, J=7.0 Hz, $H_{23}$); HRMS (ESI) Calcd for $C_{37}H_{50}N_{13}O_6S_2$ (M+H$^+$): 836.3448, Found: 836.3440.

General Procedure for Conjugation of Fluorescein to the PAMAM G3 Derivatives. To a known concentration of PAMAM G3 derivative in DMSO-$d_6$ was added triethylamine (or DIEA, 1.5 equiv per primary amine of PAMAM G3 derivative), followed by a slow addition of 5-carboxyfluorescein succinimidyl ester 11 (1.0 equiv per dendrimer) as a DMSO-$d_6$ solution with stirring. Reaction was stirred for 36-48 h at room temperature protected from light. $^1$H NMR was measured, and the crude reaction mixture was used to continue to the next step without any further purification.

General Procedure for Conjugation of APEC to the PAMAM G3 Derivatives. The isothiocyanate 6 was dissolved in DMSO (or DMSO-$d_6$) to make a stock solution of ca. 30 mM. The corresponding amount of 6 in DMSO (or DMSO-$d_6$) was added to the solution of PAMAM G3 derivative in DMSO (or DMSO-$d_6$). If the previous reaction did not involve the usage of base, triethylamine (or DIEA, 1.5 equiv per primary amine of PAMAM G3 derivative) was added to the mixture. The reaction was stirred at room temperature for 48 h. The crude mixture in DMSO (or DMSO-$d_6$) was loaded directly on a SEC column in DMF for purification. Column fractions exhibiting fluorescence were combined together and concentrated in vacuo. If the previous steps did not involve the attachment of fluorescent groups, fractions were monitored by a UV light at 254 nm to combine the fractions corresponding to the first UV-active band (i.e., the highest MW with a similar retention time as the fluorescent dendrimer analogue). $^1$H NMR was measured in DMSO-$d_6$ to establish the average number of APEC groups on the PAMAM dendrimer by the integration method. The compound was dried extensively in vacuo for >5 d to remove the solvents. The yield calculated based on the NMR-determined MW was nearly quantitative.

Figure 7A:
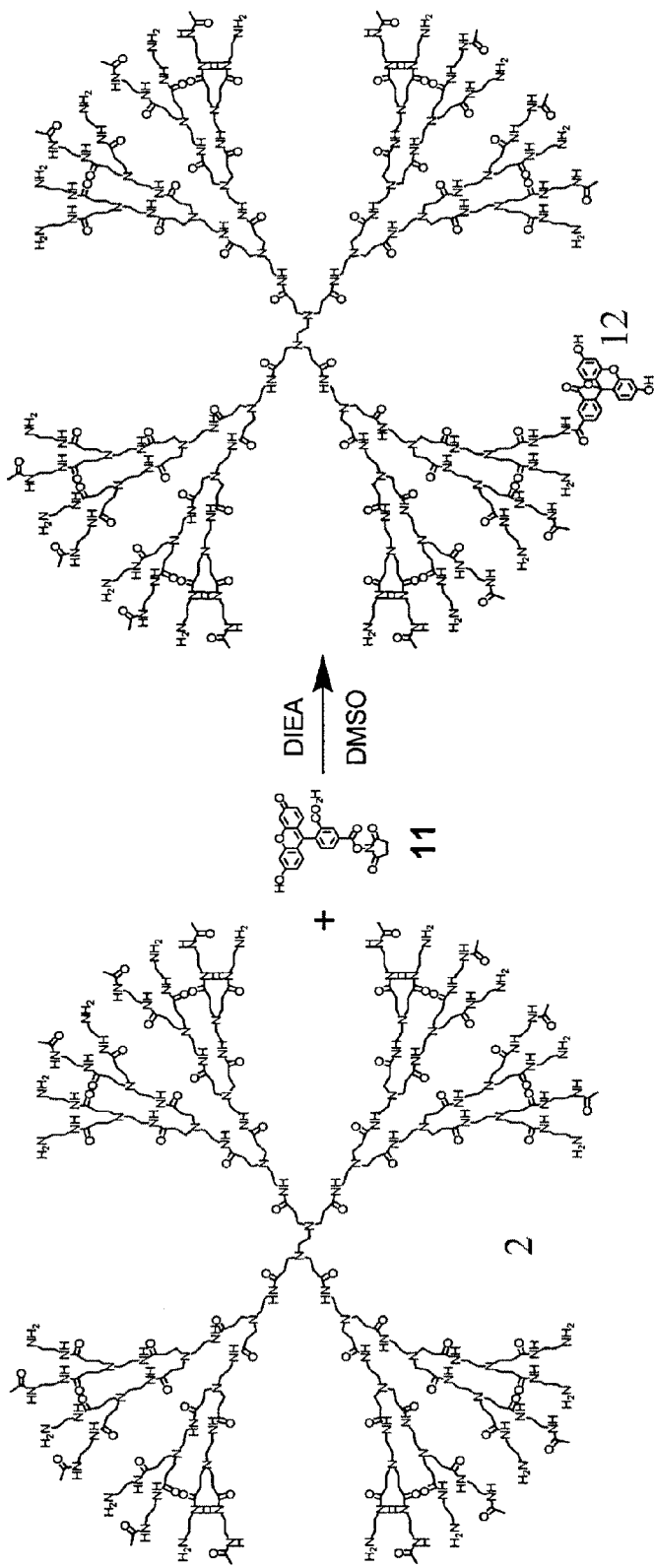
FIG. 7A depicts the first part of Scheme 2, a reaction scheme to prepare a dendrimer conjugate 8, in accordance with an embodiment of the invention.
Figure 7B:
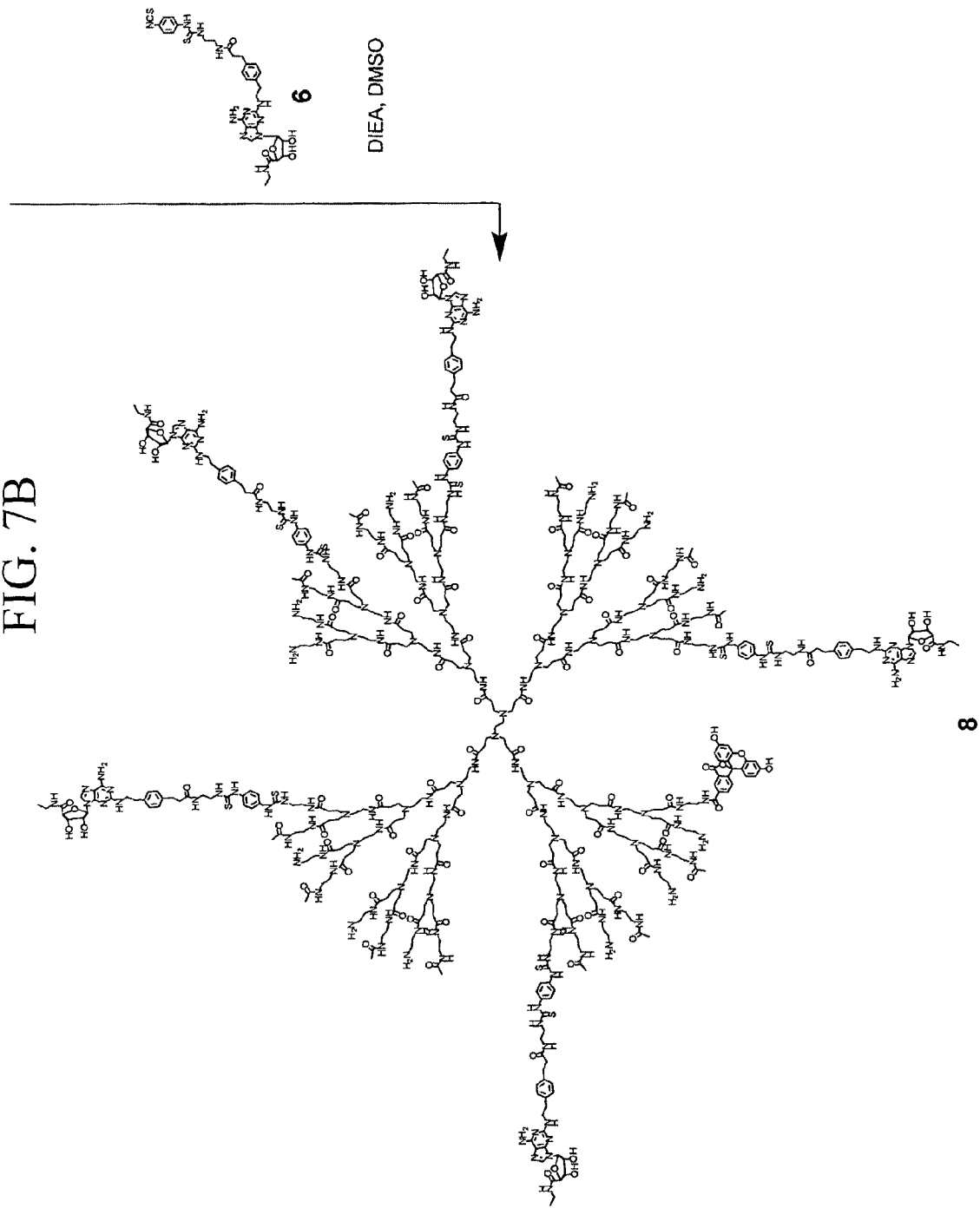
FIG. 7B depicts the second part of Scheme 2.

PAMAM-APEC Conjugate 8 (FIG. 7) A ca. 2.39 mM solution of 2 in DMSO (560 μL, 1.34 μmol) was diluted with DMSO (240 μL), and to this stirred mixture was added DIEA (10.0 µL, 57.4 µmol), followed by a slow addition of a 6.51 mM solution of 5-carboxyfluorescein succinimidyl ester 11 in DMSO (200 µL, 1.30 µmol). The reaction was stirred for 48 h at room temperature, protected from light to make 12. A portion of this crude solution of 12 (480 µL, 0.643 µmol, ca. 1.34 mM) was transferred into another flask, and a 44.1 mM solution of DITC-APEC 6 in DMSO (130 µL, 5.73 µmol) was slowly added to this stirred mixture. The reaction was stirred for 5 d protected from light, purified by SEC (H 36.5 cm×O.D. 4.5 cm) in DMF, and dried in vacuo to give 8 as an orange glassy solid. $^1$H NMR (600 MHz, DMSO-d$_6$) δ 7.36, 7.32 (br s (each), 17.74H, H$_{13}$ and H$_{14}$), 7.14, 7.11 (d (each), 19.74H, H$_4$ and H$_5$), 6.80 (br s, 8.58H, H$_{6Ad}$), 6.20 (s, 4.58H, H$_1$), 5.84 (d, 4.59H, J=6.2 Hz, H$_{1'}$), 4.72 (m, 4.19H, H$_{2'}$), 4.26 (s, 5.23H, H$_{4'}$), 4.19 (s, 4.65H, H$_{3'}$), 3.07 (s, 134.80H, H$_d$, H$_f$, H$_{f'}$, and H$_g$), 2.77 (m, 24.56H, H$_3$ and H$_6$), 2.64 (m, 115.44H, H$_b$ and H$_{g'}$), 2.42 (m, 49.60H, H$_e$), 2.35 (m, 17.88H, H$_7$), 2.18 (m, 109.61H, H$_c$), 1.79 (s, 40.66H, H$_h$), 0.97 (t, 14.62H, J=6.7 Hz, H$_{18}$).

Figure 8A:
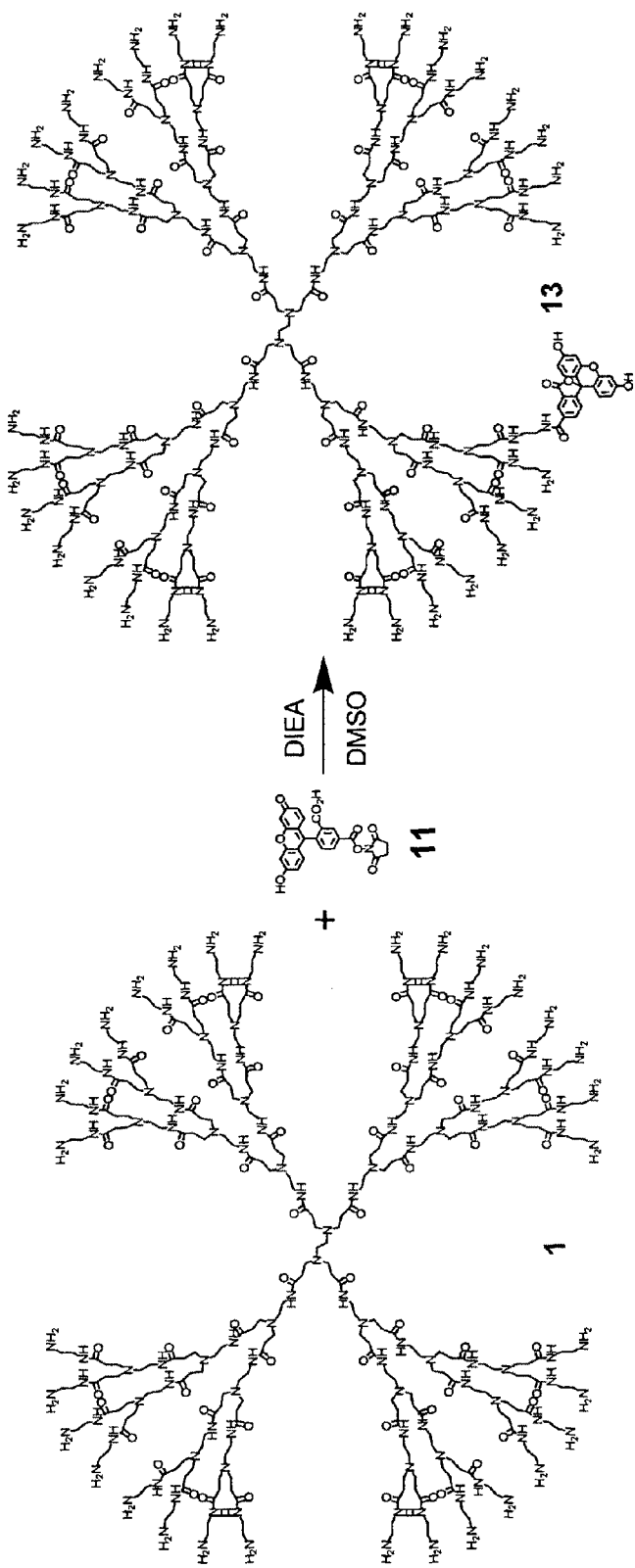
FIG. 8A depicts the first part of Scheme 3, a reaction scheme to prepare a dendrimer conjugate 9, in accordance with an embodiment of the invention.
Figure 8B:
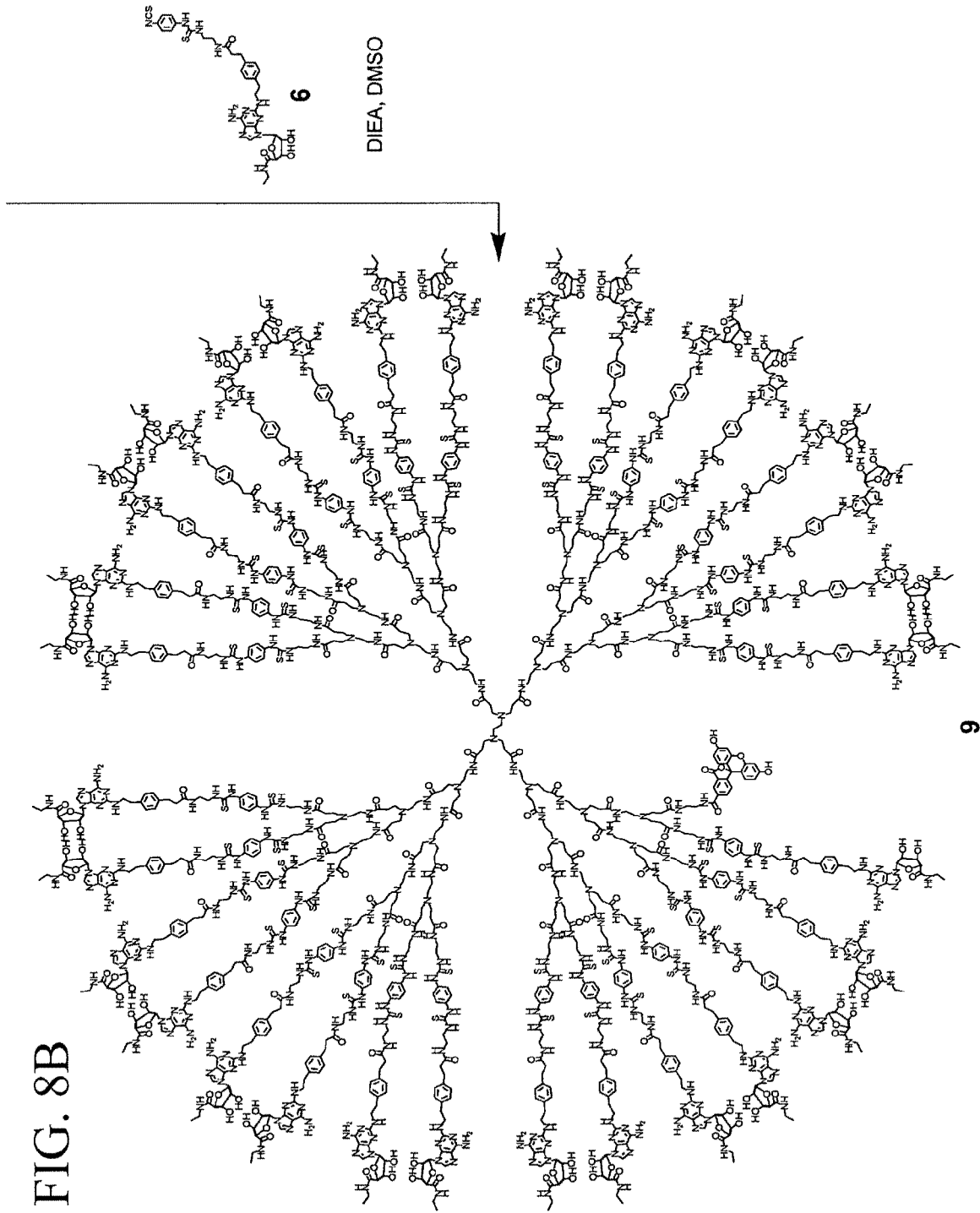
FIG. 8B depicts the second part of Scheme 3.

PAMAM-APEC Conjugate 9 (FIG. 8). A ca. 2.68 mM solution of 1 in DMSO (270 µL, 0.724 µmol) was diluted with DMSO (160 µL), and to this stirred mixture was added DIEA (10.0 µL, 57.4 µmol), followed by a slow addition of a 6.51 mM solution of 5-carboxyfluorescein succinimidyl ester 11 in DMSO (110 µL, 0.716 µmol). The reaction was stirred for 48 h at room temperature, protected from light to make 13. A portion of this crude solution of 13 (250 µL, 0.335 µmol, ca. 1.34 mM) was transferred into another flask, and a 44.1 mM solution of DITC-APEC 6 in DMSO (350 µL, 15.4 µmol) was slowly added to this stirred mixture. The reaction was stirred for 5 d protected from light, purified by SEC (H 39 cm×O.D. 3.0 cm) in DMF, and dried in vacuo to give 9 as an orange glassy solid. $^1$H NMR peak assignments were made following the labeling method analogous to the structure 8 shown previously. $^1$H NMR (600 MHz, DMSO-d$_6$) δ 7.35, 7.32 (br s (each), 116.66H, H$_{13}$ and H$_{14}$), 7.13, 7.10 (d (each), 119.211H, H$_4$ and H$_5$), 6.80 (br s, 51.19H, H$_{6Ad}$), 6.19 (s, 33.01H, H$_1$), 5.85 (d, 30.38H, J=6.6 Hz, H$_{1'}$), 5.63, 5.57 (br s (each), 56.99H, H$_{3'-OH}$ and H$_{2'-OH}$), 4.73 (m, 29.62H, H$_{2'}$), 4.26 (s, 31.27H, H$_{4'}$), 4.19 (s, 28.22H, H$_{3'}$), 3.24 (m, 121.66H, H$_9$ and H$_{fAPEC}$), 2.35 (m, 71.93H, H$_7$), 2.20 (m, 120.00H, H$_c$), 0.96 (t, 91.94H, J=6.9 Hz, H$_{18}$).

Figure 9A:
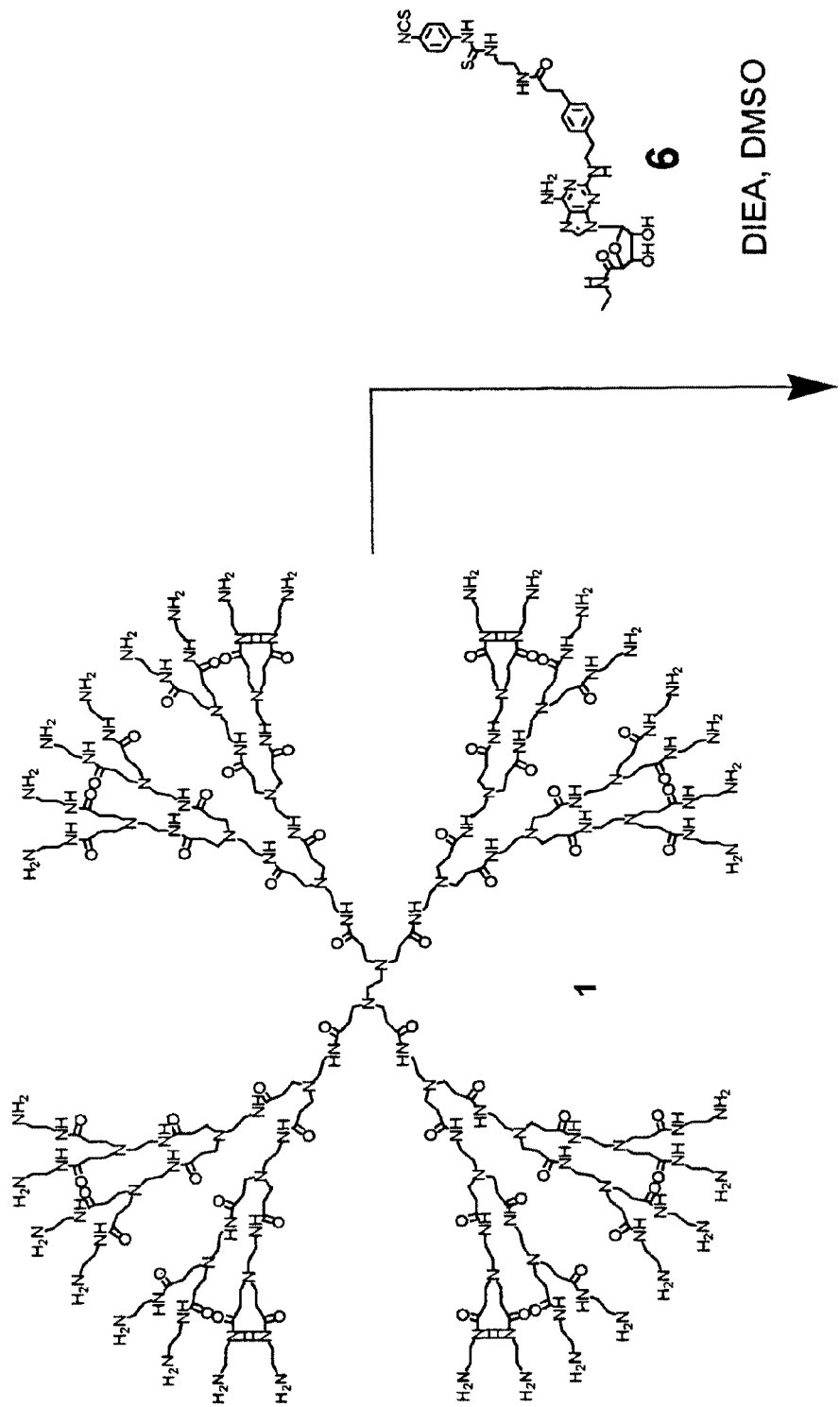
FIG. 9A depicts the first part of Scheme 4, a reaction scheme to prepare a dendrimer conjugate 10, in accordance with an embodiment of the invention.
Figure 9B:
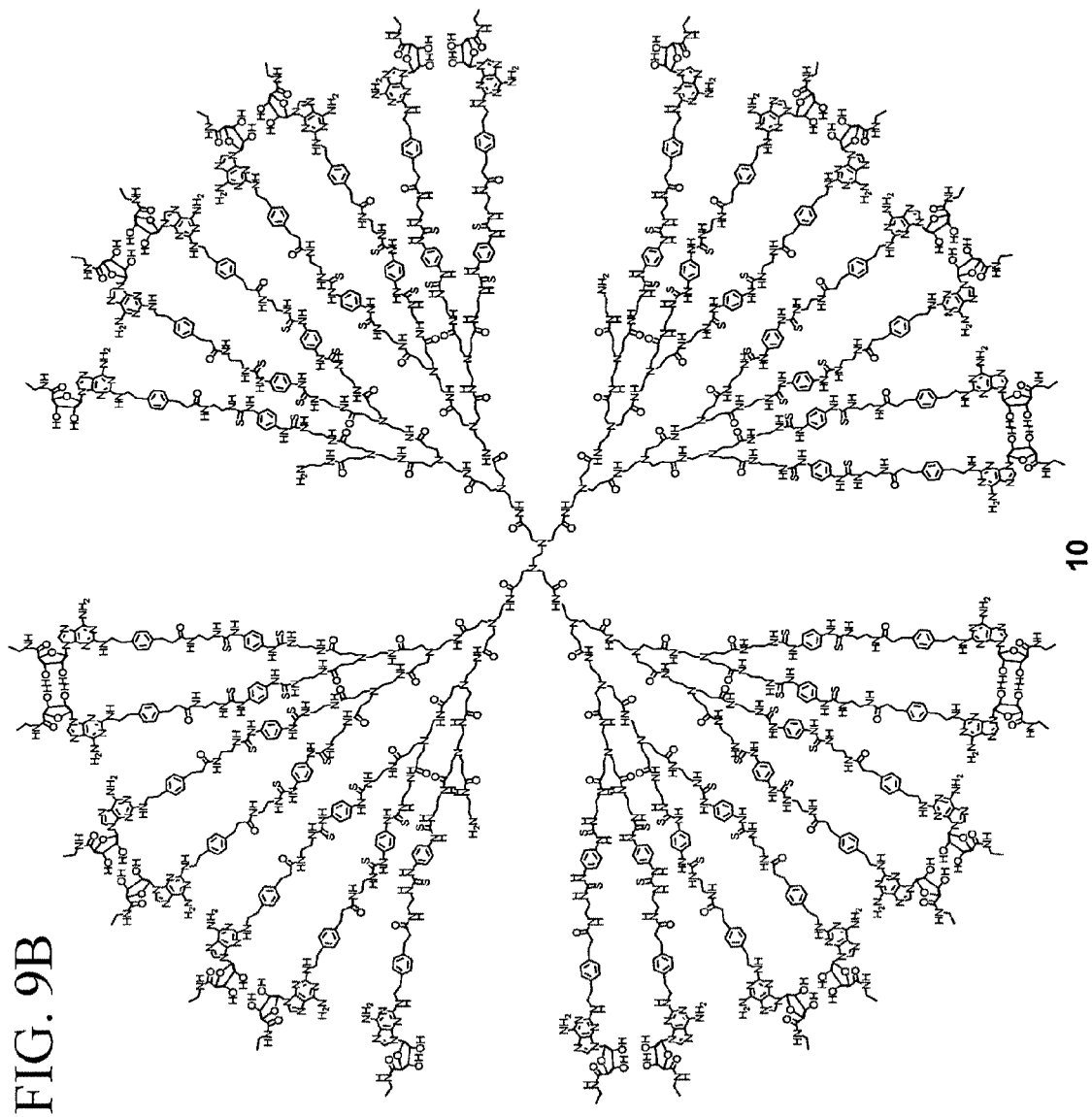
FIG. 9B depicts the second part of Scheme 4.

PAMAM-APEC Conjugate 10 (FIG. 9). A ca. 2.68 mM solution of 1 in DMSO (162 µL, 0.434 mmol) was diluted with DMSO (160 µL), and to this stirred mixture was added DIEA (10.0 µL, 57.4 µmol), followed by a slow addition of a 44.1 mM solution of DITC-APEC 6 in DMSO (450 µL, 19.8 µmol). The reaction was stirred for 7 days protected from light, purified by SEC (H 36.5 cm×O.D. 4.5 cm) in DMF, and dried in vacuo to give 10 as a white glassy solid. $^1$H NMR peak assignments were made following the labeling method analogous to the structure 8 shown previously. $^1$H NMR (600 MHz, DMSO-d$_6$) δ 7.35, 7.32 (br s (each), 107.08H, H$_{13}$ and H$_{14}$), 7.14, 7.10 (d (each), 112.53H, J=7.7 Hz, H$_4$ and H$_5$), 6.80 (br s, 46.44H, H$_{6Ad}$), 6.19 (s, 22.68H, H$_1$), 5.84 (d, 25.40H, J=7.2 Hz, H$_{1'}$), 5.64, 5.58 (br s (each), 47.04H, H$_{3'-OH}$ and H$_{2'-OH}$), 4.72 (m, 25.24H, H$_{2'}$), 4.26 (s, 27.24H, H$_{4'}$), 4.19 (s, 30.58H, H$_{3'}$), 2.20 (m, 120.00H, H$_c$), 0.96 (t, 86.34H, J=6.9 Hz, H$_{18}$).

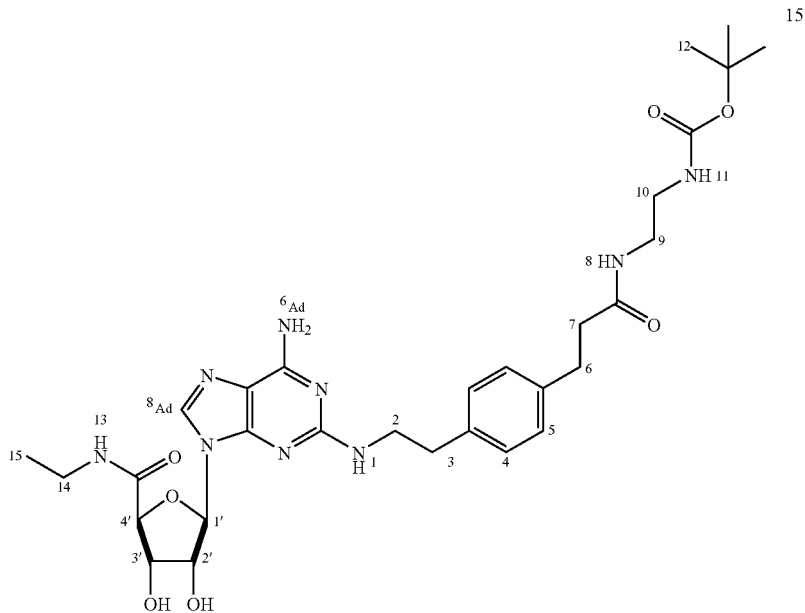

CGS21680 Analogue 15 (FIG. 10). CGS21680 14 (3.73 mg, 6.84 µmol, as a hydrochloride and hemihydrate salt) was dissolved in DMF (500 µL), and DIEA (10.0 µL, 57.4 µmol) was added to this solution. A 63.4 µM solution of N-tert-Boc-ethylenediamine in DMF (112.5 µL, 7.13 µmol) was added to the stirred mixture, followed by PyBOP (2.79 mg, 5.36 µmol) in one portion as a solid. The reaction was stirred for 13 h at room temperature, solvent was removed in vacuo, and the crude product was purified by a preparative TLC (4:1 CHCl$_3$/MeOH) to give 3.10 mg (4.83 µmol, 90%) of 15 as a white solid. R$_f$: 0.41 [silica gel, 4:1 CHCl$_3$/MeOH]; $^1$H NMR (600 MHz, DMSO-d$_6$) δ 8.04 (br s, 1H, H$_{13}$), 8.02 (s, 1H, H$_{8Ad}$), 8.00 (t, 1H, J=5.6 Hz, H$_8$), 7.15 (d, 2H, J=8.4 Hz, H$_4$/H$_5$), 7.11 (d, 2H, J=7.9 Hz, H$_4$/H$_5$), 6.80 (br s, 2H, H$_{6Ad}$), 6.76 (t, 1H, J=6.0 Hz, H$_{11}$), 6.20 (t, 1H, J=5.2 Hz, H$_1$), 5.84 (d, 1H, J=6.7 Hz, H$_{1'}$), 5.58 (d, 1H, J=4.5 Hz, H$_{3'-OH}$), 5.50 (d, 1H, J=6.1 Hz, H$_{2'-OH}$), 4.72 (dd, 1H, J=11.5, 6.4 Hz, H$_{2'}$), 4.25 (d, 1H, J=2.1 Hz, H$_{4'}$), 4.18 (m, 1H, H$_{3'}$), 3.49-3.35 (m, 2H, H$_2$), 3.20-3.05 (m, 2H, H$_{14}$), 3.05 (q, 2H, J=6.2 Hz, H$_9$), 2.94 (q, 2H, J=6.3 Hz, H$_{10}$), 2.77 (m, 4H, H$_3$ and H$_6$), 2.33 (t, 2H, J=8.0 Hz, H$_7$), 1.37 (s, 9H, H$_{12}$), 0.97 (t, 3H, J=7.3 Hz, H$_{15}$); LRMS (ESI) Calcd for C$_{30}$H$_{44}$N$_9$O$_7$ (M+H$^+$): 642.3, Found: 642.3.

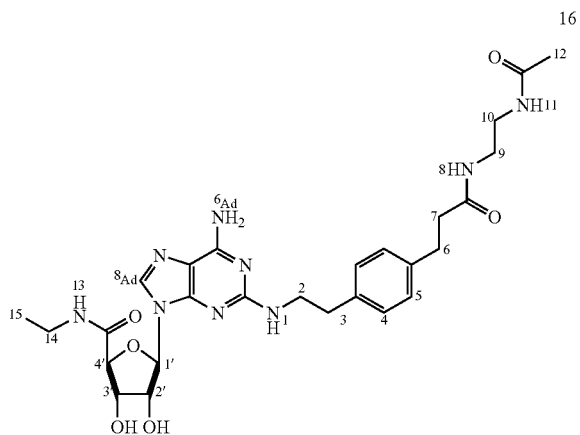

CGS21680 Analogue 16 (Monomeric Control) (FIG. 10). CGS21680 14 (6.26 mg, 11.5 μmol, as a hydrochloride and hemihydrate salt) was dissolved in DMF (1.00 mL), and DIEA (9.15 μL, 52.5 μmol) was added to this solution. Then N-acetylethylenediamine (4.00 μL, 37.6 μmol) was added to the stirred mixture, followed by PyBOP (5.41 mg, 10.4 μmol) in one portion as a solid. The reaction was stirred for 18 h at room temperature, solvent was removed in vacuo, and the crude product was purified by a preparative TLC (5:1 CHCl$_3$/MeOH) to give 0.88 mg (1.51 μmol, 15%) of 16 as a white solid. Low yield of this reaction is possibly due to the highly polar nature of the desired compound 16, which was difficult to recover completely from the preparative TLC plate under acceptable conditions. R$_f$: 0.28 [silica gel, 4:1 CHCl$_3$/MeOH]; $^1$H NMR (600 MHz, DMSO-d$_6$) δ 8.04 (br s, 1H, H$_{13}$), 8.02 (s, 1H, H$_{8Ad}$), 7.87 (t, 1H, J=5.2 Hz, H$_8$), 7.83 (t, 1H, J=5.1 Hz, H$_{11}$), 7.15 (d, 2H, J=7.8 Hz, H$_4$/H$_5$), 7.11 (d, 2H, J=8.4 Hz, H$_4$/H$_5$), 6.79 (br s, 2H, H$_{6Ad}$), 6.20 (t, 1H, J=5.3 Hz, H$_1$), 5.84 (d, 1H, J=6.8 Hz, H$_{1'}$), 5.58 (d, 1H, J=4.1 Hz, H$_{3'-OH}$), 5.50 (d, 1H, J=6.3 Hz, H$_{2'-OH}$), 4.72 (dd, 1H, J=11.7, 6.3 Hz, H$_{2'}$), 4.25 (d, 1H, J=2.3 Hz, H$_{4'}$), 4.18 (m, 1H, H$_{3'}$), 3.49-3.35 (m, 2H, H$_2$), 3.20-3.04 (m, 2H, H$_{14}$), 3.05 (m, 4H, H$_9$ and H$_{10}$), 2.76 (m, 4H, H$_3$ and H$_6$), 2.33 (t, 2H, J=8.1 Hz, H$_7$), 1.78 (s, 3H, H$_{12}$), 0.97 (t, 3H, J=7.3 Hz, H$_{15}$); HRMS (ESI) Calcd for C$_{27}$H$_{38}$N$_9$O$_6$ (M+H$^+$): 584.2945, Found: 584.3066.

General Procedure for Conjugation of Alexa Fluor 488 to the PAMAM G3 Derivatives. (FIG. 12) PAMAM G3 1 was dissolved in DMSO-d$_6$ (ca. 1.1 mM), and then triethylamine (1.5 equiv per primary amine of PAMAM G3 derivative) was added to this stirred solution, followed by a slow addition of a 11.3 mM solution (ca. 1.00 mg/100 μL) of Alexa Fluor 4885-carboxylic acid TFP ester 18 (1.0 equiv per dendrimer) in DMSO-d$_6$. Reaction was stirred for 24-48 h at room temperature protected from light (color change: light orange to wine). Generally, a small amount of red precipitate was observed in most cases, which was removed by filtration using a syringe filter (Millipore Millex®-GN, 0.20 μm) before preparing the NMR sample. $^1$H NMR was measured, and the crude reaction mixture was used to continue to the next step without any further purification.

Figure 12A:
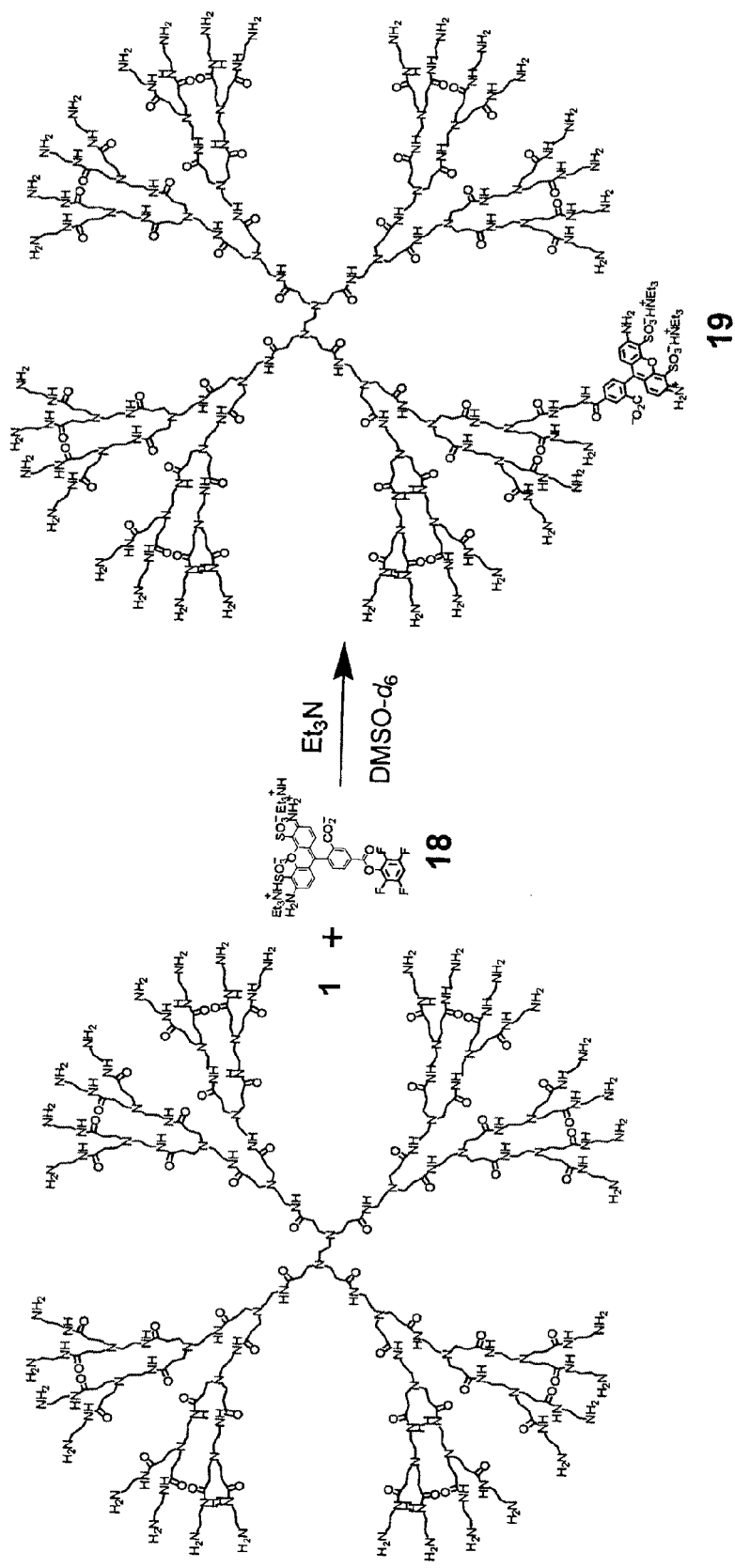
FIG. 12A depicts the first part of Scheme 8, a reaction scheme to prepare dendrimer conjugate 20, in accordance with an embodiment of the invention.
Figure 12B:
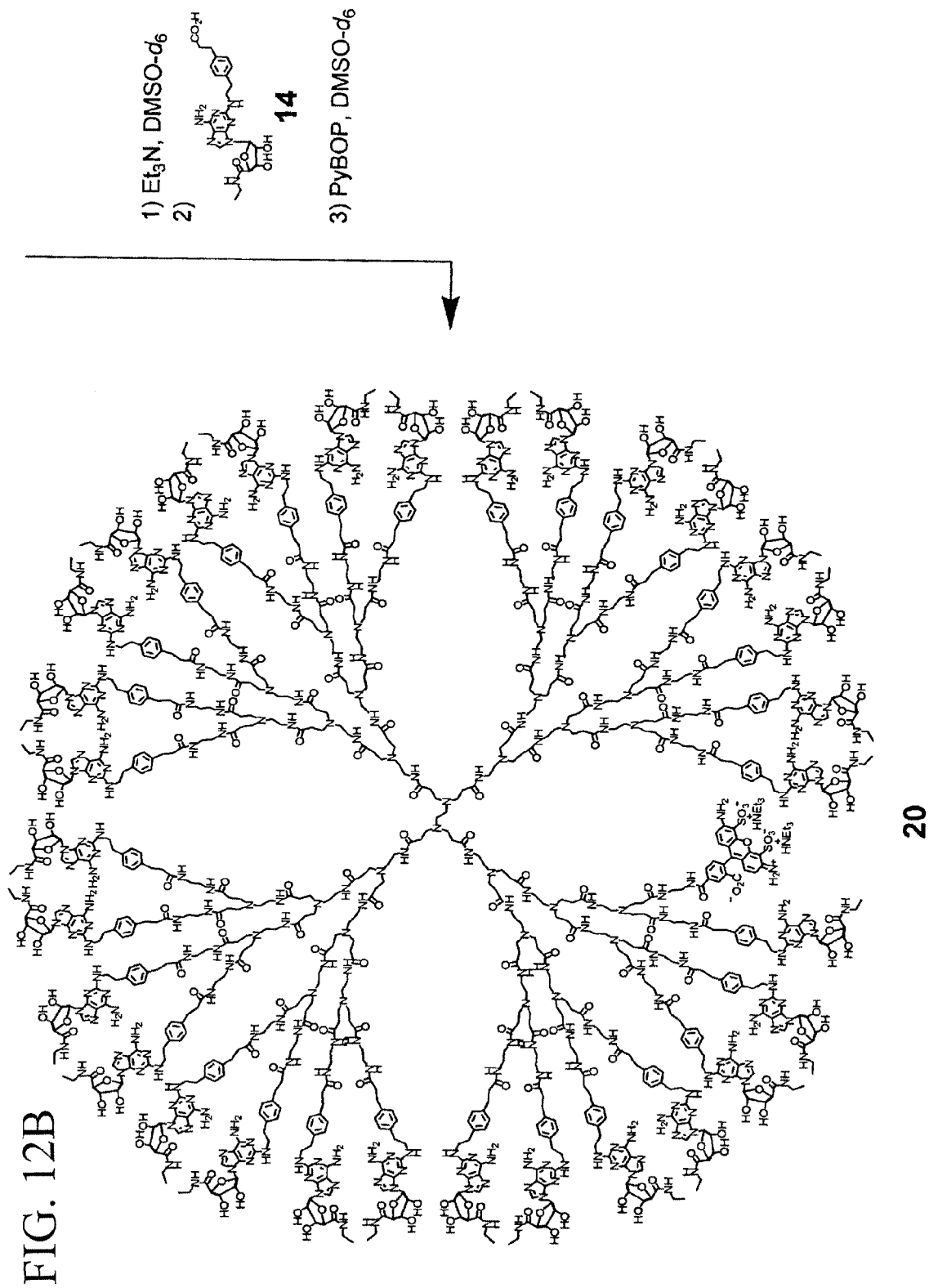
FIG. 12B depicts the second part of Scheme 8.

General Procedure for Conjugation of CGS21680 to the PAMAM G3 Derivatives (FIG. 12). PAMAM G3 dendrimer 1 (or its derivative) and the corresponding amount of CGS21680 14 were dissolved in DMSO-d$_6$ (ca. 0.50 mM solution per dendrimer). If the previous reaction did not involve the usage of base, triethylamine (or DIEA, 1.5 equiv per remaining primary amine of PAMAM G3 derivative) was added to the mixture. A stock solution of PyBOP in DMSO-d$_6$ was prepared immediately before the addition, and the exact stoichiometry of PyBOP corresponding to the molar amount of ligand to be attached was slowly added to the stirred mixture. Reaction was stirred at room temperature for 24 h. The crude mixture in DMSO-d$_6$ was loaded directly on a SEC column in DMF for purification. Column fractions exhibiting fluorescence were combined together and concentrated in vacuo. If the previous steps did not involve the attachment of fluorescent groups, fractions were monitored by a UV light at 254 nm to combine the fractions corresponding to the first UV-active band (i.e., the highest MW with a similar retention time as the fluorescent dendrimer analogue). $^1$H NMR was measured in DMSO-d$_6$ to establish the average number of CGS21680 on the PAMAM dendrimer by the integration method. The compound was dried extensively in vacuo for >5 d to remove the solvents. The yield calculated based on the NMR-determined MW was nearly quantitative.

Figure 11A:
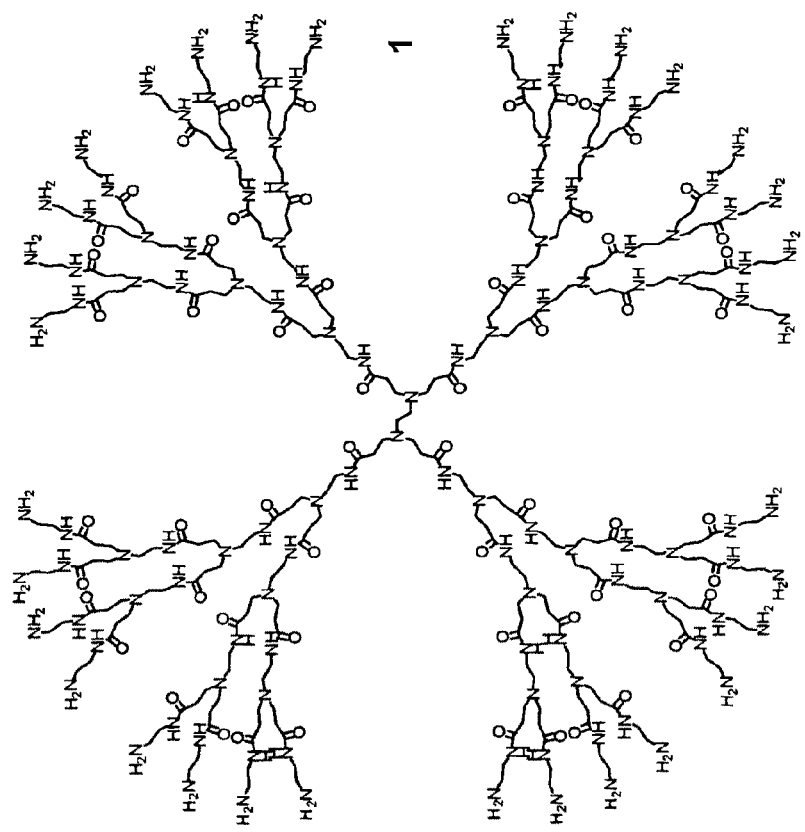
FIG. 11A depicts the first part of Scheme 7, a reaction scheme to prepare dendrimer conjugate 17, in accordance with an embodiment of the invention.
Figure 11B:
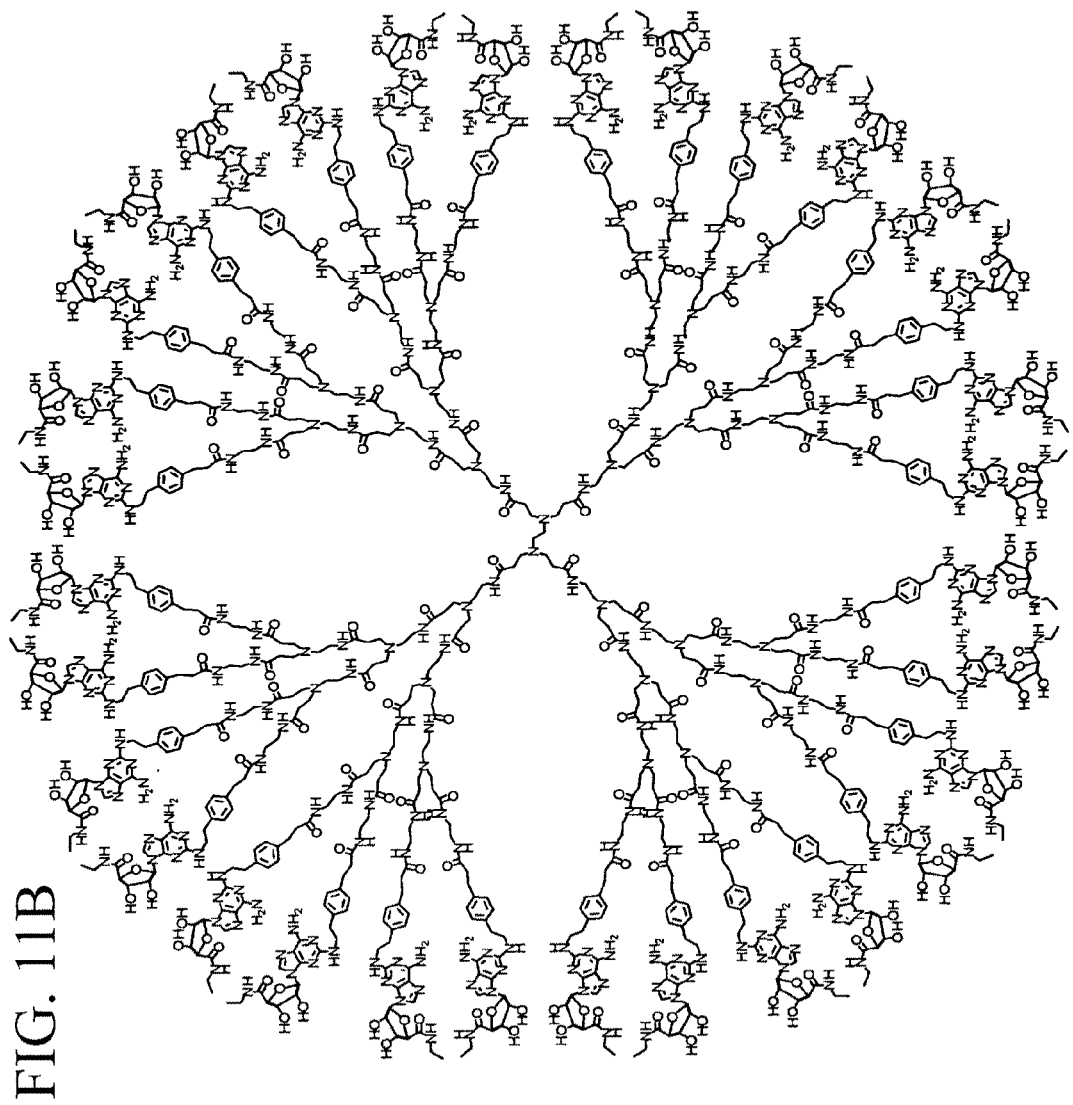
FIG. 11B depicts the second part of Scheme 7.

PAMAM-CGS21680 Conjugate 17 (FIG. 11). PAMAM G3 dendrimer 1 (3.35 mg, 0.485 μmol) and CGS21680 (9.44 mg, 17.3 μmol) were dissolved completely in DMSO-d$_6$ (500 μL). To this stirred mixture was added DIEA (20.0 μL, 115 mmol), followed by a 33.3 mM solution of PyBOP in DMSO-d$_6$ (465 μL, 15.5 μmol). The reaction was stirred for 24 h, then purified by SEC (H 38.5 cm×O.D. 3.0 cm) in DMF, and dried in vacuo to give 17 as a white glassy solid. $^1$H NMR peak assignments were made following the labeling method analogous to the structure 20 shown below. $^1$H NMR (600 MHz, DMSO-d$_6$) δ 8.04, 8.02 (s (each), 67.47H, H$_8$ and H$_{8Ad}$), 7.94 (br s, 34.04H, NH$_{G3}$), 7.90 (br s, 34.78H, NH$_{CGS}$), 7.81 (br s, 31.53H, NH$_{G0}$, NH$_{G1}$, and NH$_{G2}$), 7.11, 7.08 (d (each), 135.30H, H$_4$ and H$_5$), 6.82 (br s, 61.67H, H$_{6Ad}$), 6.19 (s, 31.89H, H$_1$), 5.85 (d, 31.49H, J=6.4 Hz, H$_{1'}$), 5.65, 5.58 (br s (each), 62.38H, H$_{3'-OH}$ and H$_{2'-OH}$), 4.73 (m, 30.37H, H$_{2'}$), 4.26 (s, 32.11H, H$_{4'}$), 4.20 (s, 30.72H, H$_{3'}$), 2.75 (m, 133.06H, H$_3$ and H$_6$), 2.64 (m, 124.89H, H$_b$), 2.41 (m, 57.91H, H$_e$), 2.33 (t, 73.02H, H$_7$), 2.18 (m, 120.00H, H$_c$), 0.95 (t, 95.76H, J=6.8 Hz, H$_{10}$).

PAMAM-CGS21680 Conjugate 20 (FIG. 12). PAMAM G3 dendrimer 1 (15.35 mg, 2.22 μmol) was dissolved in DMSO-d$_6$ (1.80 mL), and then triethylamine (5.00 μL, 35.9 μmol) was added to this solution. An 11.3 mM solution of Alexa Fluor 488 5-carboxylic acid TFP ester 18 (195 μL, 2.20 μmol) was then added to this mixture, and the reaction was continued to stir for 48 h. The red precipitate formed was removed by filtration, and the crude product 19 was used for next step without any purification. A portion of 19 (600 μL, 0.667 μmol, ca. 1.11 mM) was transferred into another flask, and to this was added CGS21680 14(12.91 mg, 23.69 μmol). Then, to this stirred mixture was added triethylamine (12.6 μL, 90.4 μmol, followed by a 30.7 mM solution of PyBOP in DMSO-d$_6$ (685 μL, 21.0 μmol). The reaction was stirred for 24 h, then purified by SEC (H 38.5 cm×O.D. 3.0 cm) in DMF, and dried in vacuo to give 20 as an orange glassy solid. $^1$H NMR (600 MHz, DMSO-d$_6$) δ 8.04, 8.02 (s (each), 68.07H, H$_8$ and H$_{8Ad}$), 7.93 (br s, 33.85H, NH$_{G3}$), 7.89 (br s, 34.38H, NH$_{CGS}$), 7.80 (br s, 30.13H, NH$_{G0}$, NH$_{G1}$, and NH$_{G2}$), 7.12, 7.08 (d (each), 125.24H, H$_4$ and H$_5$), 6.81 (br s, 58.62H, H$_{6Ad}$), 6.19 (s, 31.00H, H$_1$), 5.85 (d, 30.00H, J=7.2 Hz, H$_{1'}$), 5.63, 5.56 (br s (each), 57.74H, H$_{3'-OH}$ and H$_{2'-OH}$), 4.73 (m, 28.09H, H$_{2'}$), 4.26 (s, 30.14H, H$_{4'}$), 4.19 (s, 28.20H, H$_{3'}$), 2.75 (m, 127.76H, H$_3$ and H$_6$), 2.64 (m, 107.99H, H$_b$), 2.41 (m, 58.00H, $H_e$), 2.33 (t, 70.62H, $H_7$), 2.18 (m, 120.00H, $H_c$), 0.95 (t, 92.40H, J=6.6 Hz, $H_{10}$).

PEG derivatives of dendrimers. General Procedure for Synthesis of PEG carbonate 40. PEG carbonate 40 was prepared by a modified procedure of Kojima et al. Three different lengths of commercial PEG derivatives were selected to initiate the synthesis. A series of PEG monomethyl ether 38 each having the average MW of 550, 750, or 2000 (m=ca. 12 (38a), 16 (38b), and 45 (38c), Scheme 17, FIG. 21) was treated with 4-nitrophenyl chloroformate 39 to make a carbonate 40. This PEG carbonate 40 was purified by SEC in DMF to combine fractions containing pure compounds, and its average MW was estimated by the $^1$H NMR integration (m=13 (40a), 15 (40b), and 45 (40c)). This reactive intermediate 40 was then added to the solution of PAMAM G3 1 slowly in DMSO (Scheme 18, FIG. 21). Ten different types of PAMAM-PEG conjugates 41-50 were created as such, which were purified by SEC in DMF. $^1$H NMR was used to determine the range of SEC fractions containing the desired products. The first and last fractions from SEC with low concentrations of desired PAMAM-PEG conjugates were deliberately eliminated in order to reduce the polydispersity of the polymeric product mixture. Then the SEC fractions of PAMAM-PEG conjugates were combined. Here, the $^1$H NMR integration method was used again to calculate the average number of PEG groups attached, and to reevaluate the average number of repeating units comprising the PEG moieties. The composition of each PAMAM-PEG conjugate and its corresponding MW are summarized in Table 2.

To the poly(ethylene glycol) monomethyl ether 38 in THF were added 4-nitrophenylchloroformate (2 equiv) and triethylamine (2 equiv). The reaction was stirred at room temperature for 24 h. Solvent was removed under reduced pressure, and the crude mixture was loaded on a SEC column for purification. This reaction generated a dicarbonate form of PEG (2:1 attachment) made from a small amount of diol present in the commercial compound 38 as a contaminant. The SEC fractions containing the desired product 40 were identified by $^1$H NMR. Only the fractions containing 40 as a pure compound were combined and used for next step.

40

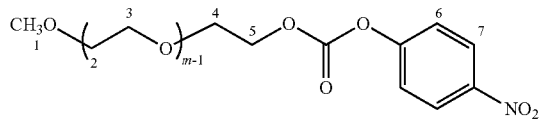

PEG Carbonate 40a. $^1$H NMR (300 MHz, CDCl$_3$) δ 8.26 (d, 2H, J=9.5 Hz, $H_7$), 7.38 (d, 2H, J=9.1 Hz, $H_6$), 4.42 (m, 2H, $H_5$), 3.79 (m, 2H, $H_4$), 3.71-3.51 (m, 54H, $H_2$ and $H_3$), 3.36 (s, 3H, $H_1$); $^{13}$C NMR (75 MHz, CDCl$_3$) δ 155.7, 152.6, 145.5, 125.5, 122.0, 72.1, 70.9, 70.7, 68.8, 68.5, 59.2; HRMS (ESI) Calcd for $C_{32}H_{59}N_2O_{17}$ (m=12, M+NH$_4^+$): 743.3814, Found: 743.3785.

PEG Carbonate 40b. $^1$H NMR (300 MHz, CDCl$_3$) δ 8.27 (d, 2H, J=9.2 Hz, $H_7$), 7.38 (d, 2H, J=9.4 Hz, $H_6$), 4.43 (m, 2H, $H_5$), 3.80 (m, 2H, $H_4$), 3.72-3.52 (m, 64H, $H_2$ and $H_3$), 3.37 (s, 3H, $H_1$); $^{13}$C NMR (75 MHz, CDCl$_3$) δ 125.5, 122.0, 72.1, 70.9, 70.8, 68.8, 68.5, 61.9, 59.2; HRMS (ESI) Calcd for $C_{40}H_{75}N_2O_{21}$ (m=16, M+NH$_4^+$): 919.4862, Found: 919.4877.

PEG Carbonate 40c. $^1$H NMR (300 MHz, CDCl$_3$) δ 8.27 (d, 2H, J=9.0 Hz, $H_7$), 7.38 (d, 2H, J=9.2 Hz, $H_6$), 4.43 (m, 2H, $H_5$), 3.80 (m, 2H, $H_4$), 3.70-3.53 (m, 186H, $H_2$ and $H_3$), 3.37 (s, 3H, $H_1$); $^{13}$C NMR (75 MHz, CDCl$_3$) δ 125.5, 122.0, 72.1, 70.8, 68.8, 68.5, 60.1; HRMS (ESI) Calcd for $C_{98}H_{187}N_2O_{50}$Na (m=45, M+Na$^+$): 2201.2019, Found: 2201.1978.

General Procedure for Synthesis of PAMAM-PEG conjugates. Typically 30-90 μL of PAMAM G3 1 as a methanolic solution (Aldrich) was dried in vacuo for >24 h to determine the accurate amount (60 μL gives about 11 mg after drying). Dendrimer 1 was dissolved in DMSO (1.3-1.5 mM) and the corresponding amount of activated PEG carbonate 40 was added slowly either as a solution (for PEG$_{550}$ and PEG$_{750}$) in DMSO or as a solid (for PEG$_{2000}$). The reaction was stirred at room temperature for 7 d. The crude mixture was loaded directly to a SEC column in DMF to isolate the desired PAMAM-PEG conjugate 41-50. The SEC fractions containing the desired product were identified by $^1$H NMR. The first and last fractions of SEC containing the desired compound were deliberately eliminated when combined, in order to reduce the polydispersity of the PAMAM-PEG conjugate. $^1$H NMR was measured in DMSO-d$_6$ to establish the average numbers of PEG groups and their chain lengths (i.e., the average number of repeating unit) on the PAMAM dendrimer by the integration method. In addition PAMAM-PEG conjugate 41-50 was dried extensively in vacuo for >7 d to remove the solvent. The reaction yield calculated based on the NMR-determined structure was nearly quantitative. Tables 1-2 set forth characterization data on the PAMAM-PEG conjugates.

TABLE 1

Average number of surface groups on PAMAM G3 conjugates estimated by the $^1$H NMR analysis and their calculated average molecular weights (MWs).

| | | | # of peripheral units | | | | | |
|---|---|---|---|---|---|---|---|---|
| cmpd | fluorescein[a] | Alexa Fluor 488[a] | APEC | CGS21680 | acetamide | carboxylate | amine[b] | MW |
| 8 | 1 | 0 | 5 | 0 | 14 | 0 | 12 | 11525 |
| 9 | 1 | 0 | 31 | 0 | 0 | 0 | 0 | 30017 |
| 10 | 0 | 0 | 29 | 0 | 0 | 0 | 3 | 28191 |
| 12 | 1 | 0 | 0 | 0 | 14 | 0 | 17 | 7856 |
| 13 | 1 | 0 | 0 | 0 | 0 | 0 | 31 | 7267 |
| 17 | 0 | 0 | 0 | 32 | 0 | 0 | 0 | 22317 |
| 19 | 0 | 1[e] | 0 | 0 | 0 | 0 | 31 | 7628 |
| 20 | 0 | 1[e] | 0 | 31 | 0 | 0 | 0 | 22554 |
| 21 | 0 | 1[e] | 31 | 0 | 0 | 0 | 0 | 30378 |

TABLE 1-continued

Average number of surface groups on PAMAM G3 conjugates estimated by the $^1$H NMR analysis and their calculated average molecular weights (MWs).

| | | | # of peripheral units | | | | | |
|---|---|---|---|---|---|---|---|---|
| cmpd | fluorescein[a] | Alexa Fluor 488[a] | APEC | CGS21680 | acetamide | carboxylate | amine[b] | MW |
| 22 | 0 | 0 | 0 | 0 | 15 | 0 | 17 | 7539 |
| 23 | 0 | 1[e] | 0 | 0 | 15 | 0 | 16 | 8258 |
| 24 | 0 | 1[e] | 5 | 0 | 15 | 0 | 11 | 11928 |
| 26[c] | 0 | 0 | 0 | 0 | 44 | 0 | 60 | 27860 |
| 27[c] | 0 | 1[e] | 0 | 0 | 44 | 0 | 59 | 28578 |
| 28[c] | 0 | 1[e] | 15 | 0 | 44 | 0 | 44 | 39586 |
| 30[d] | 0 | 0 | 0 | 0 | 100 | 0 | 115 | 60214 |
| 31[d] | 0 | 1[e] | 0 | 0 | 100 | 0 | 114 | 60933 |
| 32[d] | 0 | 1[e] | 30 | 0 | 100 | 0 | 84 | 82948 |
| 33 | 0 | 1[e] | 0 | 15 | 0 | 0 | 16 | 14850 |
| 35 | 0 | 1[e] | 0 | 15 | 16 | 0 | 0 | 15523 |
| 36 | 0 | 1[e] | 0 | 15 | 0 | 16[f] | 0 | 16676 |
| 37 | 0 | 1[g] | 0 | 15 | 0 | 16[h] | 0 | 16645 |

[a]Estimated based on the molar equivalents added to the reaction.
[b]Assumed that the commercial PAMAM G3 dendrimer contained 32 terminal amino groups.
[c]Made from PAMAM G5 dendrimers.
[d]Made from PAMAM G6 dendrimers.
[e]As a triethylamine salt.
[f]As a methyl ester of succinic acid.
[g]As a sodium salt.
[h]As a sodium salt of succinate.

TABLE 2

Structures of PAMAM-PEG conjugates and their average MWs estimated by the $^1$H NMR integration.

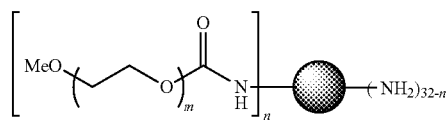

| compound | $M_n$ of 38 used[a] | m | n | MW |
|---|---|---|---|---|
| 41 | 550 | 12 | 4 | 9256 |
| 42 | 550 | 12 | 7 | 11016 |
| 43 | 550 | 12 | 14 | 15122 |
| 44 | 550 | 12 | 32 | 25682 |
| 45 | 750 | 15 | 9 | 13378 |
| 46 | 750 | 15 | 32 | 29911 |
| 47 | 2000 | 44 | 4 | 14894 |
| 48 | 2000 | 44 | 8 | 22880 |
| 49 | 2000 | 44 | 16 | 38850 |
| 50 | 2000 | 44 | 32 | 70792 |

[a]$M_n$ taken from the Aldrich bottle.

Radioligand Membrane Binding Experiments. Radioligand binding assays were performed for $A_1$, $A_{2A}$, and $A_3$ ARs. Each tube in the binding assay contained 100 µL of membrane suspension (20 µg of protein), 50 µL of agonist radioligand, and 50 µL of increasing concentrations of the test ligands in Tris-HCl buffer (50 mM, pH 7.5) containing 10 mM MgCl$_2$. Nonspecific binding was determined using 10 mM 5'-N-ethylcarboxamidoadenosine diluted with the buffer. The mixtures were incubated at 25° C. for 60 min. Binding reactions were terminated by filtration through Whatman GF/B filters under a reduced pressure using a MT-24 cell harvester (Brandell, Gaithersburg, Md.). Filters were washed three times with 5 mL of 50 mM ice-cold Tris-HCl buffer (pH 7.5). For $A_3$ AR, the agonist radioligand [$^{125}$I]-(4-amino-3-iodobenzyl)adenosine-5'-N-methyluronamide (0.5 nM) was used. After the filters were washed, the radioactivity was measured using a Beckman γ-counter. For the $A_1$ and $A_{2A}$ assays, the radioactive agonists [$^3$H] N$^6$-chlorocyclopentyladenosine and [$^3$H] 2-(4-(2-carboxyethyl)phenylethylamino)-5'-N-ethylcaboxamido-adenosine were used, respectively. After the filters were washed, they were placed in scintillation vials containing 5 mL of Hydrofluor scintillation buffer and counted using a Perkin Elmer Liquid Scintillation Analyzer. The $K_i$ value was determined using GraphPad Prism for all assays.

Calcium Protocol. Chinese Hamster Ovary (CHO) cells stably expressing the human $A_3$ receptor were grown in Dulbecco's Modified Eagle Medium/F12 (Sigma) supplemented with 10% fetal bovine serum, antibiotics, and glutamine. Each assay was completed by passaging the CHO $A_3$ cells into 96 well plates and incubating overnight at 37° C. with 5% CO$_2$. The FLIPR Calcium 4 Kit provided by Molecular Devices was used as described previously (Niebauer). Briefly, the media was removed from the cells, and 30 µl of the Calcium 4 fluorescent dye supplemented with 2.5 mM probenecid was added to each well. The cells were incubated at room temperature for 45 minutes. The compound plate was prepared by diluting the compounds to $10^{-5}$-$10^{-9}$ M in Hanks Buffer. Samples were run in duplicate on the Molecular Devices FlexStation I at room temperature. Cellular fluorescence (excitation=485 nm; emission=525 nm) was monitored following exposure to compound. Increases in intracellular calcium are reported as the relative fluorescence units after exposure minus the basal fluorescence value before exposure. Each experiment was repeated at least three times. From this data, the EC$_{50}$ value for each compound was calculated (GraphPad Prism).

Cytotoxicity Studies. Cytotoxicity assays were run for the various PAMAM G3 derivatives as well as other dendrimer generations, including dendrimers with acetamide, PEG, and carboxylate end groups. Many of the compounds were not soluble in aqueous buffers. Therefore, in order to dissolve the compounds, 0.5 µmol of each compound was weighed into a vial, and 50 µL of DMSO was added. Each mixture was heated to 80° C. for 30 min, and cooled to room temperature. 5 mL of DMEM/F12 media (Mediatech Inc.) containing 10% fetal bovine serum and antibiotics was added to each compound so that the final concentration of DMSO was 1%. All further dilutions used media supplemented with 1% DMSO, which was shown not to affect cell growth. The solution was heated to 37° C. for an additional 30 min to ensure the compound was dissolved.

Serial dilutions of the compounds using the 1% DMSO media were prepared using 100-1 µM for the commercial compounds and 30 µM-0.3 µM for the synthesized compounds. Each dilution was added to a six-well plate, and 30,000 cells were seeded per well. Two plates for each compound were prepared so that one plate could be used for cell counting and the other plate could be used for hematoxylin staining. The cells grew for a period of 5 d till 90% confluent. To count the cells, the media was first aspirated. 1 mL of phosphate-buffered solution (PBS) was added to each well, and removed. The cells were detached with 0.2 mL of trypsin and diluted with 2 mL of media. The cell density of each well was counted to determine the effect of the added dendrimer derivative on cell survival, as an indication of cytotoxicity. For the hematoxylin staining, the media was removed, and the cells were washed with PBS. Next, the cells were fixed with methanol for 10 min. After three further washings with PBS for 5 min each, the cells were stained with 4 g/L hematoxylin (35.2 g/L aluminum sulfate, 0.4 g/L sodium iodate) for 10 min. After additional three washes with PBS for 5 min each, the cells were allowed to air dry before adding the glycerol. The image was visualized using a Zeiss bright-field microscope.

Synthesis and Characterization of PAMAM-APEC Dendrimer Conjugates. The design and synthesis of dendrimer conjugates to test for the GPCR signaling involved partial acetylation of the PAMAM surface, attachment of fluorescein for imaging, and conjugation of multiple numbers of modified APEC as an agonist ligand.

Acetylation of PAMAM. Partial acetylation of the cationic amine-terminated PAMAM periphery is known to improve the biocompatibility of these dendrimers by decreasing the nonspecific binding and cytotoxicity, and to better expose the ligands attached to the surface of dendrimers for the interactions with receptors. This effect is expected to result from the elimination of charge repulsions, and subsequent neutralization of the PAMAM dendrimer surface, which leads to the shrinkage of the overall size—the hydrodynamic radius—of the dendrimer in water to make a more compact structure, and thus to prevent the entry of surface-attached ligands to the interiors of the dendrimers. Moreover, these small acetyl moieties are less likely to impose significant steric barriers for favorable ligand-receptor interactions unlike the more common surface modification strategy achieved using poly(ethylene glycol) (PEG) groups. Therefore, the first step in the synthesis of our dendrimer conjugates was to modify the dendrimer surface by partial acetylation.

Figure 13A:
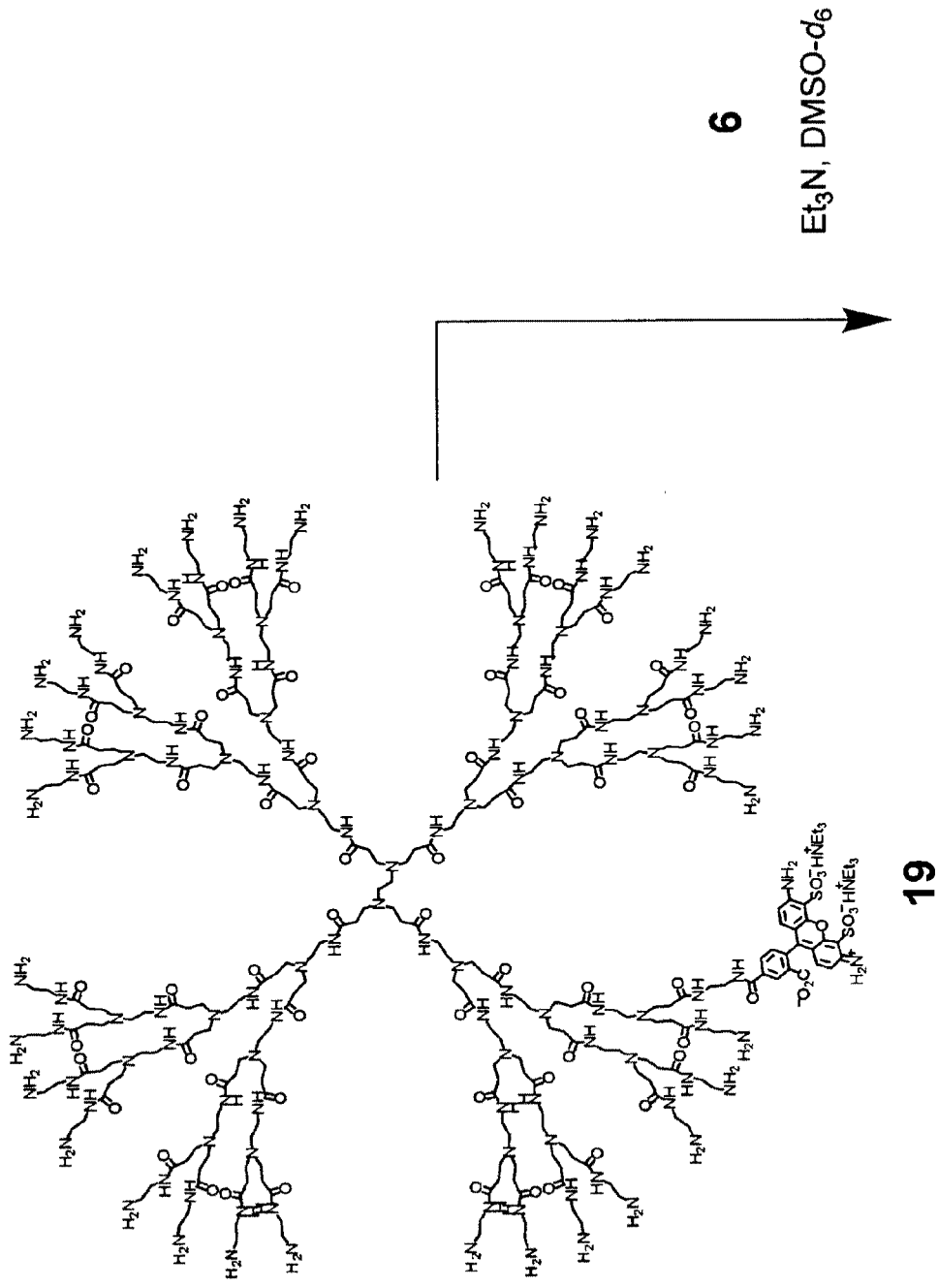
FIG. 13A depicts the first part of Scheme 9, a reaction scheme to prepare dendrimer conjugate 21, in accordance with an embodiment of the invention.
Figure 13B:
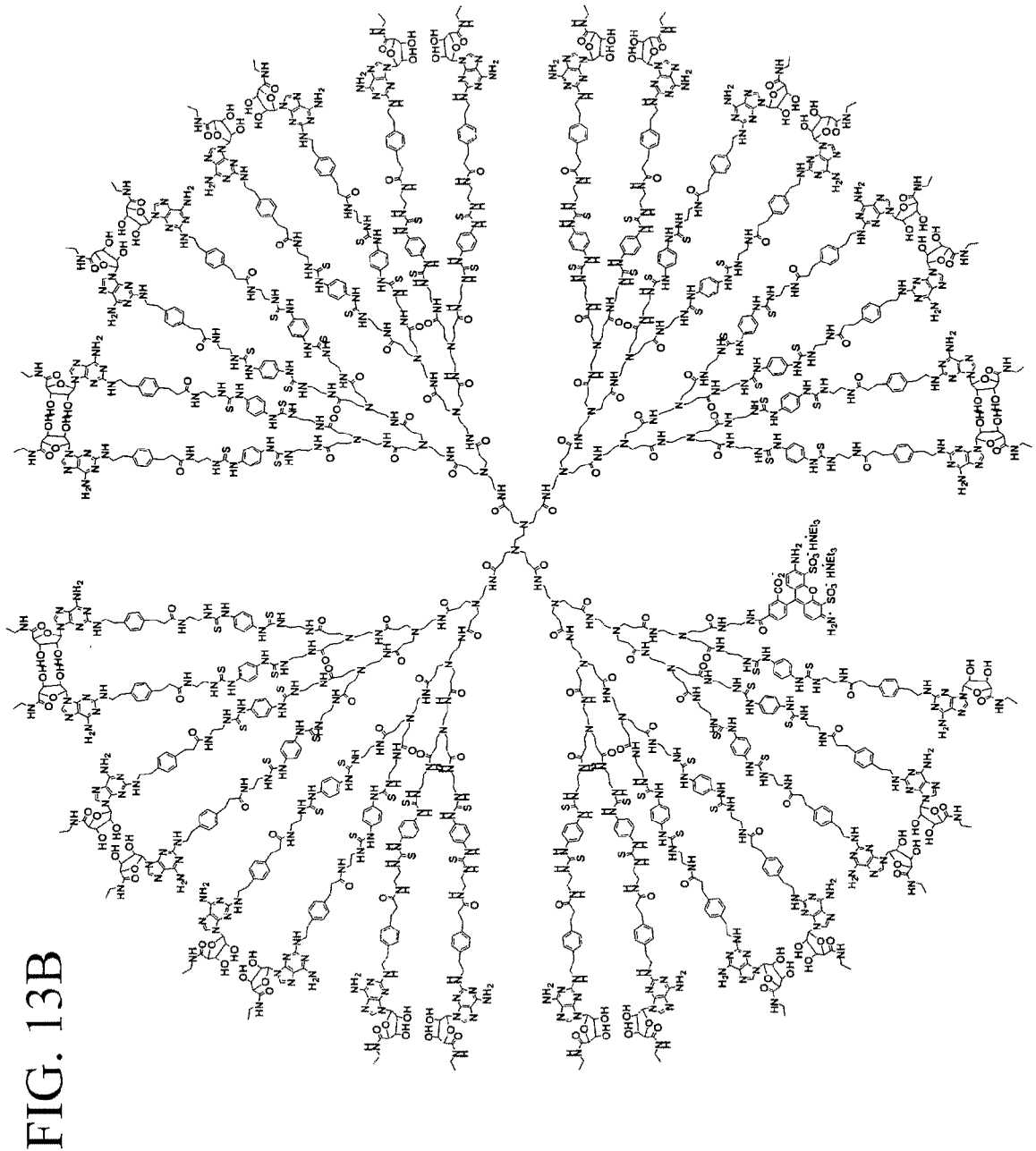
FIG. 13B depicts the second part of Scheme 9.
Figure 14A:
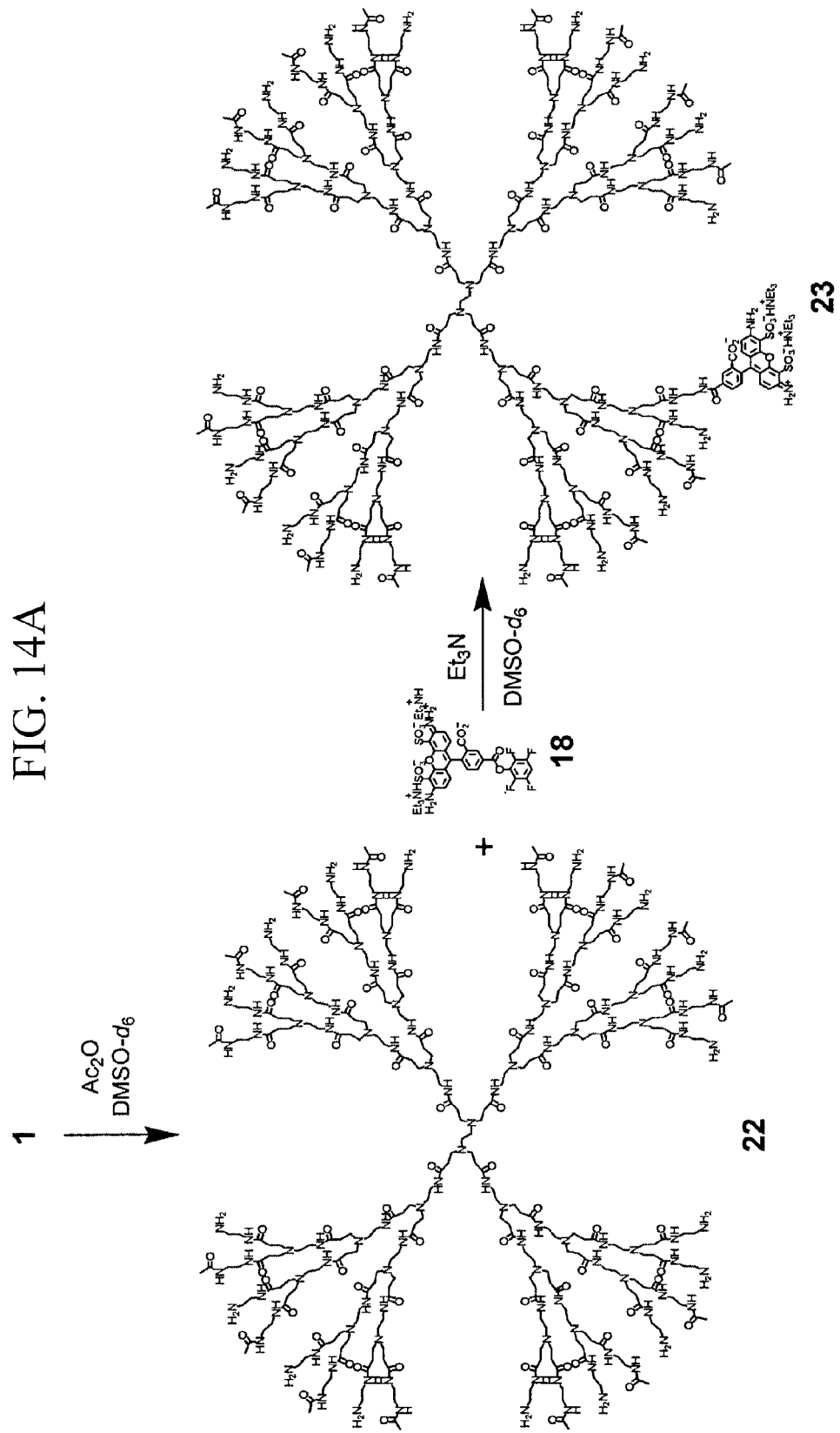
FIG. 14A depicts the first part of Scheme 10, a reaction scheme to prepare dendrimer conjugate 24, in accordance with an embodiment of the invention.
Figure 14B:
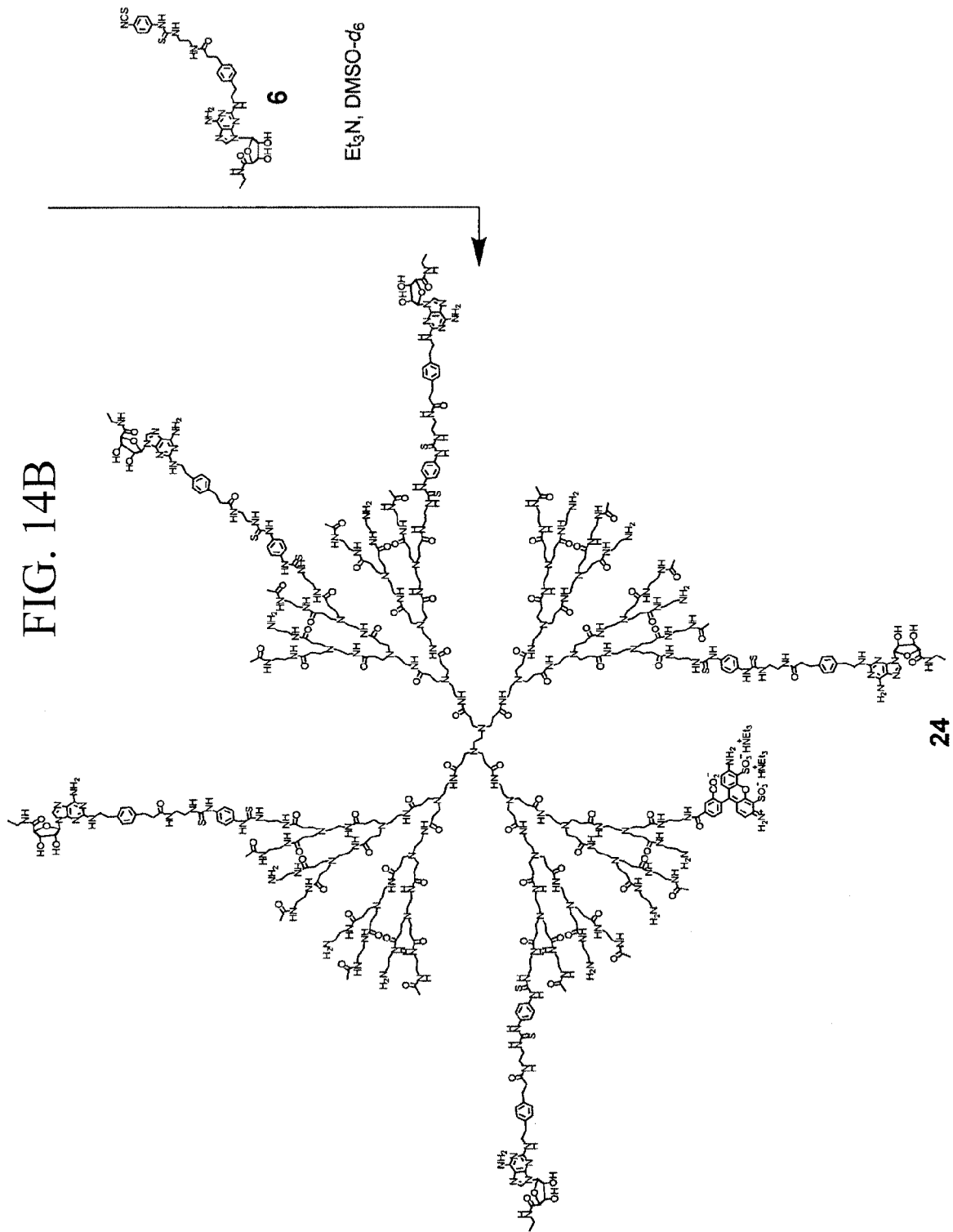
FIG. 14B depicts the second part of Scheme 10.
Figure 15:
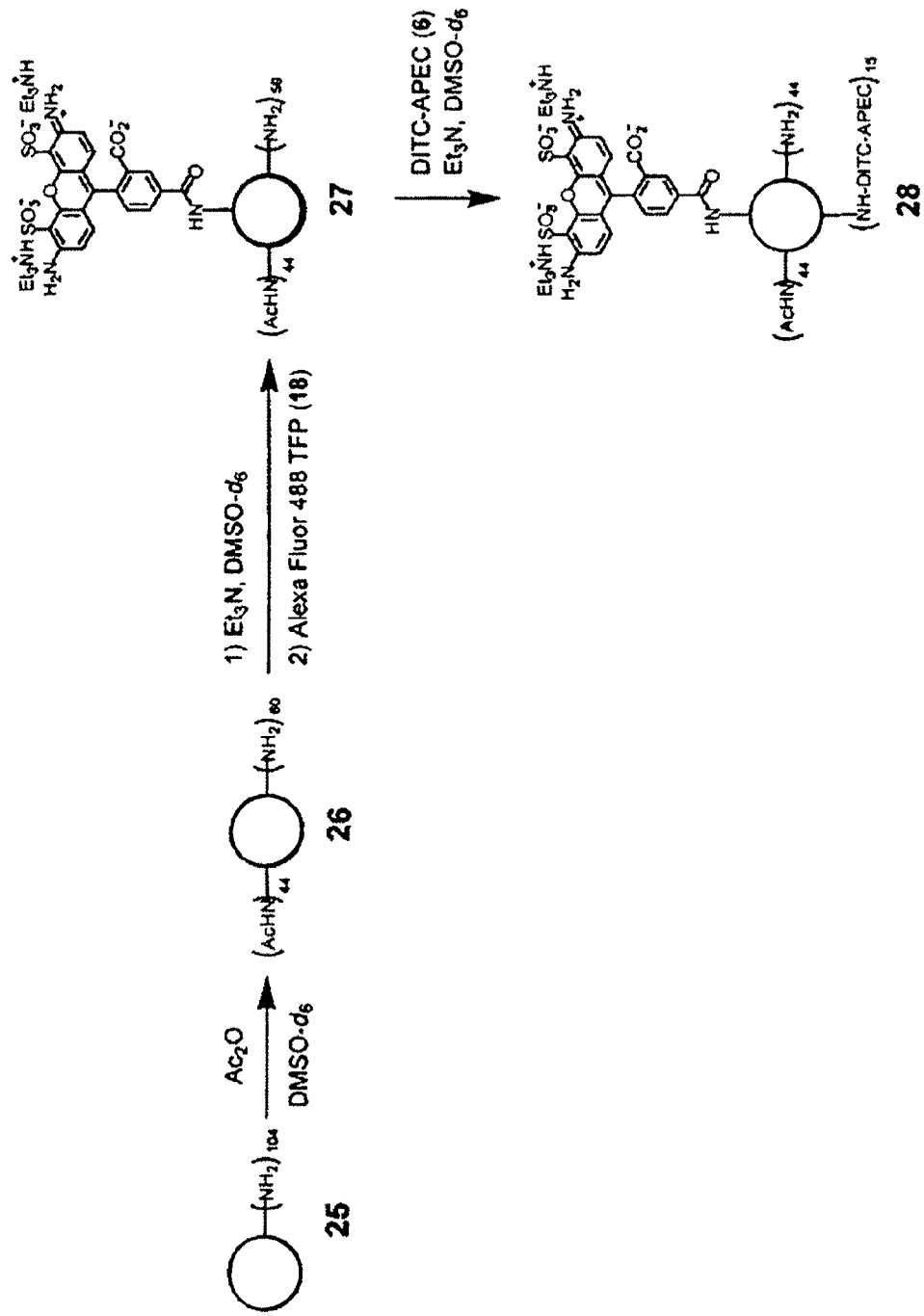
FIG. 15 depicts Scheme 11, a reaction scheme to prepare dendrimer conjugate 28, in accordance with an embodiment of the invention.
Figure 16:
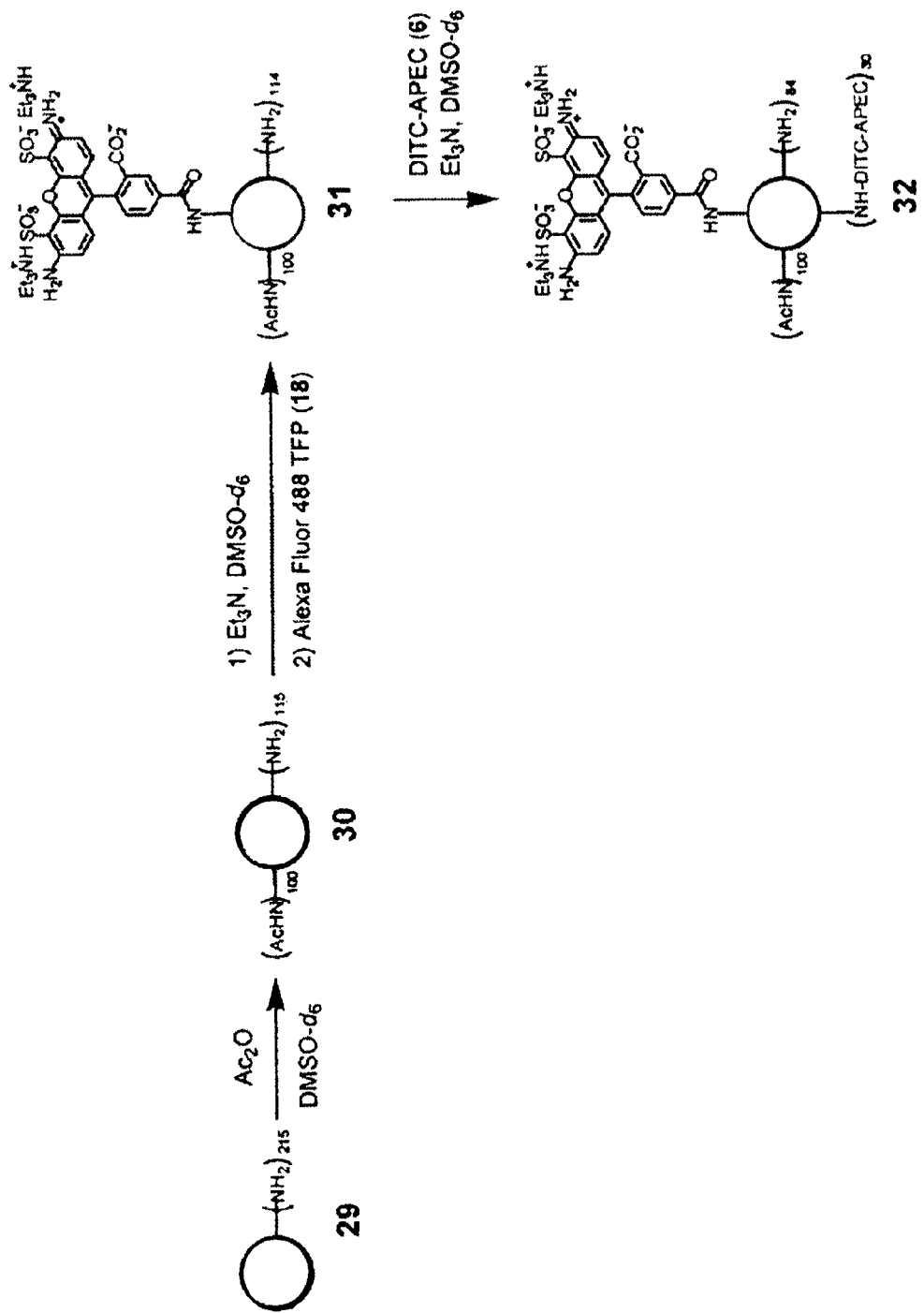
FIG. 16 depicts Scheme 12, a reaction scheme to prepare dendrimer conjugate 32, in accordance with an embodiment of the invention.
Figure 17B:
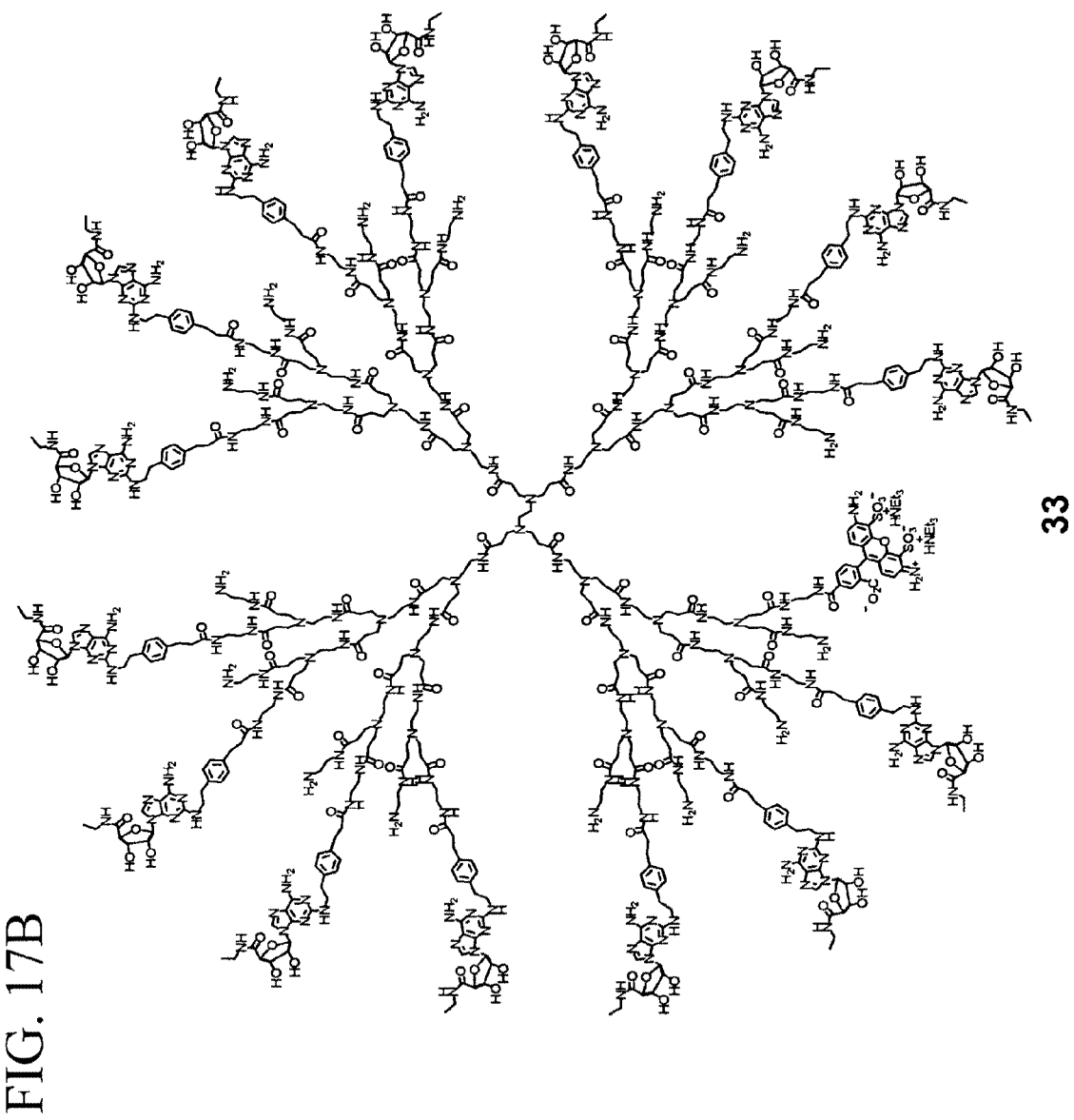
FIG. 17B depicts the second part of Scheme 13.

PAMAM-APEC conjugate 21 (Scheme 9, FIG. 13) with Alexa Fluor 488 as a fluorescent tracer was synthesized from the common intermediate 19, and characterized in a similar manner as for the fluorescein analogue 9 (Scheme 3, FIG. 8). In addition, PAMAM dendrimer conjugates with Alexa Fluor 488 containing low loads of APEC moieties were prepared from G3, G5, and G6 amine-terminated PAMAM dendrimers in a similar manner (Schemes 10-12, FIG. 14-16). The composition of acetamide and APEC groups was maintained similar to that of dendrimer 8 (i.e., ca. 45% for acetamide; ca. 15% for APEC), however, minimal amount of Alexa Fluor 488 was added to each dendrimer (a molar equivalent per dendrimer). In order to control the stoichiometry accurately in each substitution reaction, the commercial G5 and G6 PAMAM dendrimers were first titrated with varying amounts of acetic anhydride in DMSO-$d_6$ to determine the molar amounts of terminal amino groups per milligram of dendrimer.

PAMAM Conjugates with Modified Surface—Amine, Acetamide, and Carboxylate Groups. The fully substituted PAMAM-ligand conjugates 20 and 21 may retain the maximal potential to interact with receptors at different locations synergistically to increase the binding affinity exponentially. Despite their highest achievable multivalency as G3 PAMAM dendrimers, these structures suffer from poor water-solubility hampering routine biological assays in aqueous media. Accordingly, modification of the PAMAM properties may be necessary, which can be simply achieved by attaching some more soluble groups on the surface of dendrimers. It is important to note that the required ligand-receptor interactions should not be altered significantly by applying this modification. Here, three types of PAMAM surface groups were envisioned to evaluate the physical properties and their effect on the ligand-receptor binding: 1) amino groups remaining after partial attachment of ligands; 2) acetamide groups by post-modifying the surface using the succinimide ester of acetic acid; 3) carboxylate groups through peptide coupling to the surface of the dendrimer with monomethyl succinate followed by hydrolysis.

Compared to the fully substituted PAMAM dendrimers, those with untreated multiple terminal amino groups tend to dissolve easier in water. This structure 33 can be made by partially attaching the CGS21680 ligands to fluorescent dendrimer 19 through a peptide coupling strategy as described before (Scheme 10, FIG. 14). However, PAMAM dendrimers with multiple amino groups are known to be relatively cytotoxic and may result in an increased level of nonspecific binding interactions.

Figure 18:
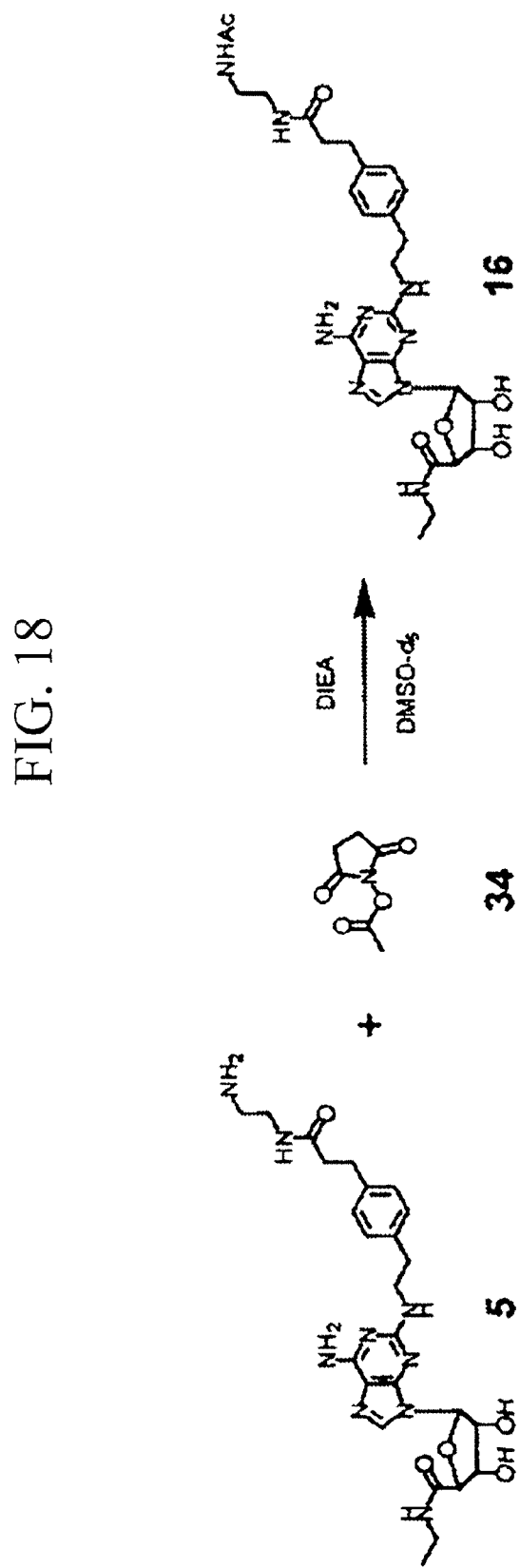
FIG. 18 depicts Scheme 14, a reaction scheme to prepare an intermediate compound 16, in accordance with an embodiment of the invention.
Figure 19A:
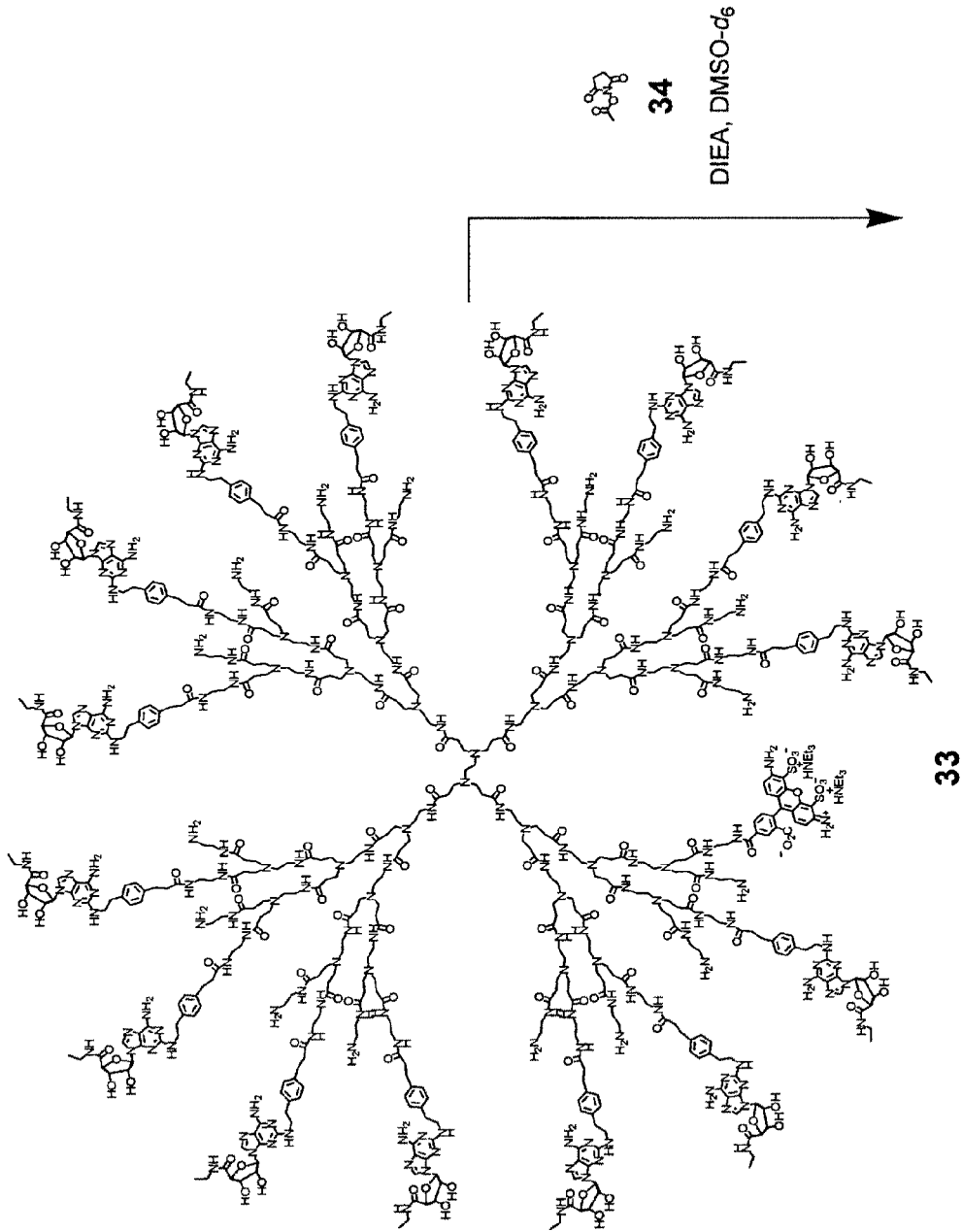
FIG. 19A depicts the first part of Scheme 15, a reaction scheme to prepare dendrimer conjugate 35, in accordance with an embodiment of the invention.
Figure 19B:
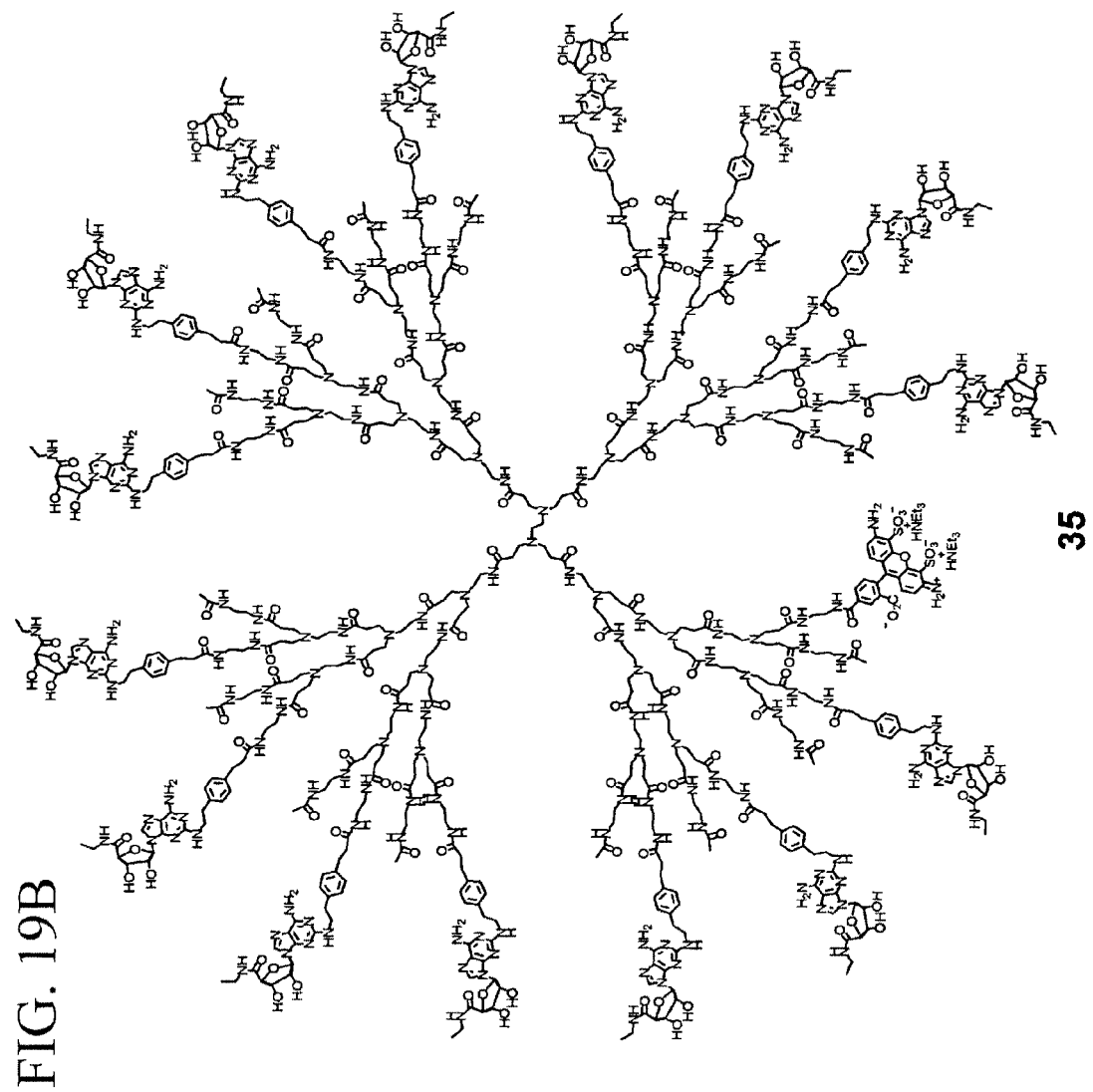
FIG. 19B depicts the second part of Scheme 15.

Alternatively, these potentially toxic amino groups can be capped by converting them into acetamide groups. Initially, a partial acetylation step was planned as the first step using acetic anhydride in the synthesis. However, to make a PAMAM-CGS21680 conjugate using the PyBOP coupling method, the acetate anion from the earlier acetylation reaction needed to be removed to avoid its further coupling to the dendrimer by PyBOP. Unfortunately, when partially acetylated dendrimers were passed through the preparative SEC column in DMF to remove the acetate anions, the distribution of the product mixture changed substantially to a higher average MW, and this effect was more pronounced for less acetylated PAMAM dendrimers which had a poorer solubility in DMF. Dialysis may be an alternative; however, this procedure usually takes several days and may not remove the small anions completely. In order to better control the stoichiometry of the reactions, a post-acetylation procedure was planned using a succinimde ester of acetic acid 34. Unlike acetic anhydride, 34 is expected to react efficiently only at the primary amine. The synthetic utility of 34 was evaluated first on the APEC 5 which has a primary amine, an adenine N6 amine, and two unprotected hydroxyl groups (Scheme 14, FIG. 18). Thus, APEC 5 was treated with 1.5 equivalents of 34 under basic conditions. $^1$H NMR analysis of the crude mixture showed predominantly the desired product 16 with remaining 34 as an only minor compound. Consequently, acetylated PAMAM-CGS21680 conjugate 35 is made by adding a slight excess of 34 to the dendrimer conjugate 33 (Scheme 15, FIG. 19).

Figure 20A:
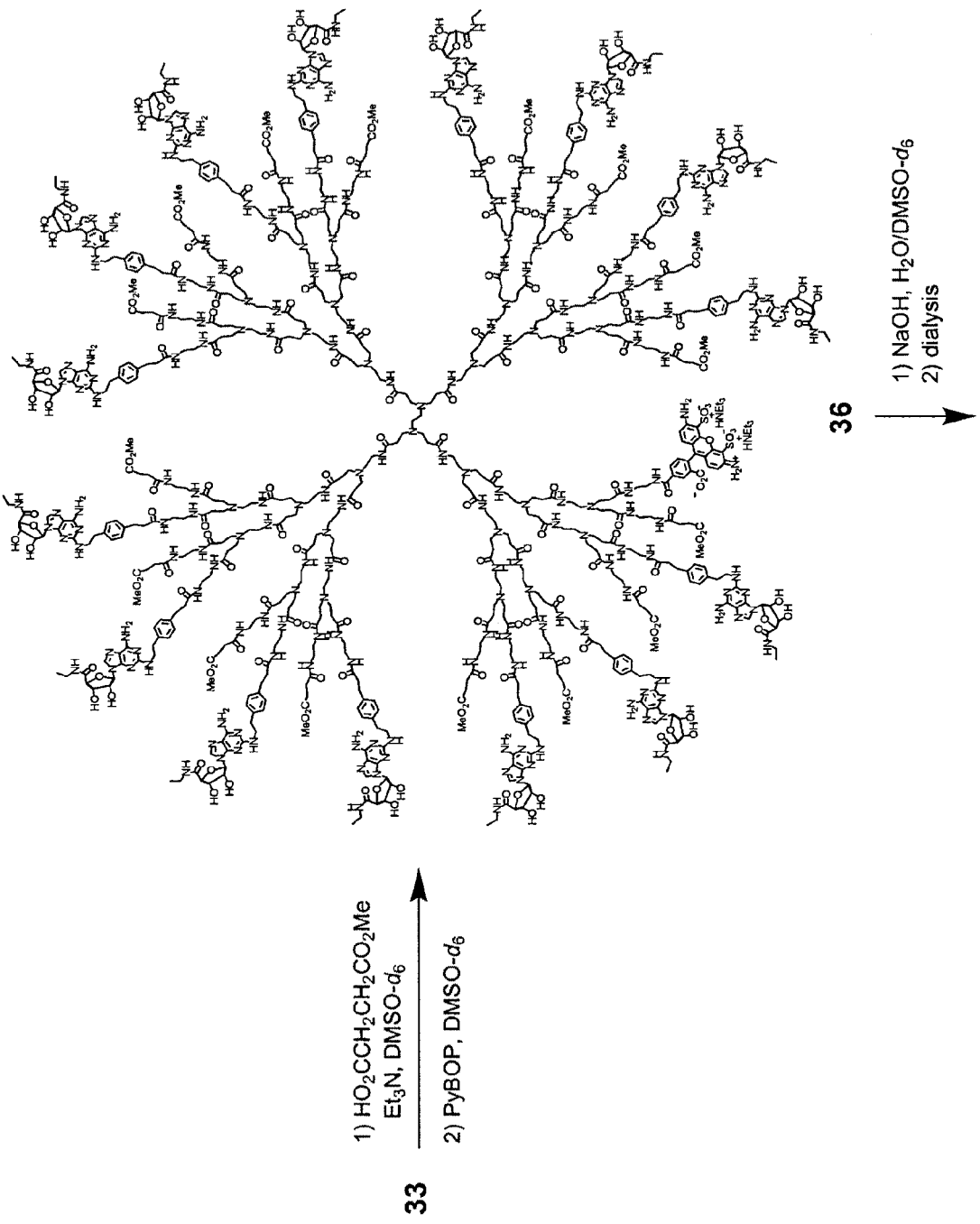
FIG. 20A depicts the first part of Scheme 16, a reaction scheme to prepare dendrimer conjugate 37, in accordance with an embodiment of the invention.
Figure 20B:
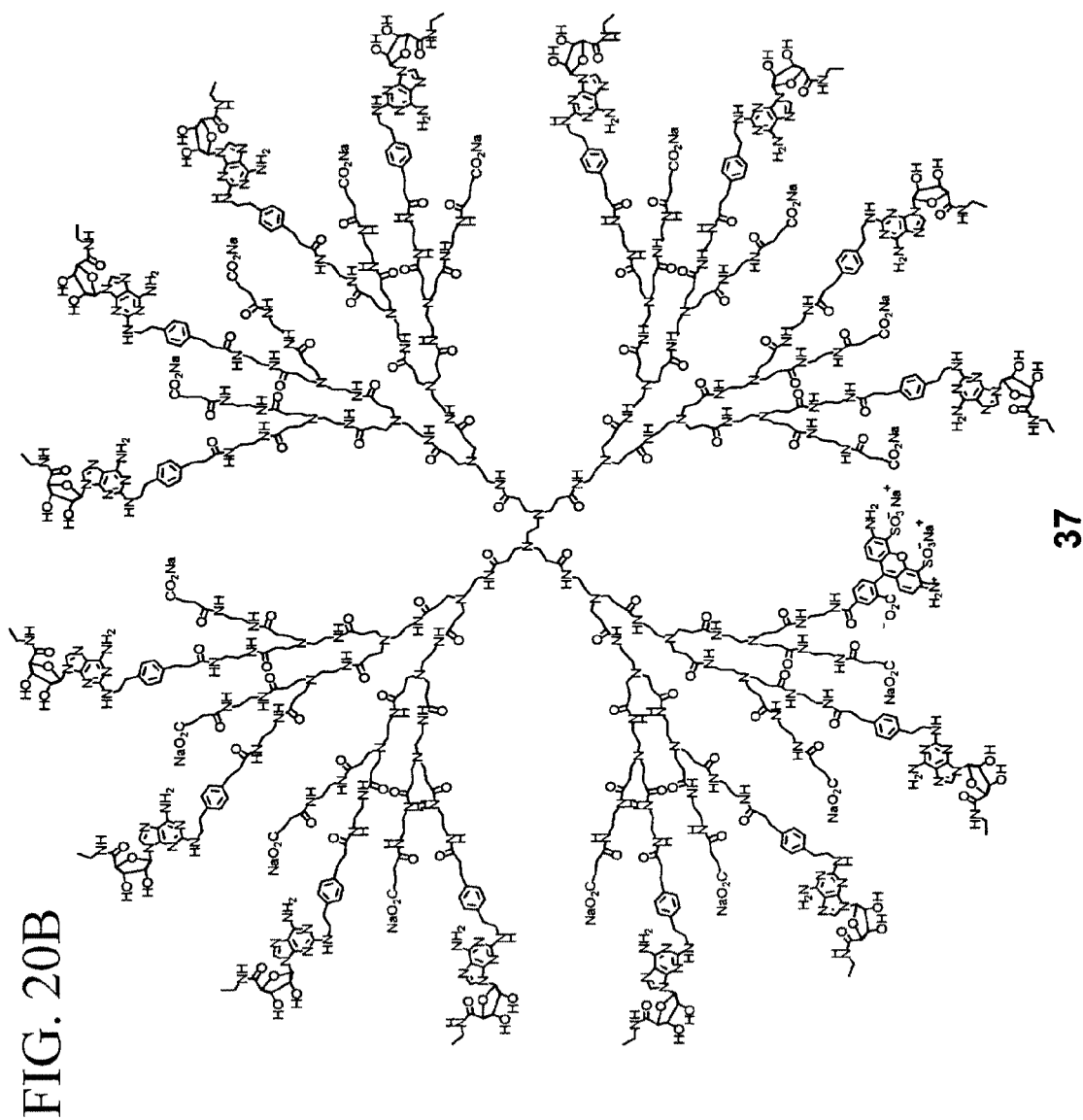
FIG. 20B depicts the second part of Scheme 16.
Figure 22:
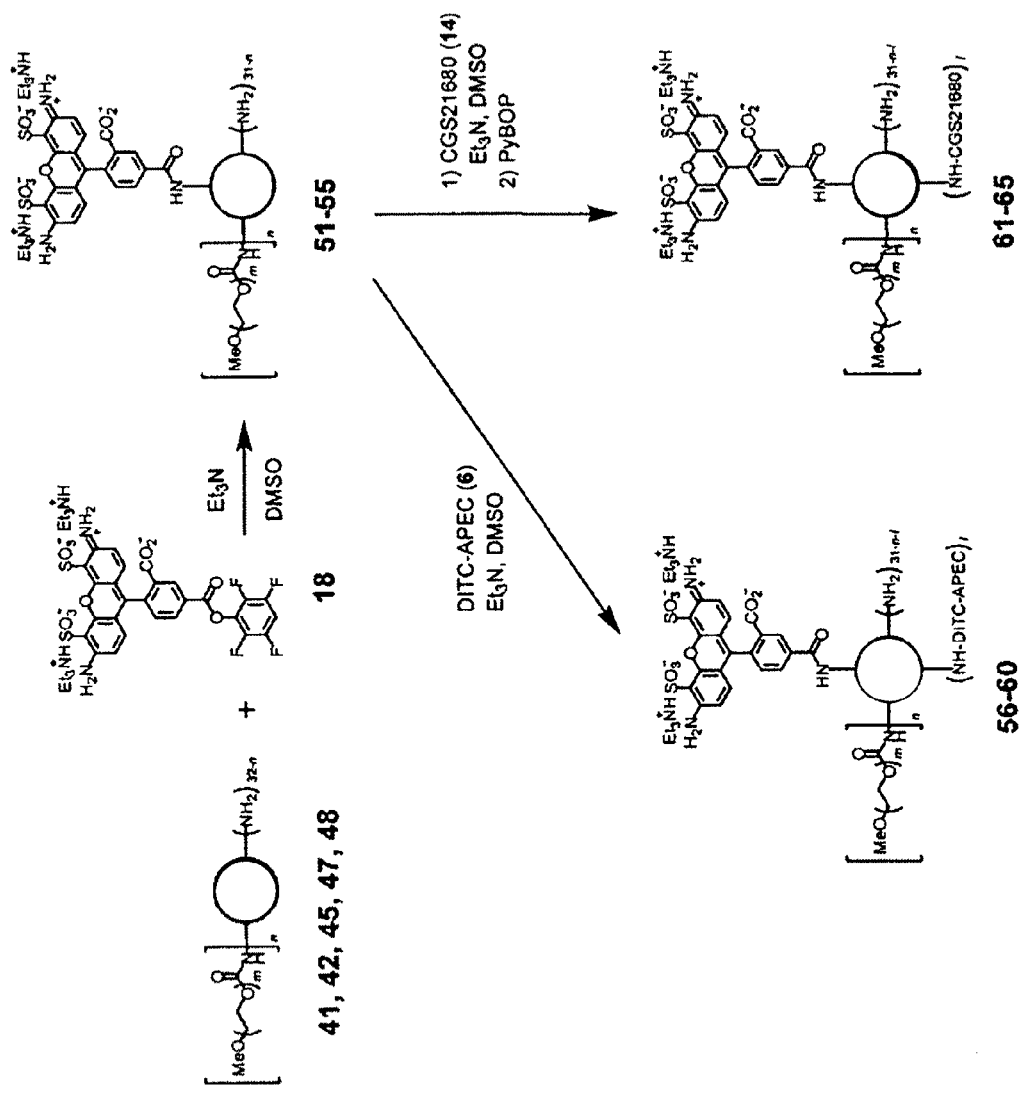
FIG. 22 depicts Scheme 19, a reaction scheme to prepare dendrimer conjugates 56-65, in accordance with embodiments of the invention.

On the other hand, the attachment of a few numbers of carboxylate groups—typically as a sodium salt—to the outer rim is one of the most common strategies to achieve the needed water-solubility for supramolecular architectures. As in protein binding pockets, this simple modification usually allows these molecules to maintain their programmed assembly through directional polar interactions in hydrophobic structured environments shielded from the aqueous solution outside. Modification of the PAMAM surface into carboxylate groups is accomplished by PyBOP coupling strategy with monomethyl succinic acid, followed by hydrolysis to afford 37 as a sodium salt after dialysis (Scheme 16, FIG. 20).

Conformational Studies of PAMAM Conjugates by NMR. Nuclear Overhauser enhancement (NOE) experiments were performed for PAMAM-APEC conjugates 8, 9, and 10, and for PAMAM-CGS21680 conjugates 17 and 20 in DMSO-$d_6$. PAMAM interiors were predicted to maintain a relatively compact structure by forming exchangeable multiple hydrogen-bonds in water or methanol. Unlike water molecules which may interact mostly at the surface of PAMAM with polar groups, aprotic DMSO may readily penetrate into the interiors of the PAMAM to compete and destroy the hydrogen-bonded network. Indeed, in our preliminary NOESY experiments, NOE cross-peaks were observed between methylene units of PAMAM ("b" and "c") and the methyl of the ribose ring of both APEC and CGS21680, suggesting possible internalization of the ligands to the PAMAM interiors. These cross-peaks between PAMAM interiors and ligand moiety seemed to become weaker with increasing amounts of $D_2O$ in DMSO-$d_6$.

Computer Modeling of PAMAM Conjugates. To estimate the inter-ligand distances within a dendrimer and the average diameter of our nanocarrier based on a PAMAM G3 dendrimer, computer modeling was carried out using HyperChem7.5.2 software. Here, the energy minimized structures of two PAMAM conjugates each bearing 32 APEC (66) or 32 CGS21680 (17) as ligands were obtained. First, ligands mimicking the dendrimer-attached moiety (7 for APEC and 16 for CGS21680) were first energy-minimized using a semi-empirical PM3 method. The lowest energy conformation of each ligand had a fully stretched geometry with C (methyl of ribose)-$N_{G3}$ (nitrogen from PAMAM terminus) distance of ca. 37 Å and 23 Å for 7 and 16, respectively (FIG. 23).

Figure 24B:
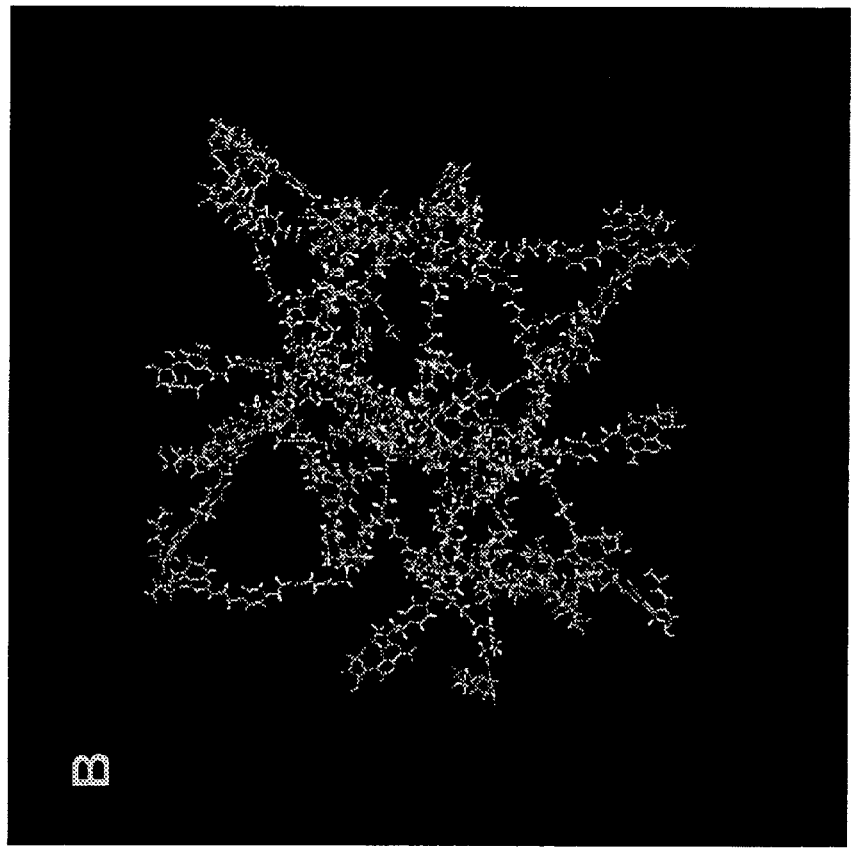

Next, partial structures of eight copies of each minimized ligand, 7 and 16, were appropriately attached to the periphery of a minimized PAMAM G3 dendron, which was then energy-minimized. Finally, four copies of each minimized PAMAM G3 dendron carrying eight ligands were attached to a PAMAM G0 core to make a G3 dendrimer with 32 copies of ligands, which was subsequently minimized by an Amber force field to give the final dendrimer conjugates, 66 and 17 (FIG. 24).

Unlike the fully stretched geometry of the adenosine moiety calculated through PM3 method, minimization by Amber generated somewhat bent adenosine allowing more contacts between the substituents at C-1' (adenine base) and C-5' (N-ethylcarboxamide) positions. The interiors of the PAMAM dendrimer had a relatively large volume-spacious enough to afford several internalized ligands simultaneously. The overall shape of the dendrimer conjugates were somewhat ellipsoidal, mostly governed by the shape of the ethylenediamine core. Hydrogen-bonds were detected in both structures, but not significantly less from the PAMAM-CGS21680 conjugate 17 (18 hydrogen-bonds) than from the PAMAM-APEC conjugate 66 (20 hydrogen-bonds) with thiourea groups which can additionally participate in the hydrogen-bond formation. As anticipated, generally adenosine moieties—key to the receptor binding—were located in close proximity to the PAMAM region for the PAMAM-CGS21680 dendrimer 17 compared to the APEC dendrimer 66. One internalized APEC ligand was detected after minimization from the PAMAM-APEC conjugate 66 while no internalized ligand was found from the minimized structure of PAMAM-CGS21680 dendrimer 17. The PAMAM-APEC dendrimer 66 with a longer linker indeed had a longer average diameter compared to the PAMAM-CGS21680 dendrimer 17. The estimated diameters of PAMAM conjugates ranged ca. 90-110 Å for APEC and ca. 65-85 Å for CGS21680. The variation (ca. 20 Å) in diameter within one dendrimer type possibly resulted from their ellipsoidal shape.

In Vitro Binding Assay of PAMAM Conjugates. The binding affinities of three PAMAM-APEC conjugates, 8, 9, and 10, at each $A_1$, $A_{2A}$, or $A_3$ AR, were measured using a standard radioligand competition experiment in a membrane suspension expressing a specific AR subtype.

Here, the $K_i$ values of PAMAM conjugates were measured as a concentration of the dendrimer. The binding results of the PAMAM-APEC conjugates, 8, 9, and 10, showed that the APEC ligand on the dendrimer is still able to bind to the $A_{2A}$ and $A_3$ ARs selectively, however, none of them was more potent than the APEC ligand 5 alone (overall 2-5 times less potent). Interestingly, binding of APEC 5 at the $A_1$ AR was nearly lost when this moiety was attached to the dendrimer. Binding at the $A_3$ AR was increased compared to the $A_{2A}$ AR when the APEC was attached to the dendrimer despite the fact that the APEC ligand 5 alone exhibited similar binding at both receptors. However, it is important to note that the APEC 5 contains a flexible primary amino group at the end of the linker region, and this may in fact greatly influence the ligand binding to the receptor. The $K_i$ value at the human $A_{2A}$ receptor of the APEC analogue 7, which was originally designed and synthesized to closely mimic the PAMAM-bound APEC moieties, was determined to be 70 nM.

Binding affinities of two other dendritic controls, 1 and 12, both based on the G3 PAMAM structure were compared with those of the PAMAM-APEC conjugates. Dendrimer 1 is the commercial PAMAM G3 structure with 32 terminal amino groups. Dendrimer 12 was the precursor of the PAMAM-APEC conjugate 8, thus bearing 14 acetamide groups and one fluorescein unit on average, but no APEC moieties. Dendritic control 12 was chosen to prove the exhibited potency and selectivity, if any, of the PAMAM-APEC conjugates, 8, 9, and 10, towards the $A_{2A}$ and $A_3$ ARs, are indeed resulting from the attached APEC units. The control assay of 1 showed no binding at all three types of ARs. Interestingly, a weak binding of control 12 to the $A_3$ AR was detected, whereas no binding observed to both $A_1$ and $A_{2A}$ ARs. Here, the binding of 12 to the $A_3$ AR cannot be simply attributed to the fluorescein group which was relatively more accessible for binding in the absence of APEC moieties, as the binding affinities of 9 and 10—both high loads of APEC and mainly differ in the lack of a fluorescein derivative—were similar at the $A_3$ AR.

Figure 25:
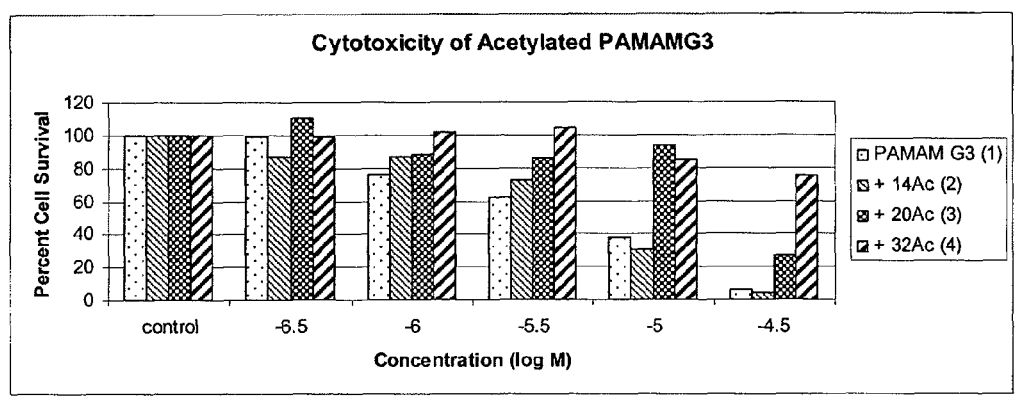
FIG. 25 depicts cytotoxicity data of acetylated PAMAM G3 dendrimers.
Figure 27:
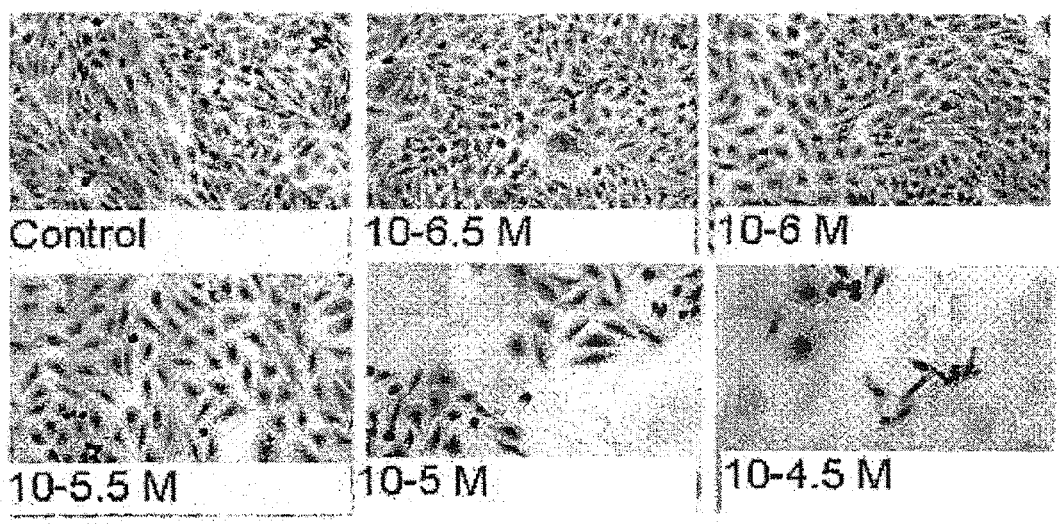
FIG. 27 depicts cytotoxicity data of PAMAM G3.5 in the form of micrographs.

In Vitro Cytotoxicity of Acetylated PAMAM, Anionic PAMAM, and PAMAM-PEG Conjugates. Cytotoxicity studies were performed on some of the commercial cationic and anionic PAMAM dendrimers, acetylated PAMAM dendrimers, 2 and 3 (FIG. 4), and ten PAMAM-PEG conjugates, 41-50 (Table 3). We started by examining the effects of acetylation for PAMAM dendrimers on cytotoxicity. FIGS. 25 and 27 show that PAMAM G3 1 with 32 primary amino groups was toxic at 30 µM. However, by acetylating 20 out of the 32 amino groups (3, FIG. 4) the toxicity was significantly reduced.

Figure 26:
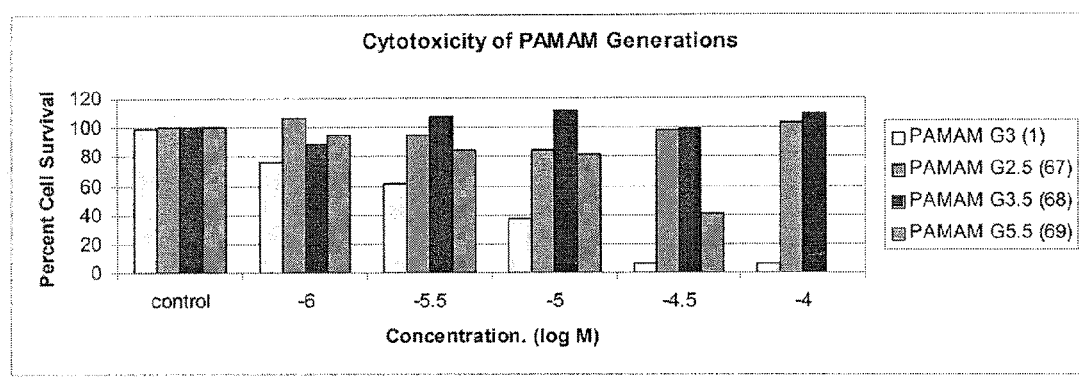
FIG. 26 depicts cytotoxicity data of carboxylate-terminated PAMAM dendrimers.
Figure 28:
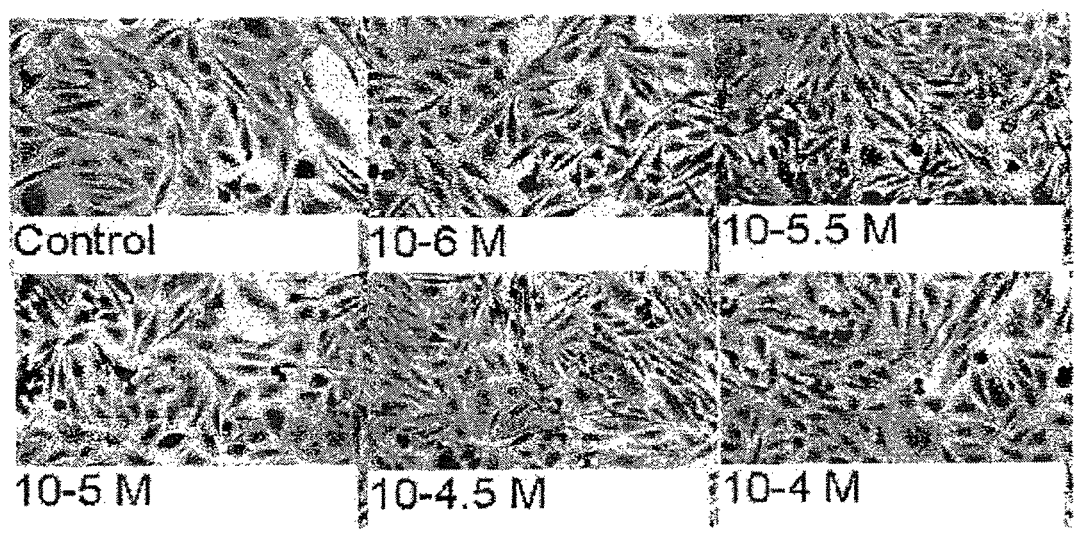
FIG. 28 depicts cytotoxicity data of PAMAM G2.5 in the form of micrographs.
Figure 29:
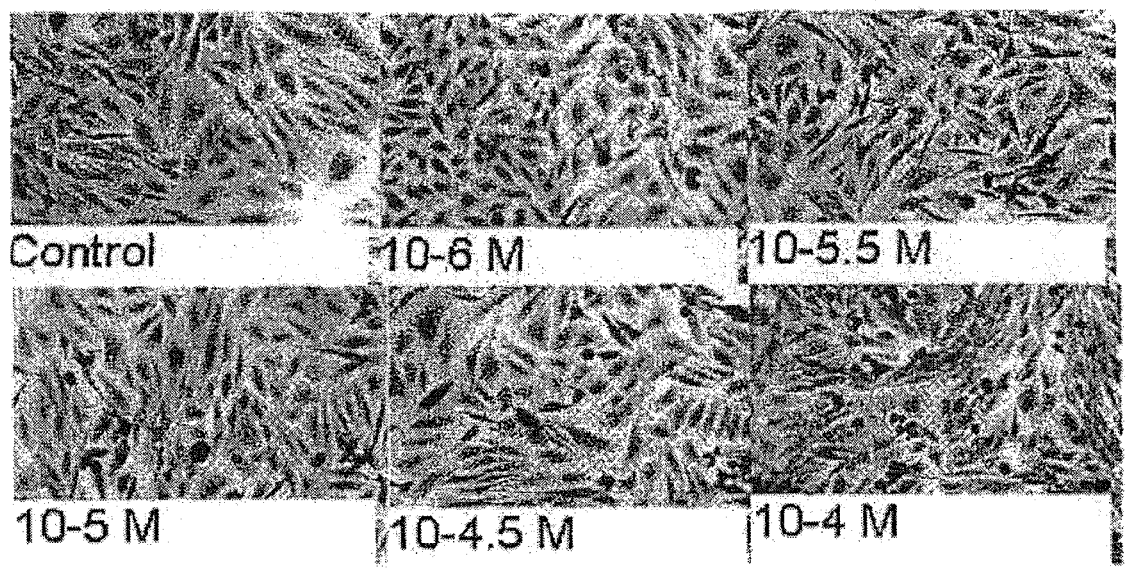
FIG. 29 depicts cytotoxicity data of PAMAM G3.5 in the form of micrographs.

FIGS. 26, 28, and 29 indicate that the carboxylate-terminated anionic PAMAM dendrimers were much less toxic compared to the PAMAM G3 dendrimer 1. As shown in FIGS. 26, 28, and 29, PAMAM dendrimer G2.5 (67, structure not shown) with ca. 32 terminal carboxylate groups, and PAMAM G3.5 dendrimer (68, structure not shown) with ca.

64 terminal carboxylate groups did not exhibit toxicity up to $10^{-4}$ M. PAMAM G5.5 dendrimer (69, structure not shown) with ca. 256 terminal carboxylate groups, was also less toxic than amine-terminated PAMAM G3 dendrimer 1. The increased cell death caused by the PAMAM G5.5 dendrimer 69 compared to the lower generation analogues, 67 and 68, may be due to the size effect, where the charge-induced aggregation was amplified.

Figure 30:
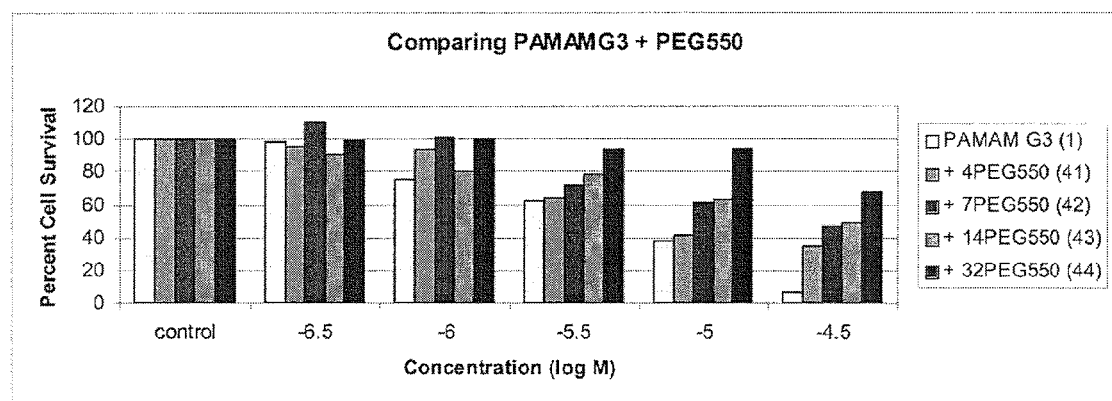
FIG. 30 depicts cytotoxicity data of PAMAM-PEG550 conjugates.
Figure 31:
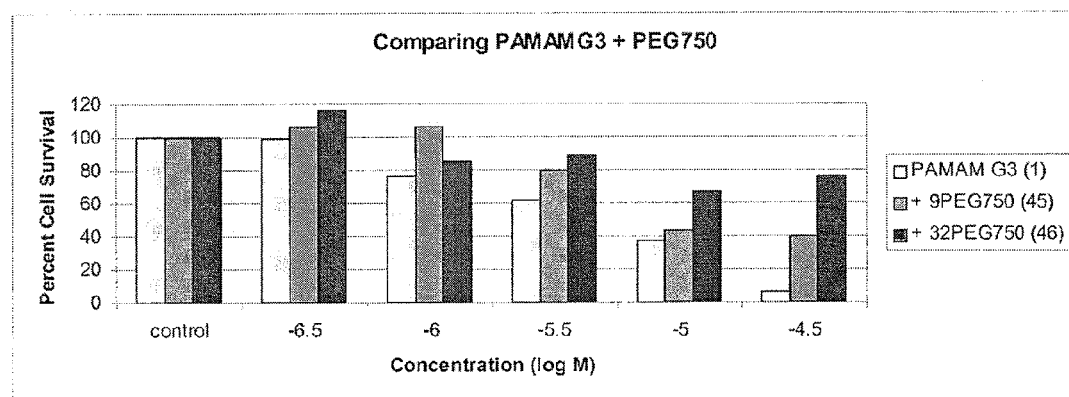
FIG. 31 depicts cytotoxicity data of PAMAM-PEG750 conjugates.
Figure 32:
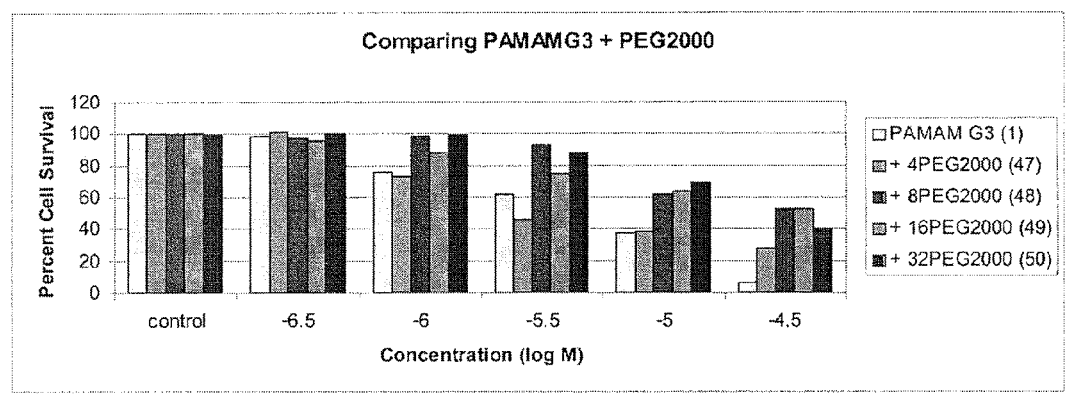
FIG. 32 depicts cytotoxicity data of PAMAM-PEG2000 conjugates.

Subsequently, PAMAM-PEG conjugates 41-50 containing varying amounts of $PEG_{550}$, $PEG_{750}$, or $PEG_{2000}$ were tested for cytotoxicity (FIGS. 30-32). While the addition of PEG groups decreased toxicity in general, the toxicity for PAMAM G3 1 with 32 PEG groups of any chain length was still greater than that of 1 with the same number of carboxylate or acetamide groups at 30 μM. The addition of more PEG units improved cell survival with the exception of high concentrations of $PEG_{2000}$. Overall, there was not a significant difference when the chain length of the PEG was compared to the amount of toxicity. In summary, in order to impose a minimum steric load on the ligand-receptor binding, low substitution of $PEG_{550}$ on a PAMAM dendrimer appears to be an ideal choice.

Once bound to the target receptor, dendrimer-ligand conjugates exhibit an enhancement in potency and/or selectivity through the multivalent synergistic effect and the steric inhibition to block the access of small ligand competitors. Due to the polyvalent nature of the dendrimer conjugate, the receptor binding kinetics is favorable, i.e. faster on-rate and slower off-rate.

Binding affinities of PAMAM-APEC conjugates exhibited $K_i$ values in the range of 42-152 nM-slightly weaker than the monovalent APEC 5—at the $A_{2A}$ and $A_3$ ARs with preserved or enhanced selectivity in comparison to the $A_1$ AR. Furthermore, the binding results suggested that the selectivity of APEC toward the $A_3$ AR was enhanced when this ligand was attached to the PAMAM dendrimer. In order to evaluate the true agonistic value of the dendrimer-bound APEC, and to assess the therapeutic potential of our multivalent dendrimer conjugates, functional assays on engineered cells expressing each AR subtype need to be completed in the near future.

Secondly, in an effort to reduce the cytotoxicity and to improve the water-solubility of amine-terminated PAMAM dendrimers, we prepared a series of PAMAM-PEG conjugates differing in chain lengths (PEG550, PEG750, and PEG2000) and the number of attachments to the PAMAM surface. Our cytotoxicity studies performed using cell culture experiments with surface-modified PAMAM dendrimers showed the greatest improvement in reducing cytotoxicity when the terminal amino groups were converted into acetamide groups. Cytotoxicity was reduced to a lesser degree when the amino groups were modified into carboxylate or PEG groups.

EXAMPLE 2

This Example illustrates the properties of some of the dendrimer conjugates of adenosine receptor agonists in accordance with an embodiment of the invention. The binding affinity at $A_1$, $A_{2A}$, and $A_3$ adenosine receptors is set forth in Tables 3-4.

TABLE 3

Binding and functional assay results at human $A_1$, $A_{2A}$, and $A_3$ ARs expressed in CHO cells.[a]

| | $K_i$ (nM) | | | $EC_{50}$ (nM) | |
|---|---|---|---|---|---|
| compound | $hA_1$ AR | $hA_{2A}$ AR | $hA_3$ AR | $hA_{2A}$ AR | $hA_3$ AR |
| 1 | n.d.[b] | n.d.[b] | n.d.[b] | n.d.[b] | n.d.[d] |
| 5 | 168 ± 36 | 29 ± 5 | 38 ± 11 | 8.2 ± 1.7 | 170 ± 90 |
| 7 | 840 ± 100 | 70 ± 3 | n.d.[d] | n.d.[d] | 375 ± 40 |
| 8 | (36 ± 13)%[c] | 152 ± 31 | 42 ± 5 | n.d.[d] | n.d.[d] |
| 9 | (32 ± 20)%[c] | 96 ± 20 | 55 ± 22 | n.d.[d] | n.d.[d] |
| 10 | (44 ± 13)%[c] | 130 ± 16 | 69 ± 26 | n.d.[d] | n.d.[d] |
| 12 | n.d.[b] | n.d.[b] | (52 ± 2)%[c] | n.d.[d] | n.d.[d] |
| 14 | 5780 ± 590 | 67 ± 19 | 247 ± 79 | 53 ± 16 | n.d.[d] |
| 16 | 984 ± 223 | 110 ± 15 | 58 ± 24 | 51 ± 8 | 725 ± 110 |

[a]Values are presented as the mean ± SEM of three or more independent experiments. $K_i$ values are reported for the binding assay, and $EC_{50}$ values are reported for the functional assay. For functional assays, see calcium protocol in the experimental procedure section.
[b]n.d. = not determined. No binding was detected under the given assay conditions.
[c]Measured as a percent inhibition at 10 μM.
[d]n.d. = not determined. Binding (or functional) experiment was not conducted.

TABLE 4

Affinity in binding ($K_i$) at four subtypes of human ARs and potency in activation ($EC_{50}$) of the the $hA_{2A}$ AR by small nucleosides and dendrimer derivatives.[a]

| Compound | $hA_{2A}$, $K_i$ (nM) | $hA_{2A}$, $EC_{50}$ (nM) | $hA_1$, $K_i$ (nM) or % inhibition at 1 μM | $hA_3$, $K_i$ (nM) or % inhibition at 1 μM |
|---|---|---|---|---|
| CGS21680 | 67 ± 19 | 52.6 ± 15.7 | 5780 ± 590 | 247 ± 79 |
| APEC | 12 ± 6 | FA | 168 ± 36 | 38 ± 11 |
| MRS5096 | 210 ± 19 | FA | 984 ± 223 | 58 ± 24 |
| MRS5130 | NA | NA | NA | NA |
| MRS5131 | NA | NA | 14 ± 5% | NA |
| MRS5132 | NA | NA | NA | NA |
| MRS5135 | 488 ± 59 | FA | 12 ± 2% | 24 ± 7% |
| MRS5136 | 496 ± 18 | FA | 19 ± 4% | 28 ± 3% |
| MRS5137 | 752 ± 34 | FA | 13 ± 3% | 25 ± 4% |
| MRS5138 | 215 ± 12 | 60.6 ± 12.8 | 4230 ± 1310 | 24 ± 8% |
| MRS5139 | 151 ± 36 | 11.2 ± 4.9 | 4870 ± 1360 | 1130 ± 310 |

[a]Radioligand binding determined in CHO cell membranes ($A_1$ AR) or in HEK293 cell membranes ($A_{2A}$ AR), as described in Materials and methods. Stimulation of adenylate cyclase measured in HEK293 cells stably expressing the $A_{2A}$ AR. Binding affinity is expressed as $K_i$ ± SEM values, unless noted. If a precent is given, it refers to inhibition of binding or activation of adenylate cyclase in comparison to the full agonist NECA. The effect of 10 μM NECA = 100%.
[b]Compound 6 at 10 μM inhibited binding at the $hA_{2A}$ AR by 58 ± 2%.
NA Not active, i.e., <10% inhibition of radioligand binding or stimulation of adenylate cyclase at 1 μM. All derivatives were NA in binding to the human $A_{2B}$ AR.
FA Full agonist at 10 μM with >90% of effect of NECA.

Figure 33:
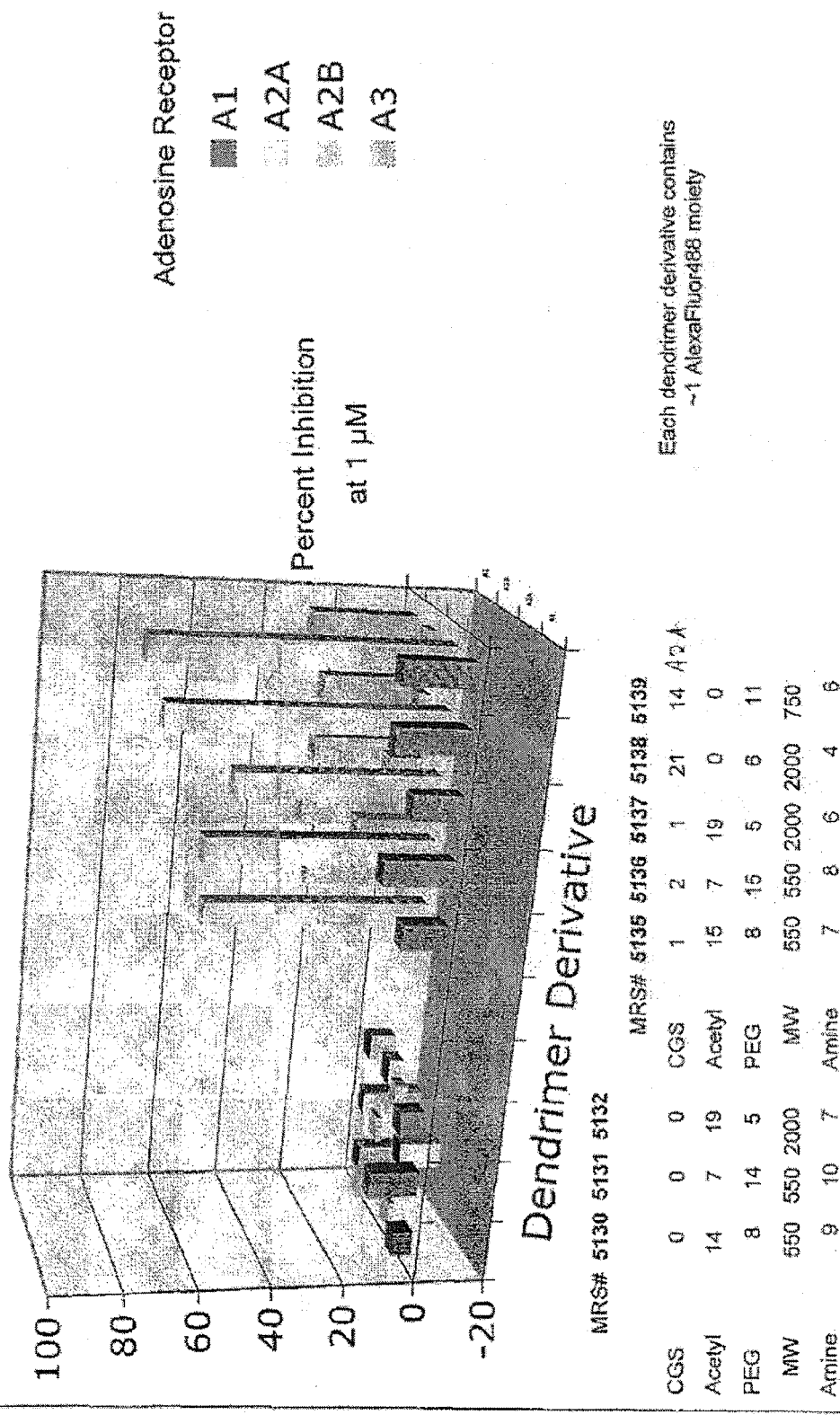
FIG. 33 depicts adenosine receptor binding data for PAMAM dendrimer conjugates in accordance with an embodiment of the invention.
Figure 34:
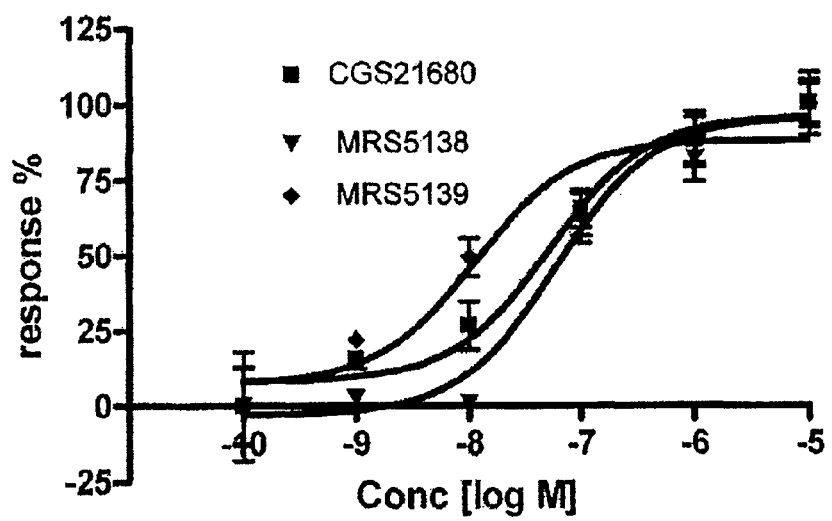
FIG. 34 depicts activation of A2A adenosine receptor by PAMAM dendrimer conjugates in accordance with an embodiment of the invention.

The percent inhibition of adenosine receptor binding is shown in FIGS. 33-34.

EXAMPLE 3

Figure 35A:
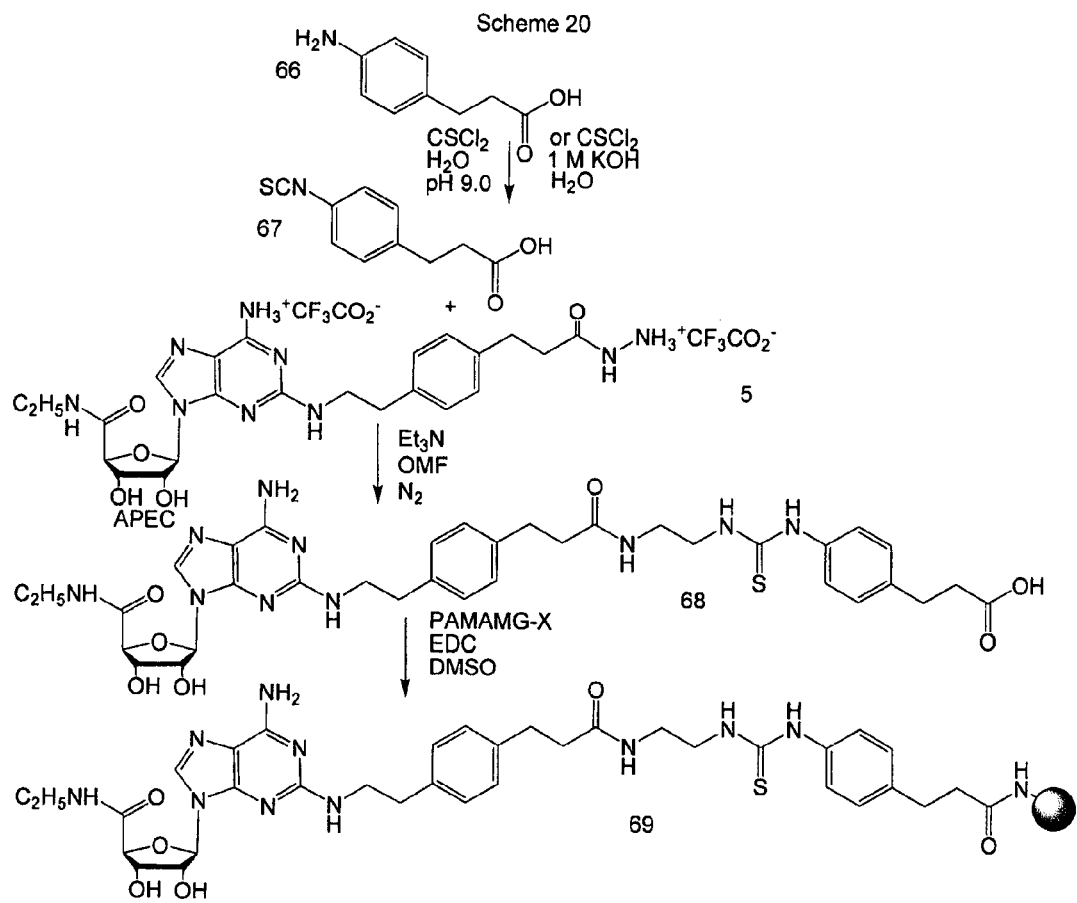
FIG. 35 depicts Schemes 20 and 21, reaction schemes to link adenosine receptor agonists to PAMAM dendrimers in accordance with an embodiment of the invention.
Figure 35B:
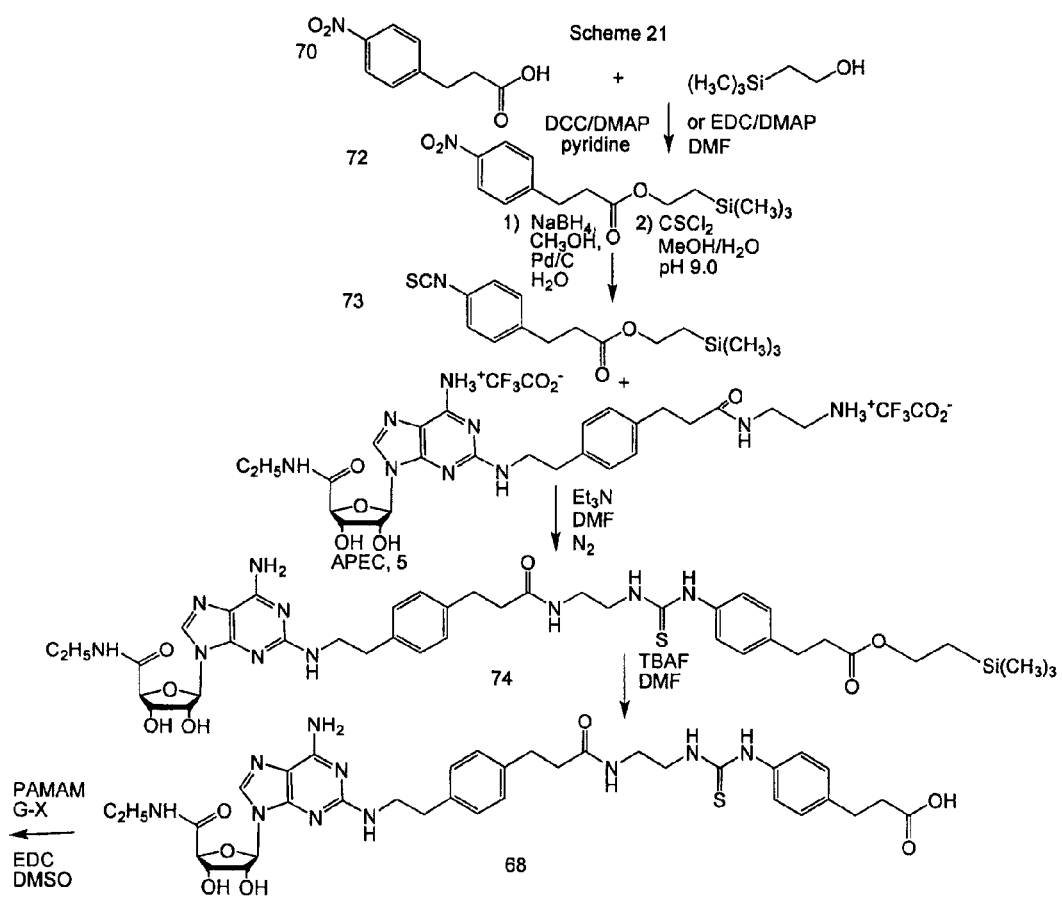

This Example illustrates an alternate linkage of adenosine receptor agonists to dendrimers. Attachment of 4-(3-carboxypropyl)phenylaminothiocarbonyl-APEC to PAMAMG-X:

A new APEC carboxylic acid functionalized congener 68 is synthesized for attachment to various generations of PAMAM dendrimers. This derivative uses an isothiocyanato attachment to APEC, which was shown in model compounds to enhance receptor affinity, and an amide coupling attachment to the dendrimer. One synthesis of compound 68 and its attachment to the dendrimer to form conjugate 69 is shown in Scheme 20, FIG. 35. The intermediate 3-(4-Isothiocyanatophenyl) propanoic acid 67 is made from 3-(4-aminophenyl)propanoic acid, which is commercially available from Pfaltz and Bauer. To form the isothiocyanate group from the p-amino group, a basic solution (pH 8.5-9.0) of thiophosgene is used, and the product 67 is purified on a silica gel column. Alternatively, the amino group is acylated using thiophosgene in a one molar aqueous solution of potassium hydroxide (KOH), and the product is purified by crystallizing and washing with water. An alternate route to form the isothiocyanate derivative 67 begins with 3-(4-nitrophenyl)propanoic acid 70 as shown in Scheme 21, FIG. 35. First, the carboxylic acid is protected as a stable trimethylsilylethyl (TMSE) alkyl ester 72 by a carbodiimide reaction with 2-trimethylsilylethanol 71. One method to form the ester uses dicyclohexylcarbodiimide (DCC) and 4-dimethylaminopyridine (DMAP) in pyridine and can be purified by flash chromatography. Alternatively, the ester can be formed using the water-soluble 1-(3-dimethylaminopropyl)-3-ethylcarbodiimide (EDC) and DMAP in dimethylformamide (DMF). The nitro group of 72 can then be reduced using sodium borohydride ($NaBH_4$) in methanol (MeOH) in a suspension of 10% palladium on carbon (Pd/C) in water. The resulting p-amino group can react with thiophosgene in a sodium bicarbonate ($NaHCO_3$) solution of methanol/water to form the isothiocyanate 73, which can be purified by HPLC. Once a 3-(4-isothiocyanatophenyl) propanoic acid derivative (with or without the TSME protecting group) is purified, 67 or 73, respectively, it will be attached to 2-[(2-aminoethylaminocarbonylethyl)phenylethylamino}-5'N-ethylcarboxamidoadenosine (APEC, 5) through reaction of the isothiocyanate group and the free amine at the 2 position chain of APEC. Triethylamine is necessary to remove the trifluoracetic acid (TFA) present in the commercially available salt form of APEC. The reaction takes place in isopropanol/acetonitrile under nitrogen gas. Alternately, the TMSE protecting group is removed using tetrabutylammonium fluoride (TBAF) in DMF, and the product can be purified by HPLC. The 4-(3-carboxypropyl)phenylaminothiocarbonyl-APEC 68 is attached to various generations of PAMAM dendrimers using a condensation reaction with EDC in dimethylsulfoxide (DMSO). The conjugate is purified by dialysis and gel permeation chromatography (GPC), and fluorescent ligands may also be attached. These compounds are suitable pharmacologically in binding and functional assays.

Dendrimers (all $3^{rd}$ generation PAMAM dendrimers):

| | |
|---|---|
| MRS5054 (8): | single fluorescein moiety, low loading of DITC-APEC in thiourea linkage, partially acetylated periphery |
| MRS5055 (9): | single fluorescein moiety, high loading of DITC-APEC in thiourea linkage |
| MRS5056 (10): | non-fluorescent, high loading of DITC-APEC in thiourea linkage |
| MRS5057 (4): | non-fluorescent, no DITC-APEC, fully acetylated periphery |
| MRS5059 (12): | single fluorescein moiety, no DITC-APEC, partially acetylated periphery |
| MRS5094 (17): | single Alexa Fluor 488 moiety, high loading of CGS21680 in amide linkage |

Methods:

Preparation of Human Washed Platelets

Human washed platelets were prepared as previously described (Cazenave et al., 2004). Briefly, fresh blood obtained from healthy donors was centrifuged at 175×g for 15 min at 37° C. and platelet rich plasma was removed and centrifuged at 1570×g for 15 min at 37° C. The platelet pellet was washed twice in Tyrode's buffer (137 mM NaCl, 2 mM KCl, 12 mM $NaHCO_3$, 0.3 mM $NaH_2PO_4$, 1 mM $MgCl_2$, 2 mM $CaCl_2$, 5.5 mM glucose, 5 mM Hepes, pH 7.3) containing 0.35% human serum albumin and finally resuspended at a density of $3 \times 10^5$ platelets/µl in the same buffer in the presence of 0.02 U/ml of the ADP scavenger apyrase (adenosine 5'-triphosphate diphosphohydrolase, EC 3.6.1.5), a concentration sufficient to prevent desensitization of platelet ADP receptors during storage. Platelets were kept at 37° C. throughout all experiments.

Platelet Aggregation Studies

Aggregation was measured at 37° C. by a turbidimetric method in a dual-channel Payton aggregometer (Payton Associates, Scarborough, Ontario, Canada). A 450 µl aliquot of platelet suspension was stirred at 1100 rpm and activated by addition of various agonists [adenosine 5'-diphosphate (ADP) or the TRAP peptide], in the presence or absence of the dendrimer and in the presence of human fibrinogen (0.8 mg/ml), in a final volume of 500 µl. The extent of aggregation was estimated quantitatively by measuring the maximum curve height above baseline level.

Functional Assay

Human washed platelets ($3 \times 10^5$ platelets/µl) were incubated with the dendrimer or with DMSO for 5 min. Platelets were then washed twice (to remove the dendrimer from the extracellular medium) and resuspended in Tyrode's albumin buffer at the same density. Aggregation was induced either with the mixed $P2Y_{1/12}$ receptor agonist ADP (5 µM), an agent which does not induce the granule release reaction, or with TRAP (0.125 or 0.25 µM), which activates the protease-activated receptor 1 (PAR-1) thrombin receptor and induces the granule release reaction.

Fluorescent Confocal Microscopy Analysis

Human washed platelets ($3 \times 10^5$ µl) resuspended in Tyrode's buffer containing 0.35% albumin were incubated for increasing periods of time (5, 15, 30 or 60 min) with the dendrimer or with DMSO. Platelets were then washed, resuspended in the same buffer and fixed with paraformaldehyde 2%. Platelets were then seeded on poly-L-lysine coated glass coverslips. After washing, the coverslips were mounted in Mowiol 4-88 and examined under a Leica laser confocal scanning microscope (Leica SP5) equipped with a plan apo oil immersion lens (×63, n.a.=1.4, or ×100, n.a.=10.3). In some experiments, the adherent platelets were permeabilized with saponin 0.05% in PBS containing 0.01% bovine serum albumin for 30 min and incubated with a rabbit anti-human von Willebrand factor (vWF) polyclonal antibody (10 µg/ml) (Dako, Denmark) for 30 min at room temperature followed by a goat anti rabbit alexa-555 nm polyclonal antibody for 30 min. The coverslips were then washed thoroughly and mounted in Mowiol.

Figure 36:
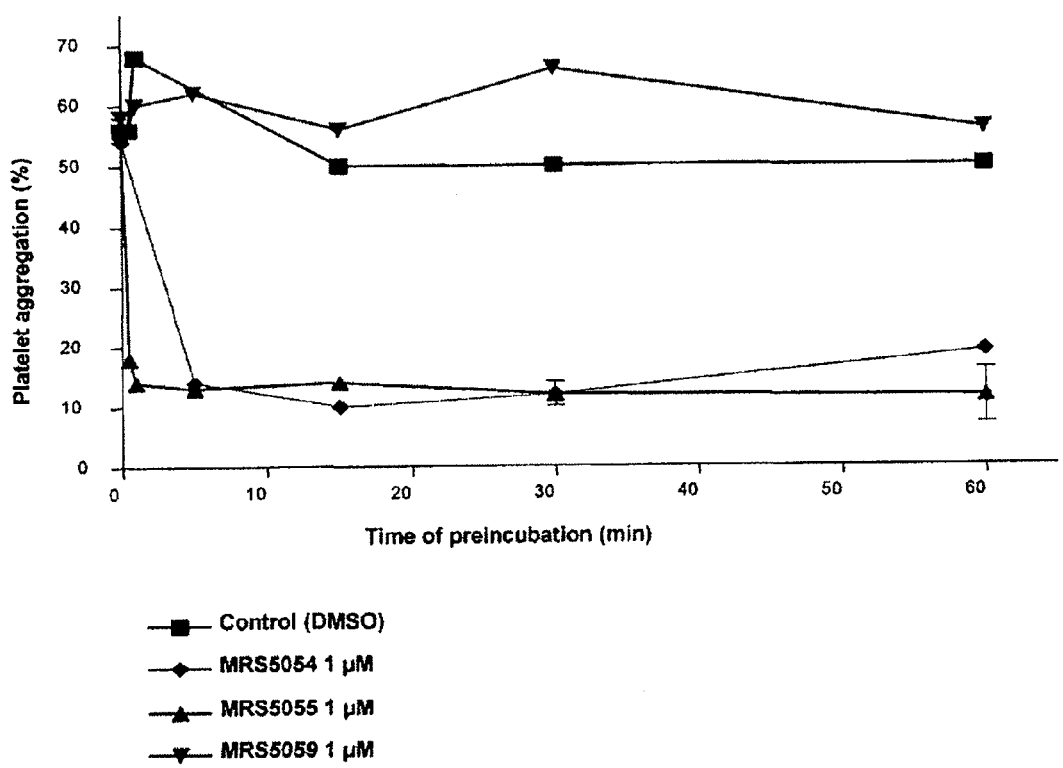
FIG. 36 depicts platelet aggregation data for certain dendrimer conjugates in accordance with embodiments of the invention.

Results Concerning MRS5054, MRS5055, and MRS5059 (FIG. 36):

MRS5054 (1 μM) or MRS5055 (1 μM) inhibited aggregation of human washed platelets induced by ADP (5 μM), while MRS5059 (1 μM) had no inhibitory effect.

Fluorescent confocal microscopy analyses were performed in order to determine whether these compounds could be internalized by platelets. MRS5059 (1 μM) was localized inside platelets after 5 min of incubation with human washed platelets. Almost no fluorescence could be detected at the later incubation times (15, 30, and 60 min). MRS5054 (0.1 μM) and MRS5055 (1 μM) were never found inside the cells.

In order to determine whether MRS5059 was localized in alpha granules, a double fluorescent staining was performed with von Willebrand Factor (vWF), a protein specifically stored in platelet alpha granules. No colocalization between vWF and MRS5059 could be detected.

Fluorescein-conjugated PAMAM dendrimers loaded with DITC-APEC (MRS5054, MRS5055) were not found inside platelets, while fluorescein-conjugated PAMAM dendrimer without DITC-APEC (MRS5059) was internalized by platelets. However, the fluorescence could be detected only after a short incubation time with platelets (5 min) and this fluorescence was low.

Figure 37:
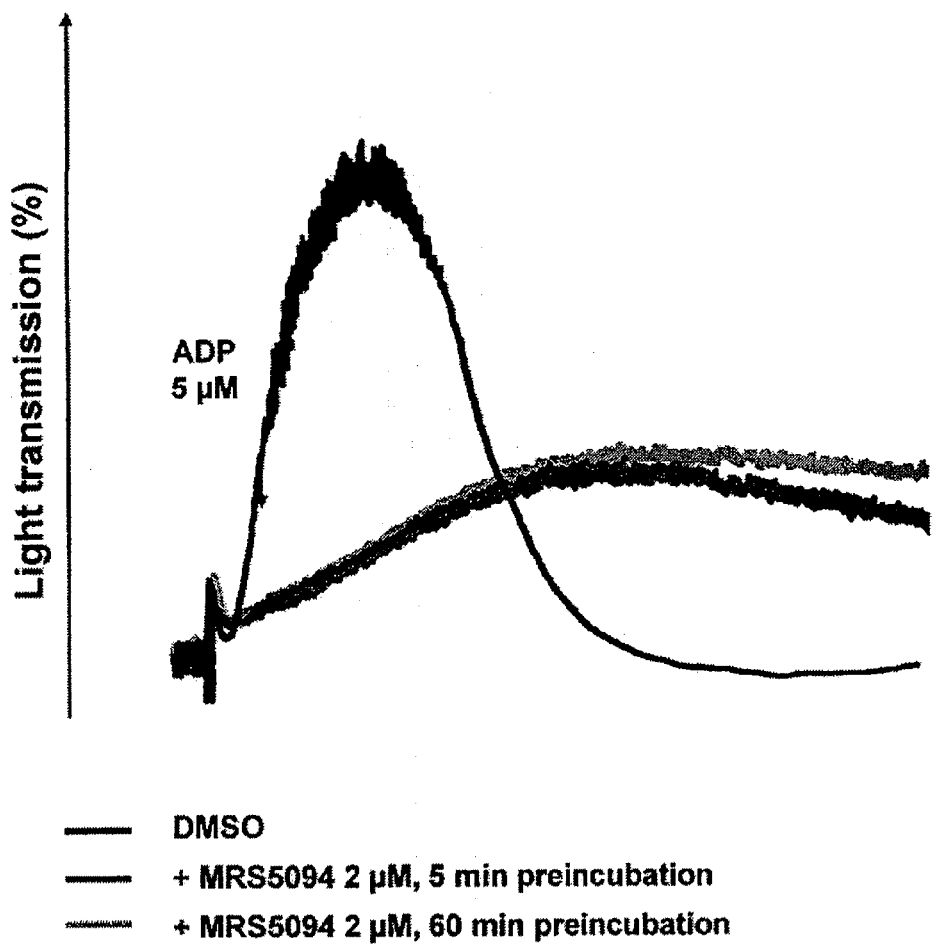
FIG. 37 depicts light transmission data for platelet aggregation prevention by a dendrimer conjugate in accordance with an embodiment of the invention.
Figure 38:
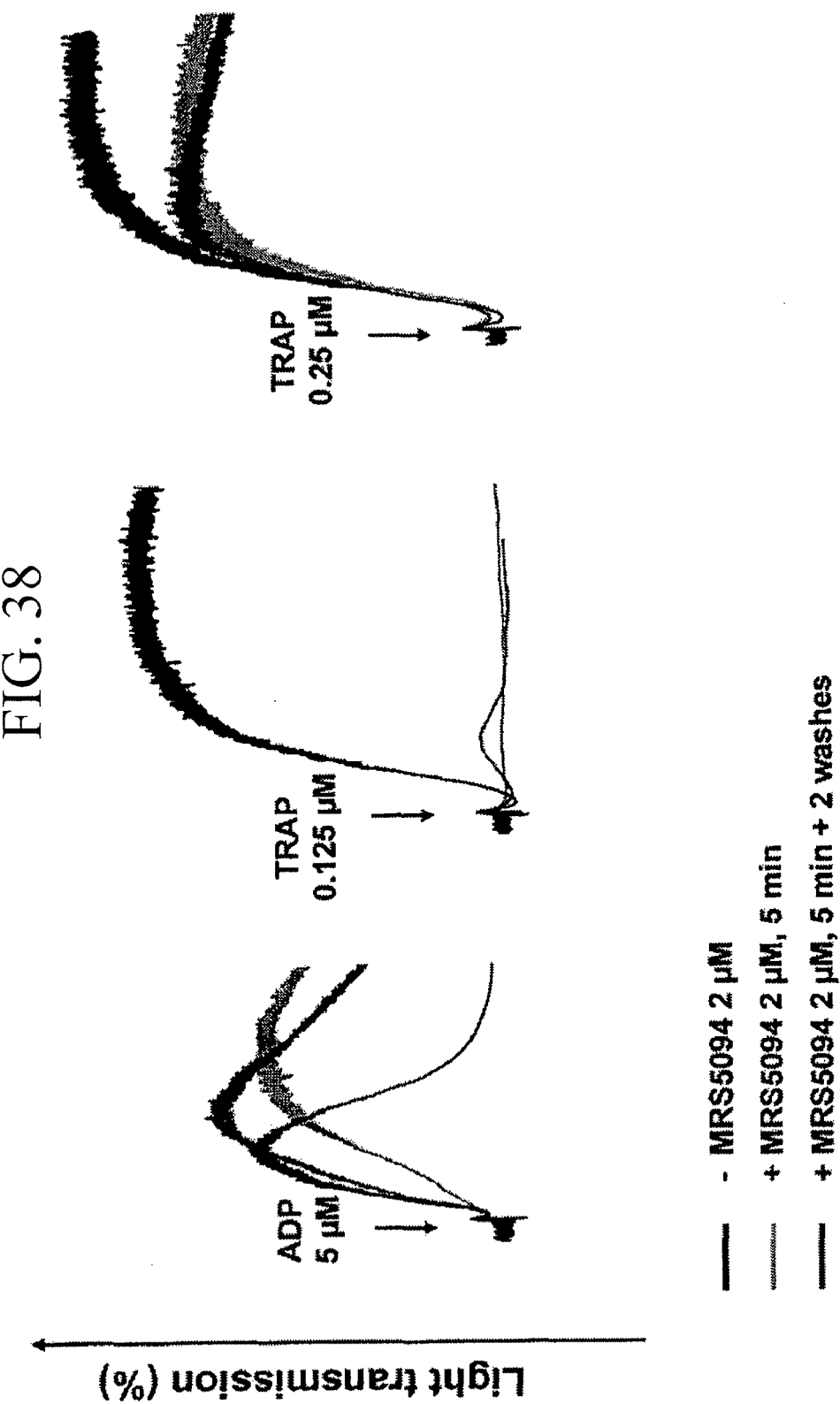
FIG. 38 depicts light transmission data for platelet aggregation prevention by another dendrimer conjugate in accordance with an embodiment of the invention.
Figure 39:
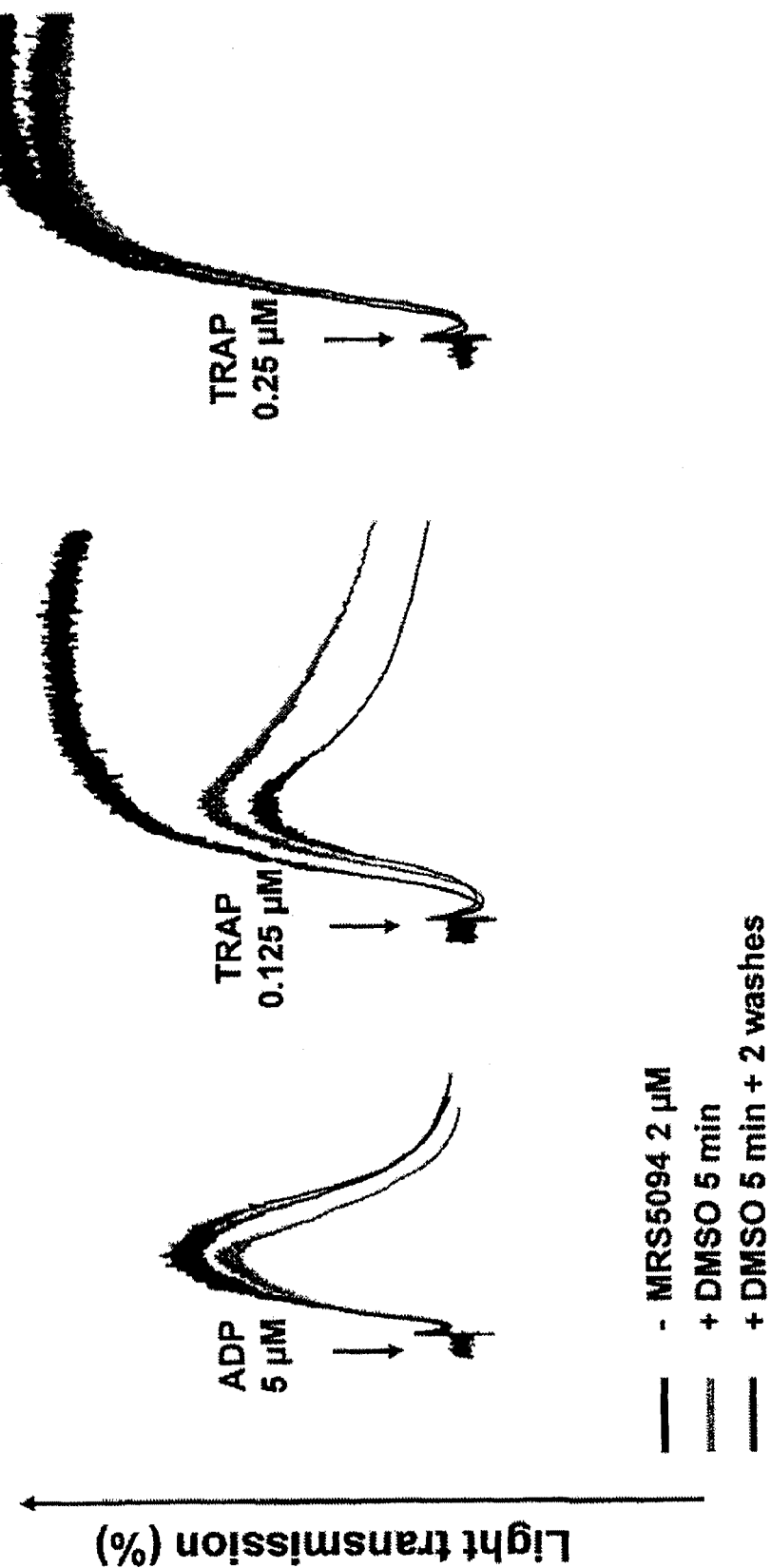
FIG. 39 depicts light transmission data for platelet aggregation prevention by a dendrimer conjugate and DMSO in accordance with an embodiment of the invention.

Results Concerning the Amide-Linked Conjugate of CGS21680 (Dendrimer Conjugate MRS5094, FIG. 37-39):

MRS5094 was prepared as a 500 μM stock solution in DMSO and was added directly to the platelet suspension to a final concentration of 2 μM. Control experiments were performed with DMSO diluted to the same extent. MRS5094 (2 μM) inhibited aggregation of human washed platelets induced by ADP (5 μM).

Fluorescent confocal microscopy analysis: MRS5094 (2 μM) was clearly found inside platelets after 5, 15, 30 or 60 min of incubation with human washed platelets. The fluorescence was very strong and appeared to be localized in vesicles, which were only present when platelets were incubated with MRS5094 but not with DMSO.

In order to determine whether MRS5094 could inhibit platelet aggregation following secretion from activated platelets, a functional assay was performed as described in the method section. Platelet aggregation induced by ADP (5 μM) was restored after the two washing steps. In contrast, aggregation induced by TRAP (0.125 μM or 0.25 μM) remained inhibited. This result suggests that MRS5094 (2 μM, 5 min), once incorporated into platelets, could be released in response to platelet activation by TRAP.

The foregoing shows that PAMAM dendrimer loaded with CGS21680 (MRS5094) enters platelets. MRS5094, once incorporated into platelets, is released and inhibits aggregation following platelet activation by TRAP.

EXAMPLE 4

This Example illustrates preparation and properties of dendrimer conjugates comprising $A_1$ adenosine receptor agonists in accordance with an embodiment of the invention.

Figure 40:
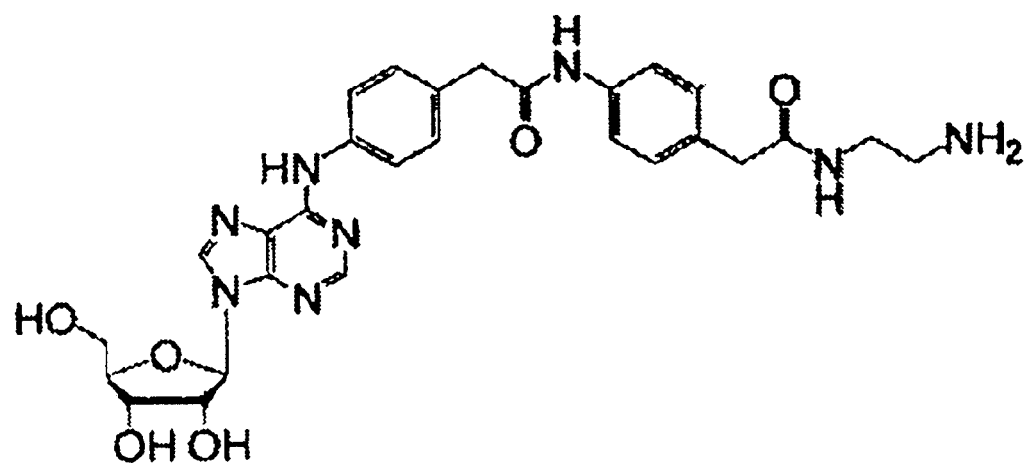
FIG. 40 depicts the structure of ADAC (101).

Two ADAC (101, FIG. 40) derivatives with side-chains containing either terminal amino or carboxyl groups were prepared. These derivatives were attached to G2.5 or G3 PAMAM dendrimers, respectively, and the difference in pharmacology of dendrimer conjugates of the different generations was determined. Derivatives of Alexa-Fluor 488 were also attached to the G3 and G2.5 dendrimers so that fluorescent and in vivo localization data were.
Materials and Methods
Materials $N^6$-[4-[[[4-[[[(2-Aminoethyl)amino]carbonyl]methyl]-anilino]carbonyl]methyl]phenyl]adenosine hydrate (ADAC), PAMAM dendrimer, ethylenediamine core, generation 3 solution (G3 PAMAM), PAMAM dendrimer, ethylenediamine core, generation 2.5 solution (2.5 PAMAM), 3-(4-aminophenyl)propionic acid, (Benzotriazol-1-yloxy)tripyrrolidinophosphonium hexafluorophosphate (PyBOP), 3-[(3-Cholamidopropyl)dimethylammonio]-1-propanesulfonate hydrate (CHAPS), adenosine deaminase, bovine serum albumin, sodium borate, Guanosine 5'-diphosphate sodium salt (GDP), N-(3-Dimethylaminopropyl)-N'-ethylcarbodiimide (EDC), dithiothreitol, ethylenediaminetetraacetic acid acetic anhydride (EDTA), 2-(N-Morpholino)ethanesulfonic acid (MES), magnesium chloride, sodium chloride, methanol, thiophosgene, triethylamine, diethyl ether, methyl sulfoxide-d6 (DMSO-d6), and N,N-dimethylformamide (DMF) were purchased from Sigma (St. Louis, Mo.). Bio-Beads® SX-1 beads were purchased from Bio-Rad (Hercules, Calif.). Alexa-Fluor® 488 carboxylic acid, 2,3,5, 6-tetrafluorophenyl ester, 5-isomer (AF488-TFP) was purchased from Invitrogen (Carlsbad, Calif.). 2-Chloro-$N^6$-cyclopentyladenosine ([$^3$H]CCPA, 42.6 Ci/mmol), and 2-[p-(2-carboxyethyl)phenylethylamino]-5'-N-ethylcarboxamidoadenosine ([$^3$H]CGS21680, 40.5 Ci/mmol) were purchased from Perkin Elmer (Waltham, Mass.). [$^{35}$S]GTPγS (1133 Ci/mmol) was purchased through GE Healthcare (Buckinghamshire, England). DMEM/F12 media and 1 M Tris-HCl (pH 7.5) were purchased from Mediatech. Bio-Bead SX-1 beads were purchased from Bio-Rad (Hercules, Calif.).

To prepare the size exclusion column (SEC), 100 g of SX-1 beads were dissolved in 1 L of DMF. After time for equilibration and expansion, the beads were added to the column as described previously. High Performance Liquid Chromatography (HPLC) purification was completed using an Agilent 1100 Series HPLC (Santa Clara, Calif.) equipped with a Phenomenex Luna 5μ C18(2) 100A analytical column (250× 10 mm; Torrance, Calif.). Peaks were detected by UV absorption using a diode array detector. Proton nuclear magnetic resonance spectra were recorded on a Bruker DRX-600 spectrometer after being optimized for each sample using DMSO-$d_6$ as a solvent unless otherwise noted. To determine the number of ligands attached to each dendrimer, the integration of the ligand was compared to the integration of one of the sets of carbon-protons on the interior of the dendrimer as described previously. Electrospray ionization mass spectra (ESI MS) were taken using a Waters LCT Premier mass spectrometer. Matrix Assisted Laser Desorption/Ionization Time-of-Flight spectra (MALDI-TOF) were obtained with a Waters Micro MS mass spectrometer using Waters MassPREP Direct Ionization on Silica Desorption/ionization (DIOS) target plates.

3-(4-Carbamothioylphenyl)propanoic acid (103)

Figure 41:
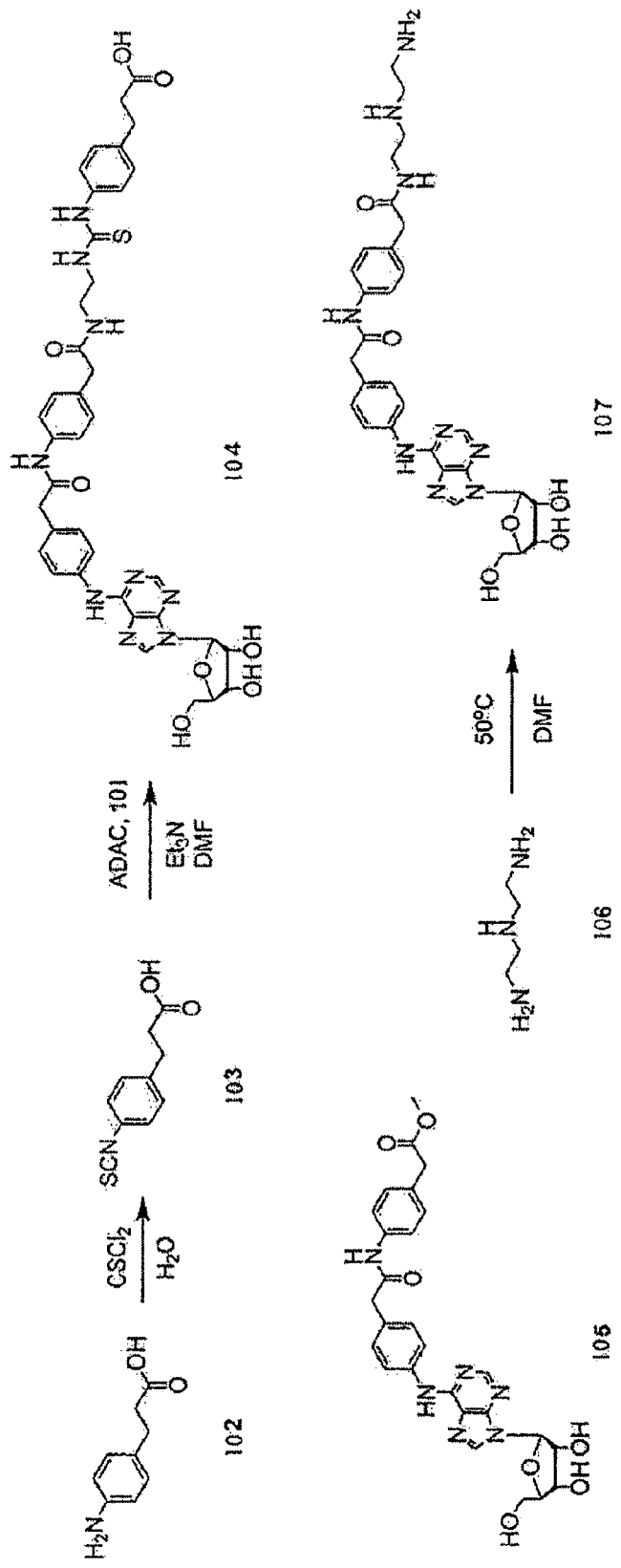
FIG. 41 depicts the structure of an ADAC congeners 104 and 107 and a method of preparing them.

3-(4-Aminophenyl)propanoic acid (102, FIG. 41) (100 mg, 670 μmol) was diluted in 0.7 ml of 0.8 M KOH. Thiophosgene (51.1 μl, 670 μmol) was diluted with 1.2 ml of water. The 3-(4-aminophenyl)propanoic acid was added dropwise to the thiophosgene solution. A solid immediately precipitated so an additional 4.2 ml of water was added. After 1 h, the solution was vacuum-filtered and vacuum-dried overnight to give 98.6 mg of 3-(4-carbamothioylphenyl)propanoic acid (475 μmol, 80% yield). $^1$H NMR (CDCl$_3$) 7.27-7.30 (m, 2H), 7.15-7.23 (m, 2H), 2.93 (t, J=7.9 Hz, 2H), 2.68 (t, J=7.4 Hz, 2H) m/z (M+ESI MS) calc: 208.0432 found: 208.0423.

4-(3-Carboxypropyl)phenylaminothiocarbonyl)-ADAC (104)

3-(4-Carbamothioylphenyl)propanoic acid (103) (12 mg, 60.7 µmol) and ADAC (101) (35 mg, 60.7 µmol) were dissolved in 4 ml of DMF. Triethylamine (20 µl, 143 µmol) was added, and the reaction was stirred for 1 h. The DMF was removed under nitrogen and the resulting oil was dissolved in methanol. Ether was added to precipitate the product. After removal of the supernatant and drying, the resulting product was judged homogenous by TLC and weighed 17.84 mg (22.8 µmol, 37% yield). $^1$H NMR (DMSO-$d_6$) 10.10 (s, 1H), 9.93 (s, 1H), 9.52 (br s, 1H), 8.53 (s, 1H), 8.37 (s, 1H), 8.10 (t, J=6.1 Hz, 1H), 7.85 (d, J=8.9 Hz, 2H), 7.66 (br s, 1H), 7.52 (d, J=8.5, 2H), 7.21-7.33 (m, 4H), 7.13-7.20 (m, 4H), 5.95 (d, J=6.0 Hz, 1H), 5.48 (d, J=5.5, 1H), 5.29 (t, J=5.6 Hz, 1H), 5.21 (d, J=4.6 Hz, 1H), 4.63 (m, 1H), 4.17 (m, 1H), 3.98 (dd, J=3.6, 4.0 Hz, 1H), 3.65-3.74 (m, 1H), 3.59 (s, 1H), 3.53 (m, 2H), 3.20-3.29 (m, 2H), 2.72-2.83 (m, 2H) m/z (M$^+$ ESI MS) calc: 784.2877 found: 784.2882.

N-(2-Aminoethyl)-ADAC (107)

This compound was synthesized according to a similar procedure to obtain ADAC. N$^6$-[4-[[[4-((2-methoxy)-2-oxy-ethyl)-anilino]carbonyl]methyl]phenyl]adenosine (105) (4.97 mg, 9.1 µmol) was dissolved in 1 ml of DMF. Diethylenetriamine (106) (150 µl, 1370 µmol) was added to this solution. The reaction stirred overnight, and the DMF was removed under nitrogen. The resulting oil was dissolved in methanol, and the solid was precipitated with ether. After removal of the supernatant, the remaining solid was dried overnight to give 3.75 mg of product (6.05 µmol, 66.5% yield). $^1$H NMR (DMSO-$d_6$) 10.11 (s, 1H), 9.94 (br s, 1H) 8.53 (s, 1H), 8.38 (s, 1H), 7.90-8.04 (m, 2H), 7.84 (d, J=9.0 Hz, 2H), 7.51 (d, J=7.6 Hz, 2H), 7.29 (d, J=8.4 Hz, 2H), 7.18 (d, J=8.8 Hz, 2H), 5.95 (d, J=6.9 Hz, 1H) 5.32 (m, 1H), 4.63 (t, J=5.7 Hz, 1H), 4.17 (t, J=4.8 Hz, 1H), 3.98 (dd, J=3.4 Hz, 2.1 Hz, 1H), 3.59 (m, 3H), 3.10-3.15 (m, 4H), 2.62 (m, 2H), 2.55 (s, 6H, 21, 22), 1.10 p (t, J=6.8 Hz, 3H). m/z (M$^+$ ESI MS) calc: 620.2945 found: 620.2931.

Figure 43:
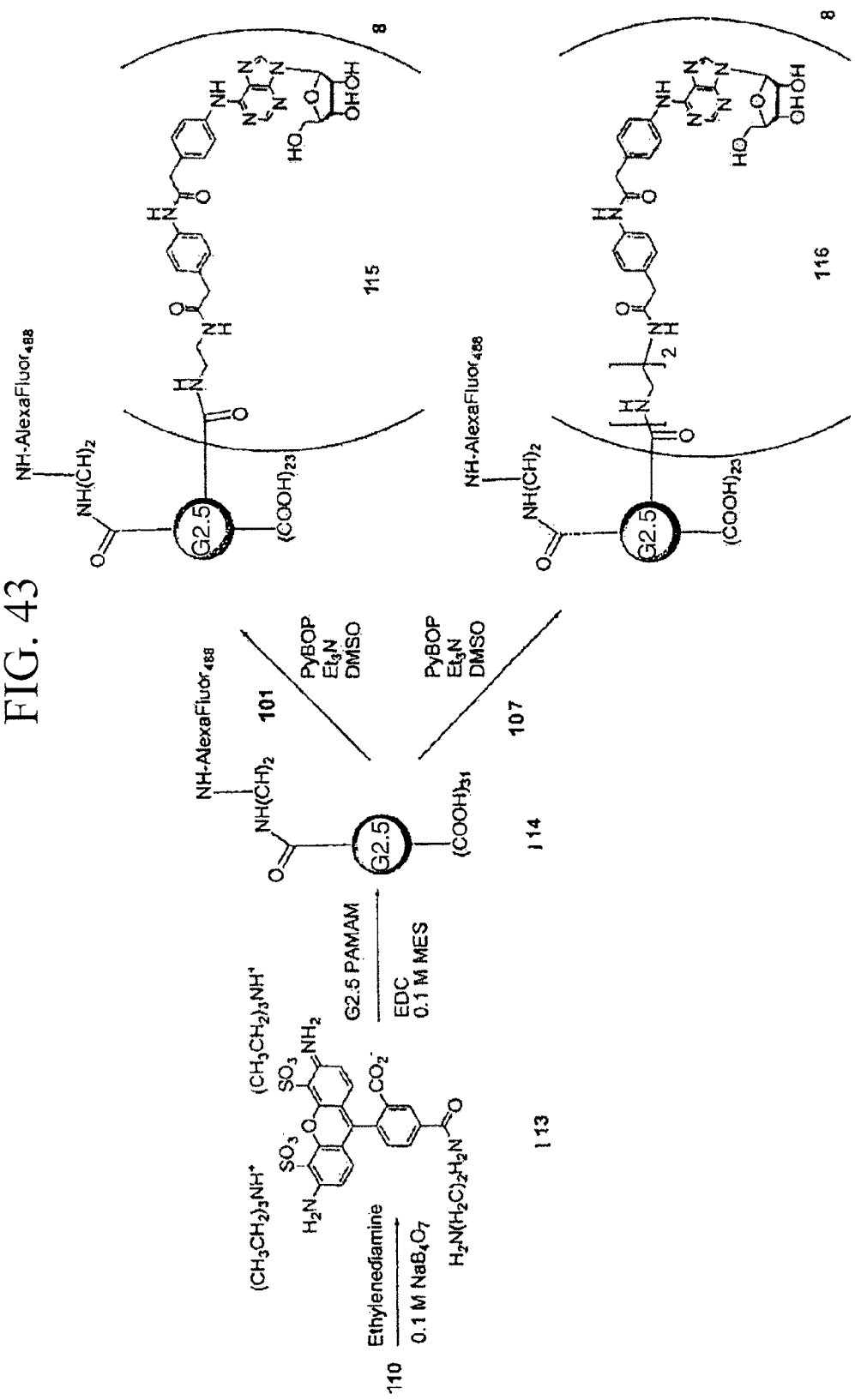
FIG. 43 depicts a method of preparing dendrimer conjugates 115-116 in accordance with an embodiment of the invention.

Alexa-Fluor 488-ethylenediamine (113, FIG. 43)

5 mg of AF488-TFP (110) (5.65 µmol) was dissolved in 280 µl of DMF. In order to provide a basic environment, 1500 µl of 0.1 M NaB$_4$O$_7$, pH 8.5 was added. 10 µl of ethylenediamine diluted with 210 µl of water was added, and the mixture stirred overnight. The product was purified by HPLC using the following water/acetonitrile linear gradient: 0 min, 0% acetonitrile; 25 min, 100% acetonitrile. The product eluted at 10.8 min. After lypholization, 3.02 mg of product (5.2 µmol) remained (93% yield). $^1$H NMR (D$_2$O) 8.33 (d, J=2.3 Hz, 1H), 8.17 (t, J=1.9 Hz, 1H), 7.90 (m, 1H), 7.24 (t, J=7.5, 1H), 7.16 (dd, J=7.5, 1.9, 1H), 7.08 (d, J=9.6, 2H), 6.83 (t, J=8.8, 4H), 3.63 (m, 1H), 3.51 (t, J=11.7, 2H), 3.40 (t, J=5.0, 2H), 3.13-3.21 (m, 2H) m/z (M$^-$ Na MALDI-TOF MS) calc: 597.0362 found: 597.0383.

G3 PAMAM-Ac-AF488 (111)

1 ml of G3 PAMAM methanol stock solution (18.8 mM, 18.8 µmol) from Sigma was added to a flask, and the methanol was evaporated. The remaining polymer was diluted in 1 ml of DMSO-$d_6$. Acetic anhydride (40.8 µl, 432 µmol, 23 eq) was diluted with 1 ml of DMSO-$d_6$, and the solution was added dropwise to the G3 PAMAM. After 18 h, an NMR showed approximately 23 acetamide groups per dendrimer, as expected, to give 109. 460 µl of this solution (4.32 µmol, 9.4 mM) was removed and diluted to 1460 µl with DMSO-$d_6$. Triethylamine (10 µl, 72 µmol) was added under a nitrogen atmosphere. AF488-TFP (110) (4 mg, 4.52 µmol, 1.05 eq) was dissolved in 400 µl of DMSO-$d_6$ and added to the mixture. After 48 hr, the solution was vacuum filtered to remove a small amount orange precipitate formed. The NMR spectrum was consistent with the assigned structure, but the signals resulting from AF488 could not be properly integrated due to the large G3 PAMAM peaks. Therefore, it was assumed that approximately one Alexa-Fluor 488 moiety was attached per G3 PAMAM based off of previous data.

G3 PAMAM-Ac-AF488-(4)(112)

660 µl of 111 (2.3 mM solution in DMSO-$d_6$, 1.52 µmol) was removed and placed under nitrogen gas. Compound 104 (11.8 mg, 15 µmol) was dissolved in 200 µl of DMSO and added to the mixture. Finally, triethylamine (28 µl, 202 µmol) and PyBOP (26 mg, 50 µmol) dissolved in 1.5 ml of DMSO were added. After 48 hr, the product was purified by SEC using DMF as the eluent. The collected fractions were dried and dissolved in DMSO-$d_6$ for NMR. The first and last fractions containing the product were removed to provide a more homogenous sample. The remaining fractions were added together and dried to give 8.68 mg of product, which contained on average 8 ADAC-COOH moieties per dendrimer (0.694 µmol, 46% yield based on µmol of dendrimer). $^1$H NMR (DMSO-$d_6$) 10.11 (s, 8H), 9.94 (s, 8H), 9.53 (s, 5H), 8.54 (s, 8H), 8.38 (s, 8H), 8.10 (t, J=6.0 Hz), 7.96 (s, 41H), 7.90 (s, 33H), 7.84 (m, 41H), 7.52 (d, J=8.6 Hz, 16H), 7.24 (d, J=8.3 Hz, 16H), 7.17 (m, 34H), 5.96 (d, J=6.2, 7H), 5.50 (br s, 4H), 5.31 (br s, 7H), 5.22 (br s, 5H), 4.64 (t, J=4.2 Hz, 8H), 4.18 (t, J=3.4 Hz, 8H), 3.99 (dd, J=2.7, 3.7, 8H), 3.70 (m, 11H), 3.59 (m, 44H), 3.08 (s, 176H), 2.90 (s, 8H), 2.74 (s, 9H), 2.65 (s, 120H), 2.43 (s, 77H), 2.19 (s, 120H), 1.80 (s, 69H).

G2.5 PAMAM-AF488 (114)

This procedure was adapted from a carbodiimide coupling described previously. 5 µmol of G2.5 PAMAM methanol stock solution (31.3 mg) from Sigma was added to a flask, and the methanol was evaporated off. The remaining polymer and compound 113 (3.0 mg, 5.2 µmol) were dissolved in 1.7 ml of 0.1 M MES buffer, pH 5. EDC (40.4 g, 260 µmol) was dissolved in 1 ml of 0.1 M MES buffer, pH 5, and the reaction stirred for 2 days. EDU, unreacted EDC, and unreacted 113 were removed through excessive dialysis. After dialysis with water, the compound was lyophilized and redissolved in 1 ml of DMSO-$d_6$ for NMR and further assays.

G2.5 PAMAM-AF488-1 (115)

300 µl of 114 (1.50 µmol) is removed and placed under a nitrogen atmosphere. ADAC (8.65 mg, 15 µmol) is dissolved in 200 µl of DMSO-$d_6$ and is added to the mixture. Finally, triethylamine (28 µl, 202 µmol) and PyBOP (26 mg, 50 µmol) dissolved in 1.5 ml of DMSO-$d_6$ are added. The reaction is monitored by NMR. After approximately 48 h, the product is purified by SEC using DMF as the eluent. The collected fractions are dried and dissolved in DMSO-$d_6$ for NMR. The first and last fractions containing the product are removed to provide a more homogenous sample. The remaining fractions are added together and dried to get around 8 mg of product, which should contain on average 8 ADAC per dendrimer.

G2.5 PAMAM-AF488-3 (116)

300 µl of G2.5 PAMAM-AF488 (1.50 µmol) is removed and placed under a nitrogen atmosphere. N-(2-aminoethyl)-ADAC (9.30 mg, 15 µmol) is dissolved in 200l of DMSO-$d_6$ and is added to the mixture. Finally, triethylamine (28 µl, 202 µmol) and PyBOP (26 mg, 50 µmol) dissolved in 1.5 ml of DMSO-$d_6$ are added. The reaction is monitored by NMR. After approximately 48 h, the product is purified by SEC using DMF as the eluent. The collected fractions are dried and dissolved in DMSO-$d_6$ for NMR. The first and last fractions containing the product are removed to provide a more homogenous sample. The remaining fractions are added together and dried to give approximately 8 mg of product, which should contain on average 8 N-(2-aminoethyl)-ADAC per dendrimer.

Cell Culture and Membrane Preparation

CHO (Chinese hamster ovary) cells expressing the recombinant human ARs were cultured in Dulbecco's modified Eagle medium (DMEM) and F12 (1:1) supplemented with 10% fetal bovine serum, 100 units/mL penicillin, 100 μg/mL streptomycin, and 2 μmol/mL glutamine. After harvesting, cells were homogenized and suspended. Cells were then centrifuged at 500 g for 10 min, and the pellet was resuspended in 50 mM Tris-HCl buffer (pH 7.5) containing 10 mM $MgCl_2$. The suspension was homogenized and was then recentrifuged at 20 000 g for 20 min at 4° C. The resultant pellets were resuspended in Tris buffer, incubated with adenosine deaminase for 30 min at 37° C., and the suspension was stored at −80° C. until the binding experiments. The protein concentration was measured using the Bradford assay.

[$^{35}$]GTPγS Binding

[$^{35}$S]GTPγS binding was measured in 200 μl of buffer containing 50 mM Tris-HCl (pH 7.4), 1 mM EDTA, 1 mM $MgCl_2$, 10 μM GDP, 1 mM dithiothreitol, 100 mM NaCl, 3 units/ml adenosine deaminase, 0.2 nM [$^{35}$S]GTPγS, 0.004% CHAPS, 0.5% bovine serum albumin and increasing concentrations of the ligands. Samples were started by addition of the membrane suspension (5-10 μg protein/tube) to the test tubes and incubated at 25° C. for 30 min. The assay was terminated by rapid filtration through Whatman GF/B filters, pre-soaked in 50 mM Tris-HCl (pH 7.4) containing 5 mM $MgCl_2$ and 0.02% CHAPS. Non-specific binding of [$^{35}$S] GTPγS was measured in the presence of 10 μM unlabelled GTPγS. After the filters were washed, they were placed in scintillation vials containing 5 mL of Hydrofluor scintillation buffer and counted using a Perkin Elmer Liquid Scintillation Analyzer.

Results and Discussion

In order to form 3-(p-isothiocyanatophenyl)propanoic acid 103, 3-(p-aminophenyl)propanoic acid 102 was added to thiophosgene in water. The isothiocyanate bond of 103 was then conjugated to the terminal amino group of ADAC to form a thiourea linkage. The new product, 104, had a terminal carboxyl group that could be coupled to the amino group of the G3 PAMAM dendrimer. To synthesize 107, diethylenetriamine was heated with methyl ester 105, which was similar to a previous method. This product has a terminal primary amine group that could be coupled to the G2.5 PAMAM dendrimer, with preference for its acylation over the secondary amine.

Both 104 and 107, the new ADAC derivatives, had slightly lower affinity than ADAC itself at the human $A_1AR$, with $K_i$ values of 30 nM and 43 nM, respectively. While 104 retained similar selectivity to ADAC towards the $A_1AR$ over the $A_{2A}AR$, 107 was slightly less selective. However, 107 had a significantly lower $EC_{50}$ value in [$^{35}$S]GTPγS binding, a functional assay for G1 protein activation, than 104 and even ADAC itself. Compound 107 was the most potent compound in this set of derivatives with an $EC_{50}$ value of 50 nM.

To compare 2.5 PAMAM-conjugates of $A_1AR$ agonists with G3 PAMAM-conjugates of similar agonists, 107 and ADAC were attached to G2.5 PAMAM dendrimer, and 104 was conjugated to G3 PAMAM dendrimer. Both dendrimers also had an Alexa-Fluor 488 moiety attached, and the G3 PAMAM derivative was partially acetylated to decrease toxicity.

Figure 42:
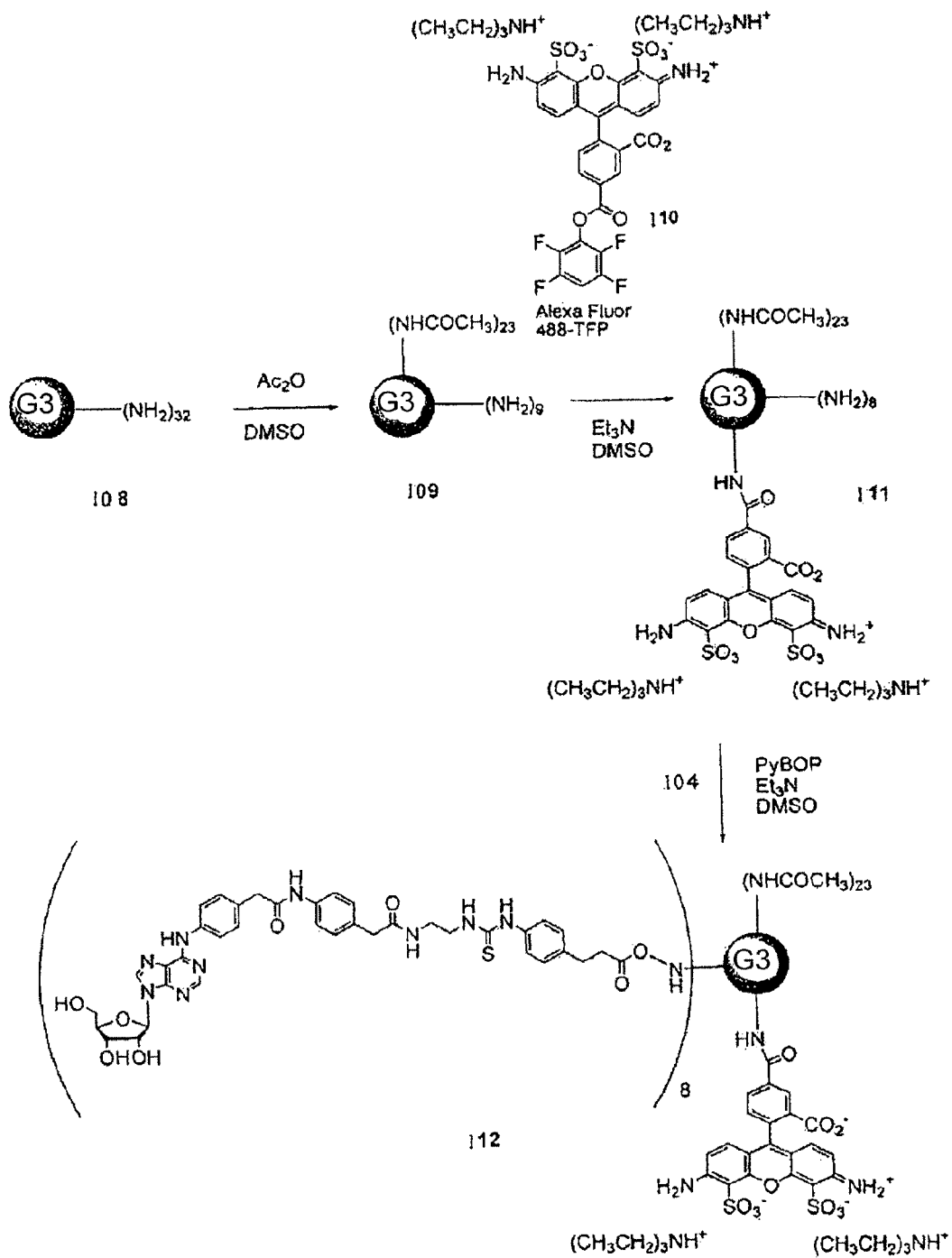
FIG. 42 depicts a method of preparing dendrimer conjugate 112 in accordance with an embodiment of the invention.

G3-PAMAM-AF488-4 (112) was synthesized as shown in FIG. 42. First, the G3 dendrimer was partially acetylated with acetic anhydride. Next, the Alexa-Fluor 488 moiety was attached using PyBOP coupling with triethylamine. Finally, a peptide bond was formed between the carboxyl group of 102 and several terminal amines on the G3 dendrimer. NMR showed that approximately eight molecules of 102 were attached per dendrimer. This meant that the amino groups on the dendrimer appeared to be fully derivatized. Each dendrimer contained on average eight units of 104, one AF488 moiety, and twenty-three acetyl groups.

In the radioligand binding studies, the G3 dendrimer-ligand conjugate 112 had a slightly lower affinity and was slightly less selective than the free monomer 104. The control dendrimer, 111, which contained the acetamide and AF488 moieties but not the ligand, showed no binding at the $A_1$ receptor and weak binding inhibition at the $A_{2A}$ receptor, which was evident only at 10 μM. It is possible that the dendrimer conjugate at high concentrations associated with the radioligand. The control dendrimer 111 also showed slight activity at 10 μM in the stimulation of [$^{35}$S]GTPγS binding, but this could also be due to the sequestering of the radioligand. The G3 dendrimer ligand conjugate 112 had an $EC_{50}$ value that was 5 times lower than the free monomer. Therefore, conjugating the ligand to the dendrimer improved the activation of the receptor even though the affinity was slightly weaker.

In order to attach AF488 to the G2.5 dendrimer, it was necessary to synthesize a new AF488 derivative with a terminal primary amine. Initial attempts were made to add ethylenediamine to 110 using triethylamine in DMF or DMSO, but the compound did not appear stable under these conditions. Therefore, a new method using ethylenediamine in 0.1 M $NaB_4O_7$, pH 8.5, was devised. After HPLC purification and lyophilization, 113 was formed with 93% yield.

107 has similar binding when conjugated to the dendrimer as in its free monomer form. In the functional, GTPγS binding assay, the dendrimer ligand conjugate was even more potent than the monomer.

TABLE 5

$K_i$ Values for Binding of Nucleoside Monomers and Dendrimer Conjugates at $A_1$ and $A_{2A}$ ARs[a]

| Compound | $A_1AR$ (nM) | $A_{2A}AR$ (nM) |
|---|---|---|
| 101 | 10.4 ± 3.8 | 370 ± 100 |
| 104 | 30 ± 9 | 800 ± 360 |
| 107 | 43 ± 5 | 300 ± 20 |
| 111 | No binding[b] | 20 ± 7% |
| 112 | 55 ± 10 | 405 ± 170 |

[a]All experiments were performed using adherent CHO cells stably expressing the $A_1AR$ or HEK cells stably expressing $A_{2A}AR$. Binding was carried out as described in methods using [$^3$H]CCPA or [$^3$H]CGS21680. Values are expressed as $K_i$ values (mean ± SEM, n = 3) or as displacement of the radioligand at 10 μM.
[b]Inhibition of radioligand binding <10% at 10 μM.

TABLE 6

$EC_{50}$ Values for [$^{35}$S]GTPγS Binding of Nucleoside Monomers and Dendrimer Conjugates at $A_1$ and $A_{2A}$ ARs[a]

| Compound | $A_1AR$ (nM) |
|---|---|
| 101 | 120 ± 13 |
| 104 | 3000 ± 1300 |

TABLE 6-continued

EC$_{50}$ Values for [$^{35}$S]GTPγS Binding of Nucleoside Monomers
and Dendrimer Conjugates at A$_1$ and A$_{2A}$ ARs$^a$

| Compound | A$_1$AR (nM) |
|---|---|
| 107 | 50 ± 6 |
| 111 | ~10,000 |
| 112 | 520 ± 160 |

$^a$All experiments were performed using adherent CHO cells stably expressing the A$_1$AR. Binding was carried out as described in methods using [$^{35}$S]GTPγS. Values are expressed as EC$_{50}$ values (mean ± SEM, n = 3).

EXAMPLE 5

Figure 44A:
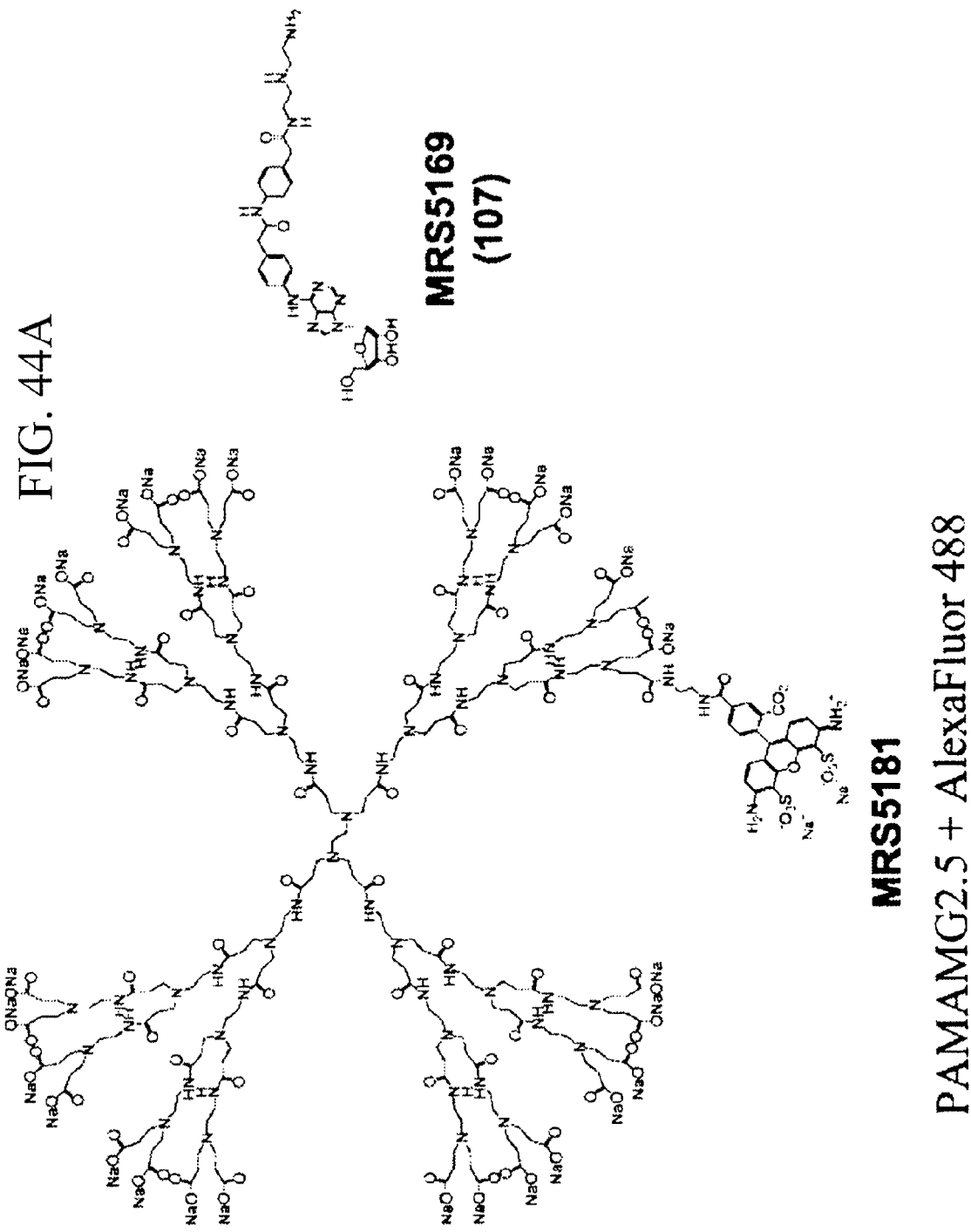
FIG. 44A depicts a first part of a method of preparing dendrimer conjugate 117 in accordance with an embodiment of the invention.
Figure 44B:
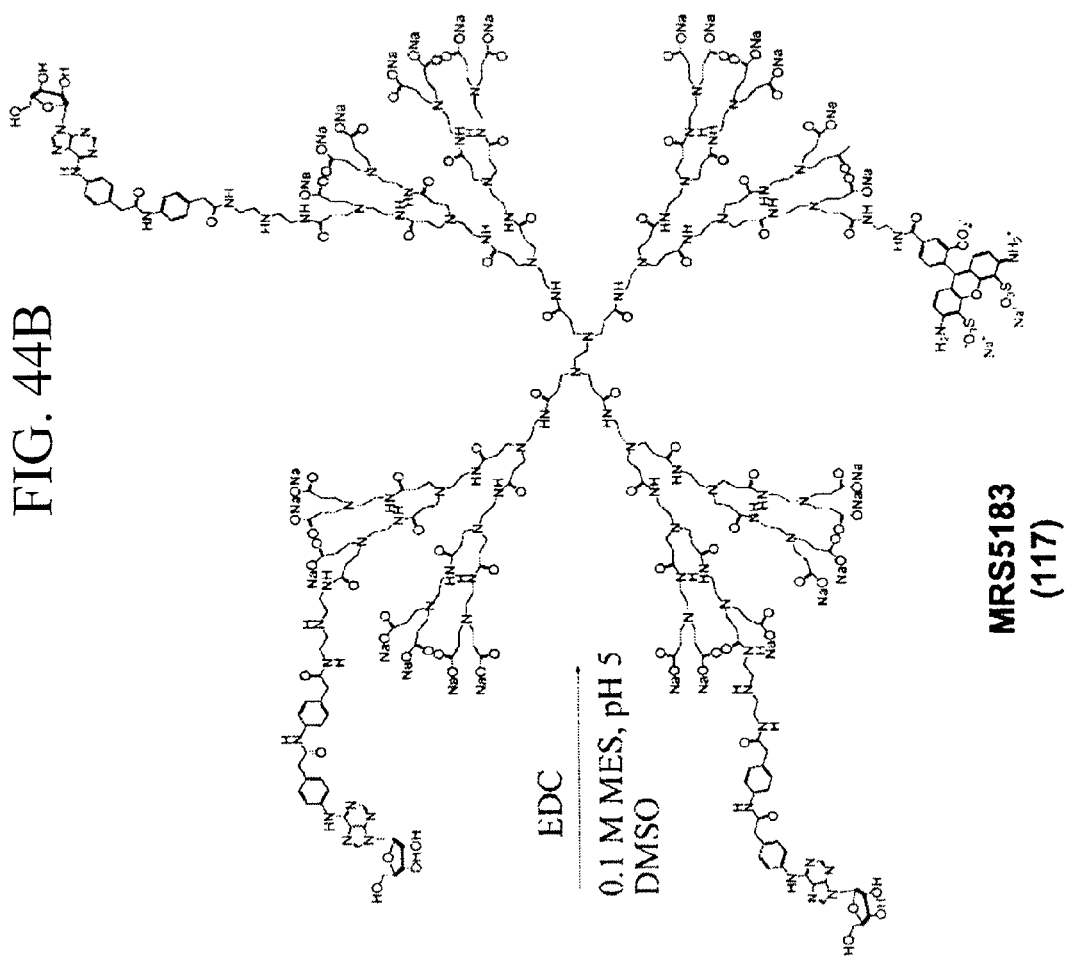
FIG. 44B depicts the second part of the method.
Figure 45C:
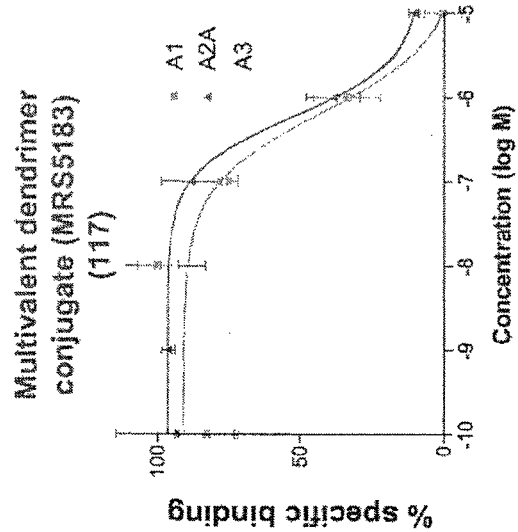
FIG. 45C depicts the percent specific binding of the conjugate 117 at the $A_1$, $A_{2A}$, and $A_3$ adenosine receptors.
Figure 45A:
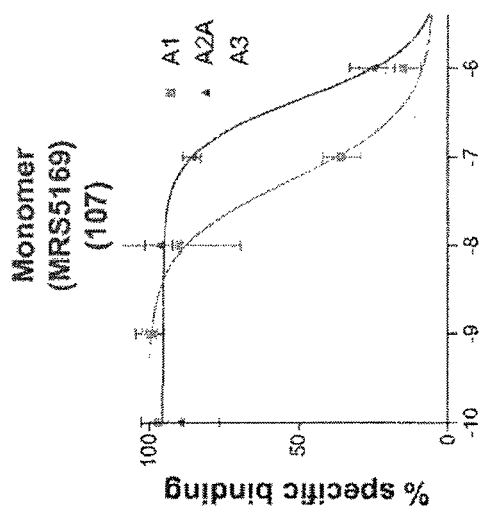
FIG. 45A depicts the percent specific binding of ADAC congener 107 at $A_1$, $A_{2A}$, and $A_3$ adenosine receptors.
Figure 45B:
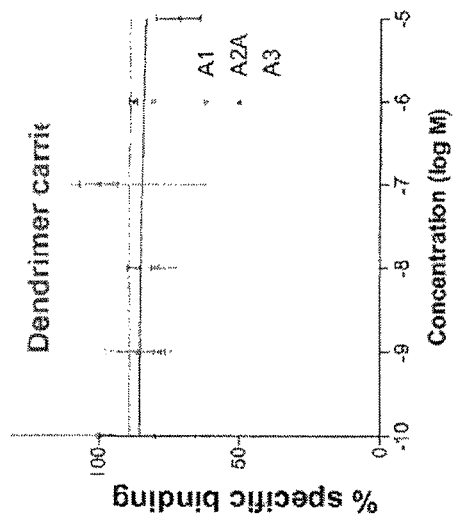
FIG. 45B depicts the percent specific binding of the dendrimer at the $A_1$, $A_{2A}$, and $A_3$ adenosine receptors.
Figure 46B:
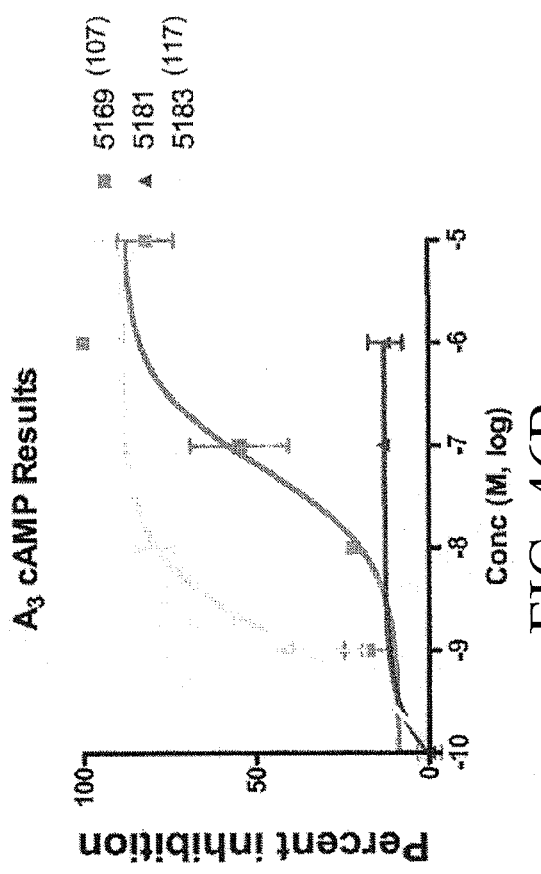
FIG. 46B depicts percent inhibition of cAMP production at the $A_3$ adenosine receptor for congener 107, the dendrimer, and conjugate 117 in accordance with an embodiment of the invention.
Figure 46A:
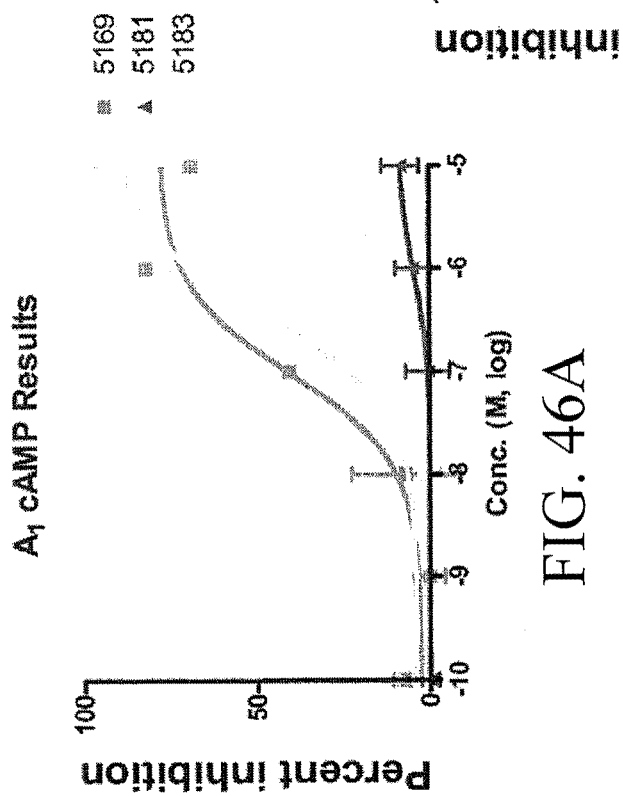
FIG. 46A depicts percent inhibition of cAMP production at the $A_1$ adenosine receptor for congener 107, the dendrimer, and conjugate 117 in accordance with an embodiment of the invention.
Figure 47:
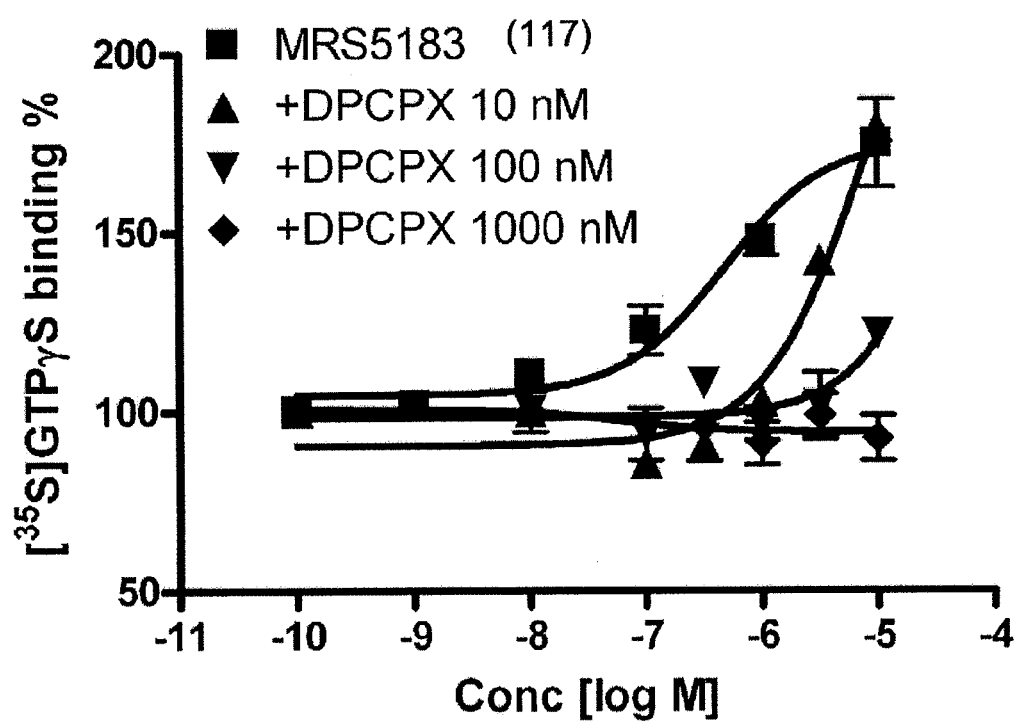
FIG. 47 depicts activation of [$^{35}$S]GTγPS binding by conjugate 117 and which is antagonized by radioligand DPCPX (8-cyclopentyl-[3H]-1,3-dipropylxanthine).

This Example illustrates a preparation and some of the properties of conjugate 117 in accordance with an embodiment of the invention. Conjugate 117, which included congener 107 and fluorescent marker Alexa Fluor 488, was prepared as shown in FIG. 44. The results of binding assay are shown in FIGS. 45A-45C and the data are set forth in Table 7. The results of cAMP inhibition are shown in FIG. 46 and the data are set forth in Table 8. The results of activation of [$^{35}$S]GTγPS binding by conjugate 117 and which is antagonized by radioligand DPCPX are shown in FIG. 47.

TABLE 7

Results of binding assay

| Compound | A$_1$ (nM) | A$_{2A}$ (nM) | A$_3$ (nM) |
|---|---|---|---|
| 107 | 43 ± 5 | 300 ± 20 | 10 ± 2 |
| 117 | 320 ± 20 | 470 ± 50 | 2.4 ± 0.4 |

TABLE 8

Results of cAMP inhibition assay

| Receptor | 107 (K$_i$, nM) | MRS5181 Dendrimer carrier | 117 Conjugate (K$_i$, nM) |
|---|---|---|---|
| A$_1$ | 72 | N/A | 350 |
| A$_3$ | 61 | N/A | 1.2 |

The foregoing results show that conjugate 117 has high selectivity for A3 adenosine receptor.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A conjugate comprising a dendrimer, at least one ligand covalently linked to the dendrimer, and optionally one or more surface modifying moieties covalently linked to the dendrimer, wherein the ligand is a functionalized congener of an agonist or antagonist of a receptor of the G-protein coupled receptor (GPCR) superfamily, with the proviso that when a functionalized congener of an agonist or antagonist of a P2Y receptor is present as a ligand, the conjugate also includes at least one additional ligand which is a functionalized congener of an agonist or antagonist of an adenosine receptor selected from the group consisting of A$_1$, A$_{2A}$, A$_{2B}$, and A$_3$ adenosine receptors.

2. The conjugate of claim 1, wherein the ligand is a functionalized congener of an agonist of a receptor of the GPCR superfamily.

3. The conjugate of claim 1, wherein the ligand is a functionalized congener of an agonist of an adenosine receptor selected from the group consisting of A$_1$, A$_{2A}$, A$_{2B}$, and A$_3$ adenosine receptors.

4. The conjugate of claim 1, wherein the ligand is a functionalized congener of an antagonist of a receptor of the GPCR superfamily.

5. The conjugate of claim 4, wherein the antagonist is an antagonist of an adenosine receptor, purinergic receptor, or a muscarinic receptor.

6. The conjugate of claim 1, wherein the ligand is a functionalized congener of an antagonist of an adenosine receptor selected from the group consisting of A$_1$, A$_{2A}$, A$_{2B}$, and A$_3$ adenosine receptors.

7. The conjugate of claim 1, wherein the ligand is a functionalized congener of a purinergic receptor antagonist.

8. The conjugate of claim 7, wherein the purinergic receptor antagonist is a P2Y$_1$ receptor antagonist.

9. The conjugate of claim 1, wherein the ligand is a functionalized congener of an of a muscarinic receptor.

10. The conjugate of claim 9, wherein the muscarinic receptor is M$_1$ muscarinic receptor.

11. The conjugate of claim 1, wherein the dendrimer is a poly(amidoamine) (PAMAM) dendrimer.

12. The conjugate of claim 11, wherein the PAMAM dendrimer is of generation 2 to 10.

13. The conjugate of claim 3, wherein the ligand is a functionalized congener of an A$_1$ adenosine receptor agonist.

14. The conjugate of claim 13, wherein the $A_1$ adenosine receptor agonist is selected from the group consisting of adenosine, 6-cyclopropyl adenosine, 2-chloro, 6-cyclopropyl adenosine, S(−)-ENBA, $N^6$-[4-(2-aminoethylaminocarbonylmethyl)phenyl]adenosine (ADAC), 1S-[1a,2b,3b,4a(S*)]-4-[7-[[1-[(3-chloro-2-thienyl)methylpropyl]propyl-amino]-3H-imidazo[4,5-b]pyridyl-3-yl]-N-ethyl-2,3-dihydroxycyclopentane carboxamide (AMP579), 2-chloro-N[6]-[(R)-(benzothiazolylthio-2-propyl]adenosine (NNC 21-0136), (N-[1S trans-2-hydroxycyclopentyl] adenosine) (GR 79236), N-(3-tetrahydrofuranyl)-6-aminopurine riboside (Tecadenoson or CVT-510), (((5-(6-(oxolan-3-yl) amino)purin-9-yl)-3,4-dihydroxyoxolan-2-yl)methoxy)-N-methylcarboxamide (CVT-2759), Selodenoson, and 6-cyclohexyl-2′-O-methyl-adenosine (SDZ WAG 994).

15. The conjugate of claim 14, wherein the $A_1$ adenosine receptor agonist is $N^6$-[4-(2-aminoethylaminocarbonylmethyl)phenyl]adenosine (ADAC).

16. The conjugate of claim 13, wherein the functionalized congener is an $A_1$ adenosine receptor agonist having a purine nucleoside moiety and a functional group at the $N^6$ position of the purine nucleoside moiety, wherein the functional group has the formula (I):

$$N^6H\text{—}Ar^1\text{—}CH_2\text{—}C(=O)NH\text{—}R^1 \qquad (I)$$

wherein $R^1$ is $Ar^2\text{—}CH_2\text{—}C(=O)NH\text{—}(CH_2)_a\text{—}NH\text{—}R^2$, $Ar^2\text{—}CH_2\text{—}C(=O)(CH_2)_a\text{—}NH\text{—}R^2$ or $[(CH_2)_b\text{—}NH]_c\text{—}R^2$ and $R^2$ is H or $C(=O)NH\text{—}Ar^3\text{—}(CH_2)_c\text{—}C(=O)OH$, $C(=O)R^3$, $C(=S)Ar^4\text{—}NCS$, or $C(=S)Ar^4\text{—}NH(CH_2)_f NH_2$, wherein $Ar^1$, $Ar^2$, $Ar^3$, and $Ar^4$ are $C_6$-$C_{20}$ aryl, $R^3$ is $C_1$-$C_6$ alkyl, and a, b, c, and f are independently 1-6.

17. The conjugate of claim 16, wherein $Ar^1$, $Ar^2$, $Ar^3$, and $Ar^4$ are phenyl.

18. The conjugate of claim 16, wherein $R^3$ is $C_1$-$C_3$ alkyl.

19. The conjugate of claim 13, wherein the functionalized congener has one of the following formulas (Ia)-(Ic):

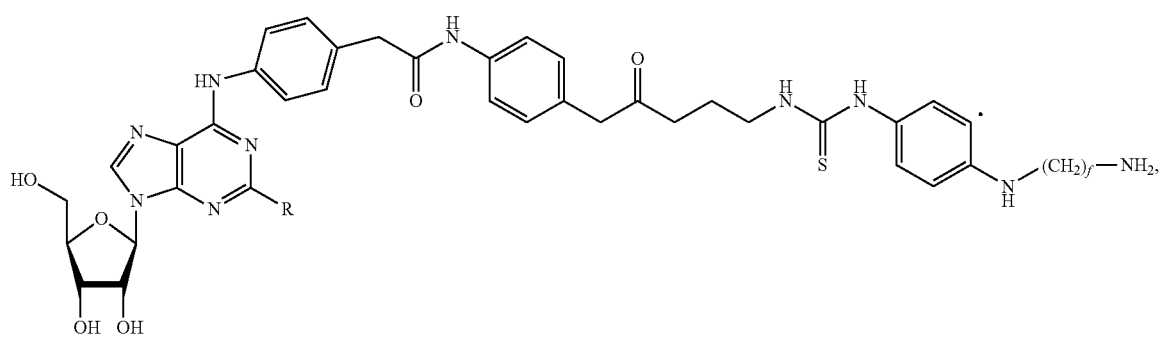

(Ia)

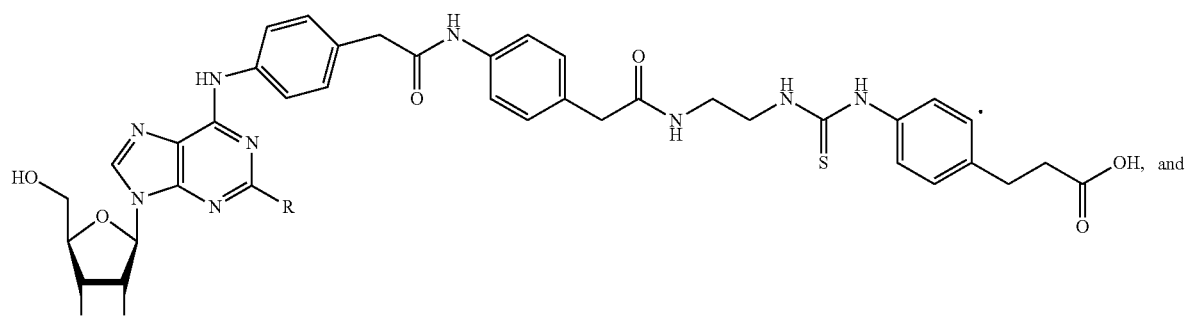

(Ib)

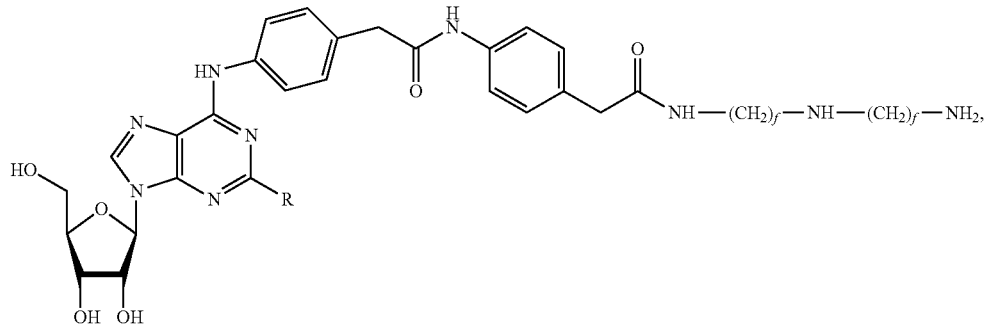

(Ic)

wherein R is hydrogen or halo.

20. The conjugate of claim 3, wherein the ligand is a functionalized congener of an $A_{2A}$ adenosine receptor agonist.

21. The conjugate of claim 20, wherein the $A_{2A}$ adenosine receptor agonist is selected from the group consisting of 2-[4-(2-aminoethylaminocarbonylethyl)phenylethylamino]-5'-N-ethylcarboxamidoadenosine (APEC), 2-[4-(2-carboxyethyl)phenylethylamino]-5'-N-ethylcarboxamidoadenosine (CGS21680), adenosine 5'-N-ethylcarboxamide (NECA), (2-[2-(4-chlorophenyl)-ethoxy]-adenosine) (MRE 9004), $N^6$-[2-(3,5-dimethoxyphenyl)-2-(2-methylphenyl)-ethyl]adenosine (DPMA), and binodenoson.

22. The conjugate of claim 21, wherein the $A_{2A}$ adenosine receptor agonist is selected from the group consisting of 2-[4-(2-aminoethylaminocarbonylethyl)phenylethylamino]-5'-N-ethylcarboxamidoadenosine (APEC) and 2-[4-(2-carboxyethyl)phenylethylamino]-5'-N-ethylcarboxamidoadenosine (CGS21680).

23. The conjugate of claim 20, wherein the functionalized congener is an $A_{2A}$ adenosine receptor agonist having a purine nucleoside moiety and a functional group at the 2-position of the purine nucleoside moiety, wherein the functional group has the formula (II):

$$\text{NH}-(\text{CH}_2)_d-\text{Ar}^5-(\text{CH}_2)_e-\text{C}(=\text{O})-\text{R}^4 \quad \text{(II)};$$

wherein $R^4$ is OH or $NH-(CH_2)_f-NH-R^5$ wherein $R^5$ is H, $C(=O)R^3$, $(CH_2)_j NH_2$, or $C(=S)-NH-Ar^6-R^6$, wherein $R^6$ is NCS, $NH-(C=S)-NH-(CH_2)_g-NH_2$, $(CH_2)_h COOH$, or $(CH_2)_i-NH-C(=O)R^3$, wherein $Ar^5$ and $Ar^6$ are $C_6$-$C_{20}$ aryl, $R^3$ is $C_1$-$C_6$ alkyl, and d to i are independently 1-6.

24. The conjugate of claim 23, wherein $Ar^5$ and $Ar^6$ are phenyl.

25. The conjugate of claim 23, wherein $R^3$ is $C_1$-$C_3$ alkyl.

26. The conjugate of claim 23, wherein the functionalized congener has one of the following formulas (IIa)-(IIe):

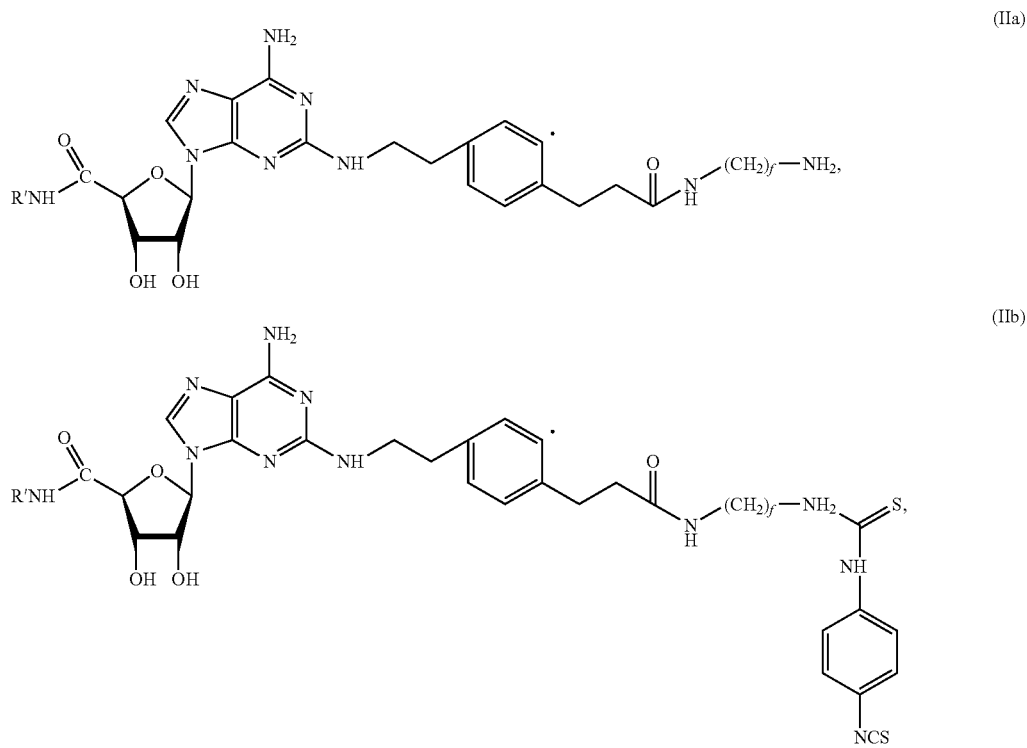

-continued (IIc)

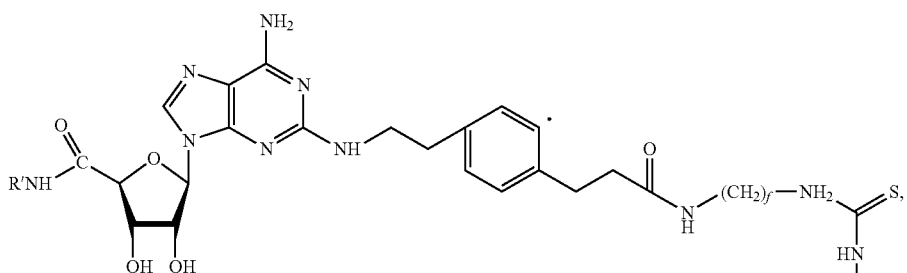

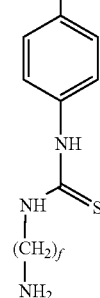

(IId)

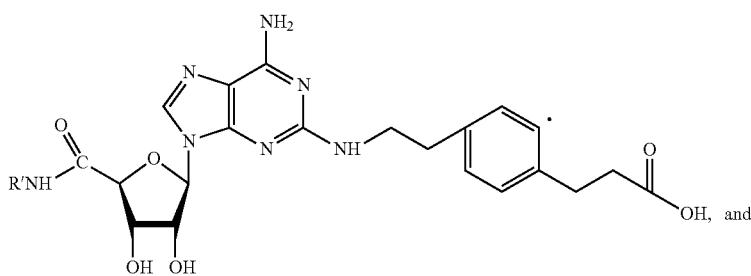

(IIe)

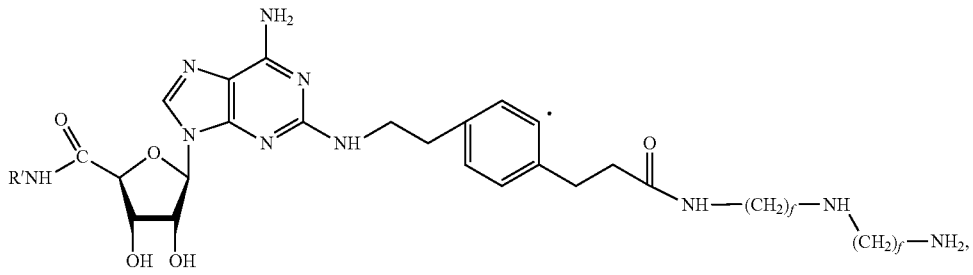

wherein R' is $C_1$-$C_4$ alkyl.

27. The conjugate of claim 3, wherein the ligand is a functionalized congener of an $A_{2B}$ adenosine receptor agonist.

28. The conjugate of claim 27, wherein the $A_{2B}$ adenosine receptor agonist is LUF5835.

29. The conjugate of claim 3, wherein the ligand is a functionalized congener of an $A_3$ adenosine receptor agonist.

30. The conjugate of claim 29, wherein the $A_3$ adenosine receptor agonist is selected from the group consisting of IB-MECA, Cl-IB-MECA, CP-608039, MRS3558, and MRS1898.

31. The conjugate of claim 29, wherein the functionalized congener is (a) an $A_3$ adenosine receptor agonist having a purine nucleoside moiety with a native ribose unit at the $N^7$-position and a functional group of the purine nucleoside moiety at the $N^6$-position, wherein the functional group has the formula (III)):

(III)

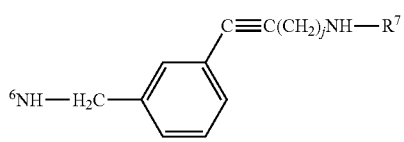

wherein $R^7$ is H,

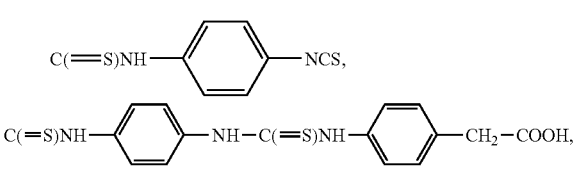

or C(=O)$R^3$, wherein $R^3$ is $C_1$-$C_6$ alkyl, and j is 1 to 6;

or (b) an $A_3$ adenosine receptor agonist having a purine nucleoside moiety with a methanocarba adenine nucleoside unit at the $N^7$-position and a functional group at the 2-position of the nucleoside moiety, wherein the functional group has the formula (IV):

$$C\equiv C-(CH_2)_kC(=O)-R^7 \qquad (IV),$$

wherein $R^7$ is OH or NH—$(CH_2)_l$—$NHR^8$ wherein $R^8$ is H, C(=O)$R^3$, or C(=S)NH—$Ar^7$—$R^9$ wherein $R^3$ is $C_1$-$C_6$ alkyl, $R^9$ is NCS, NH—C(=S)—NH—$(CH_2)_m$—$NH_2$, or $(CH_2)_n$COOH, wherein $Ar^7$ is $C_6$-$C_{20}$ aryl, and k to n are independently 1 to 6.

32. The conjugate of claim 31, wherein $Ar^7$ is phenyl.

33. The conjugate of claim 31, wherein $R^3$ is $C_1$-$C_3$ alkyl.

34. The conjugate of claim 31, wherein the ligand is a functionalized congener of the formula (IIIa) or (IVa):

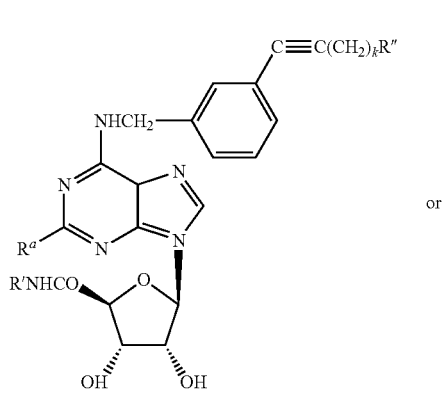

(IIIa)

or

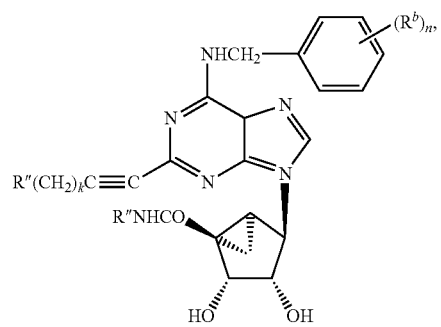

(IVa)

wherein K=1-4;

wherein R' is $C_1$-$C_4$ alkyl; R" is $NH_2$ or COOH; $R^a$ is hydrogen or halo; and $R^b$ is a substituent selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy; or a group of the formula C≡C—$(CH_2)_m$—$COR^{11}$ wherein $R^{11}$ is selected from the group consisting of OH, $OR^{12}$, and $NR^{13}R^{14}$, wherein $R^{12}$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ and diaryl $C_1$-$C_6$ alkyl; $R^{13}$ and $R^{14}$ are independently selected from the group consisting of hydrogen, $C_1$-$C_6$ alkyl, and $(CH_2)_mR^{15}$ wherein $R^{15}$ is $NR^{16}R^{17}$, wherein $R^{16}$ and $R^{17}$ are independently selected from the group consisting of hydrogen, $C_1$-$C_6$ alkyl, and $COR^{18}$ wherein $R^{18}$ is hydrogen or $C_1$-$C_6$ alkyl;

wherein m is an integer from 1 to 10; and n is 1-3.

35. The conjugate of claim 6, wherein the antagonist is an $A_1$ adenosine receptor antagonist.

36. The conjugate of claim 35, wherein the ligand has the formula V:

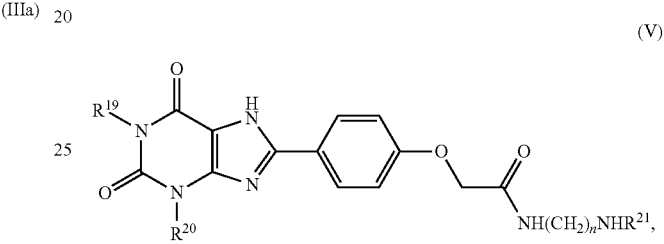

(V)

wherein $R^{19}$ and $R^{20}$ are independently $C_1$-$C_6$ alkyl; and $R^{21}$ is hydrogen or $(CH_2)_mNH_2$, wherein m and n are independently 1 to 6.

37. The conjugate of claim 6, wherein the antagonist is an $A_{2A}$ adenosine receptor antagonist.

38. The conjugate of claim 37, wherein the ligand has the formula VI:

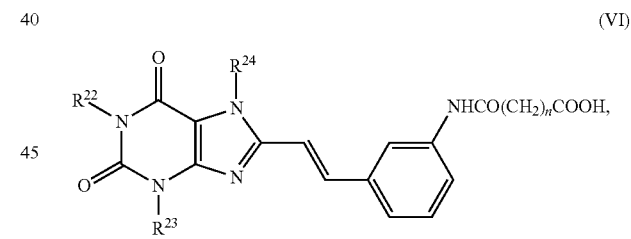

(VI)

wherein $R^{22}$ to $R^{24}$ are independently $C_1$-$C_6$ alkyl and n is 1 to 6.

39. The conjugate of claim 6, wherein the antagonist is an $A_{2B}$ adenosine receptor antagonist.

40. The conjugate of claim 39, wherein the ligand has the formula VII:

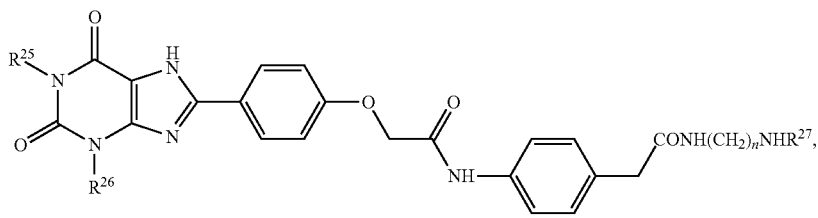

(VII)

wherein $R^{25}$ and $R^{26}$ are independently $C_1$-$C_6$ alkyl; and $R^{27}$ is hydrogen or $(CH_2)_m NH_2$, wherein m and n are independently 1 to 6.

41. The conjugate of claim 6, wherein the antagonist is an $A_3$ adenosine receptor antagonist.

42. The conjugate of claim 41, wherein the ligand has the formula VIII:

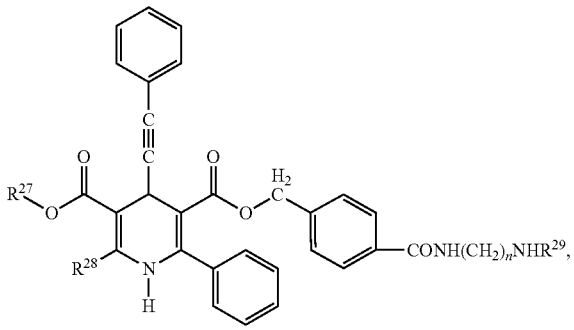

(VIII)

wherein $R^{27}$ and $R^{28}$ are independently $C_1$-$C_6$ alkyl; and $R^{29}$ is hydrogen or $(CH_2)_m NH_2$, wherein m and n are independently 1 to 6.

43. The conjugate of claim 1, wherein the conjugate includes one or more surface modifying moieties.

44. The conjugate of claim 43, wherein the surface modifying moiety is an amine protecting group.

45. The conjugate of claim 43, wherein the surface modifying moiety comprises a hydrophilic group.

46. The conjugate of claim 45, wherein the hydrophilic group comprises a polyethylene glycol moiety.

47. The conjugate of claim 46, wherein the polyethylene glycol moiety is linked to the dendrimer through a bond selected from the group consisting of amide, hydrazide, ether, urethane, urea, thiourea, ester, carbonate, carbamate, hydrazone, carbazone, secondary amine, tertiary amine, and quaternary ammonium.

48. The conjugate of claim 1, which includes covalently bonded agonists or antagonists of at least two different receptors.

49. The conjugate of claim 1, which includes covalently bonded agonists or antagonists of at least three different receptors.

50. The conjugate of claim 1, which at least two different agonists or antagonists of the same type of receptor.

51. The conjugate of claim 1, wherein the degree of loading of the agonist or antagonist is from about 1% to about 99% of the theoretical capacity of the dendrimer.

52. The conjugate of claim 1, wherein the degree of loading of the agonist or antagonist is from about 10% to about 90% of the theoretical capacity of the dendrimer.

53. The conjugate of claim 1, optionally including a covalently bonded fluorescent marker.

54. A pharmaceutical composition comprising a conjugate of claim 1 and a pharmaceutically acceptable carrier.

55. A method of treating a disease which is treatable by agonizing or antagonizing a receptor of the GPCR superfamily in a mammal comprising administering to the mammal an effective amount of a conjugate of claim 1.

56. A diagnostic method for determining a treatment of a patient for a possible agonist or antagonist of the GPCR superfamily or receptors, the treatment comprising:
(a) administering a conjugate comprising a dendrimer, at least one ligand covalently linked to the dendrimer, a fluorescent marker covalently linked to the dendrimer, and optionally one or more surface modifying moieties covalently linked to the dendrimer, wherein the ligand is a functionalized congener of an agonist or antagonist of a receptor of the G-protein coupled receptor (GPCR) superfamily;
(b) obtaining a biological sample from the patient;
(c) determining the level of expression of at least one receptor;
(d) comparing the level of expression of the receptor to that of a normal population; and
(e) if the patient's level of expression is higher than that of the normal population, determining a treatment regimen comprising administering an agonist or antagonist of the receptor whose expression was higher in the patient than that of the normal population.

* * * * *